(12) United States Patent  
Hooven

(10) Patent No.: US 7,001,415 B2  
(45) Date of Patent: Feb. 21, 2006

(54) TRANSMURAL ABLATION DEVICE

(75) Inventor: Michael D. Hooven, Cincinnati, OH (US)

(73) Assignee: AtriCure, Inc., West Chester, OH (US)

( * ) Notice: Subject to any disclaimer, the term of this patent is extended or adjusted under 35 U.S.C. 154(b) by 0 days.

(21) Appl. No.: 10/015,355

(22) Filed: Dec. 12, 2001

(65) Prior Publication Data

US 2002/0115993 A1    Aug. 22, 2002

Related U.S. Application Data

(60) Division of application No. 10/038,506, filed on Nov. 9, 2001, which is a continuation-in-part of application No. 10/032,378, filed on Oct. 26, 2001, now Pat. No. 6,932,811, which is a continuation-in-part of application No. 09/844,225, filed on Apr. 27, 2001, now Pat. No. 6,517,536, which is a continuation-in-part of application No. 09/747,609, filed on Dec. 22, 2000, now Pat. No. 6,546,935.

(60) Provisional application No. 60/200,072, filed on Apr. 27, 2000.

(51) Int. Cl.  
*A61F 7/00* (2006.01)

(52) U.S. Cl. .................. 607/96; 607/101; 607/105; 607/113

(58) Field of Classification Search .................. 606/41, 606/45, 48–52, 44, 46; 607/96, 101, 102, 607/105, 113  
See application file for complete search history.

(56) References Cited

U.S. PATENT DOCUMENTS

| 1,127,948 A | 2/1915 | Wappler |
| 2,004,559 A | 6/1935 | Wappler et al. |
| 3,470,875 A | 10/1969 | Johnson et al. |
| 3,630,207 A | 12/1971 | Kahn et al .................. 128/350 |
| 3,901,242 A | 8/1975 | Storz .......................... 128/303 |

(Continued)

FOREIGN PATENT DOCUMENTS

DE    43 13 903 C1    9/1994

(Continued)

OTHER PUBLICATIONS

English abstract re Japanese Patent Application No. JP 1996000275351, published Apr. 28, 1997.

(Continued)

*Primary Examiner*—Rosiland Rollins  
(74) *Attorney, Agent, or Firm*—Cook,Alex,McFarron, Manzo,Cummings & Mehler, Ltd.

(57) ABSTRACT

A method and apparatus for transmural ablation using an instrument containing two electrodes or cryogenic probes. A clamping force is exerted on the two electrodes or probes such that the tissue of the hollow organ is clamped therebetween. Bipolar RF energy is then applied between the two electrodes, or the probes are cryogenically cooled, thus ablating the tissue therebetween. A monitoring device measures a suitable parameter, such as impedance or temperature, and indicates when the tissue between the electrodes has been fully ablated.

11 Claims, 52 Drawing Sheets

U.S. PATENT DOCUMENTS

| | | | |
|---|---|---|---|
| 4,043,342 A | 8/1977 | Morrison, Jr. | 128/303 |
| 4,312,337 A | 1/1982 | Donohue et al. | |
| 4,353,371 A | 10/1982 | Cosman | 128/303 |
| 4,492,231 A | 1/1985 | Auth | 128/303 |
| 4,590,934 A | 5/1986 | Malis et al. | 128/303 |
| 4,706,667 A | 11/1987 | Roos | 128/303 |
| 4,732,149 A | 3/1988 | Sutter | 128/303 |
| 4,802,475 A | 2/1989 | Weshahy | 128/303 |
| 4,940,064 A | 7/1990 | Desai | 128/784 |
| 5,009,661 A | 4/1991 | Michelson | |
| 5,013,312 A | 5/1991 | Parins et al. | 606/37 |
| 5,033,477 A | 7/1991 | Chin et al. | |
| 5,044,947 A | 9/1991 | Sachdeva et al. | |
| 5,071,428 A | 12/1991 | Chin et al. | |
| 5,083,565 A | 1/1992 | Parins | 128/642 |
| 5,085,657 A | 2/1992 | Ben-Simhon | 606/42 |
| 5,087,243 A | 2/1992 | Avitall | 606/20 |
| 5,116,332 A | 5/1992 | Lottick | 606/42 |
| 5,125,928 A | 6/1992 | Parins et al. | |
| 5,147,355 A | 9/1992 | Friedman | 606/23 |
| 5,190,541 A | 3/1993 | Abele et al. | 606/46 |
| 5,207,691 A | 5/1993 | Nardella | 606/142 |
| 5,217,460 A | 6/1993 | Knoepfler | 606/52 |
| 5,231,995 A | 8/1993 | Desai | 128/784 |
| 5,242,441 A | 9/1993 | Avitall | 606/41 |
| 5,242,458 A | 9/1993 | Bendel et al. | |
| 5,250,047 A | 10/1993 | Rydell | 606/48 |
| 5,250,075 A | 10/1993 | Badie | 606/207 |
| 5,254,130 A | 10/1993 | Poncet et al. | |
| 5,263,493 A | 11/1993 | Avitall | 607/122 |
| 5,269,326 A | 12/1993 | Verrier | 128/642 |
| 5,269,780 A | 12/1993 | Roos | 606/42 |
| 5,281,215 A | 1/1994 | Milder | 606/20 |
| 5,281,216 A | 1/1994 | Klicek | 606/42 |
| 5,293,869 A | 3/1994 | Edwards et al. | 128/642 |
| 5,306,234 A | 4/1994 | Johnson | |
| 5,318,589 A | 6/1994 | Lichtman | 606/205 |
| 5,323,781 A | 6/1994 | Ideker et al. | |
| 5,327,905 A | 7/1994 | Avitall | 128/772 |
| 5,354,297 A | 10/1994 | Avitall | 606/45 |
| 5,357,956 A | 10/1994 | Nardella | 128/642 |
| 5,397,339 A | 3/1995 | Desai | 607/116 |
| 5,403,312 A | 4/1995 | Yates et al. | 606/50 |
| 5,423,807 A | 6/1995 | Milder | 606/20 |
| 5,429,131 A | 7/1995 | Scheinman et al. | 128/642 |
| 5,429,636 A | 7/1995 | Shikhman et al. | 606/41 |
| 5,438,302 A | 8/1995 | Goble | 331/167 |
| 5,441,483 A | 8/1995 | Avitall | 604/95 |
| 5,443,463 A | 8/1995 | Stern et al. | 606/41 |
| 5,445,638 A | 8/1995 | Rydell et al. | 606/51 |
| 5,449,355 A | 9/1995 | Rhum et al. | 606/41 |
| 5,451,223 A | 9/1995 | Ben-Simhon | 606/42 |
| 5,452,733 A | 9/1995 | Sterman et al. | |
| 5,454,370 A | 10/1995 | Avitall | 128/642 |
| 5,465,716 A | 11/1995 | Avitall | 128/642 |
| 5,472,441 A | 12/1995 | Edwards et al. | 606/41 |
| 5,478,309 A | 12/1995 | Sweezer et al. | 604/4 |
| 5,480,409 A | 1/1996 | Riza | 606/205 |
| 5,487,385 A | 1/1996 | Avitall | 128/642 |
| 5,496,312 A | 3/1996 | Klicek | 606/34 |
| 5,500,011 A | 3/1996 | Desai | 607/116 |
| 5,500,012 A | 3/1996 | Brucker et al. | |
| 5,531,744 A | 7/1996 | Nardella et al. | 606/48 |
| 5,536,267 A | 7/1996 | Edwards et al. | 606/41 |
| 5,549,636 A | 8/1996 | Li | |
| 5,555,883 A | 9/1996 | Avitall | 128/642 |
| 5,562,699 A | 10/1996 | Heimberger et al. | |
| 5,562,700 A | 10/1996 | Huitema et al. | |
| 5,562,721 A | 10/1996 | Marchlinski et al. | 607/99 |
| 5,564,440 A | 10/1996 | Swartz et al. | 128/898 |
| 5,571,215 A | 11/1996 | Sterman et al. | |
| 5,575,766 A | 11/1996 | Swartz et al. | |
| 5,575,805 A | 11/1996 | Li | |
| 5,582,609 A | 12/1996 | Swanson et al. | 606/39 |
| 5,587,723 A | 12/1996 | Otake et al. | 345/118 |
| 5,595,183 A | 1/1997 | Swanson et al. | 128/697 |
| 5,599,350 A | 2/1997 | Schulze et al. | 606/51 |
| 5,611,813 A | 3/1997 | Lichtman | 606/205 |
| 5,620,459 A | 4/1997 | Lichtman | 606/205 |
| 5,642,736 A | 7/1997 | Avitall | 128/772 |
| 5,655,219 A | 8/1997 | Jusa et al. | 370/338 |
| 5,672,174 A | 9/1997 | Gough et al. | 606/41 |
| 5,674,220 A | 10/1997 | Fox et al. | 606/51 |
| 5,680,860 A * | 10/1997 | Imran | 600/374 |
| 5,683,384 A | 11/1997 | Gough et al. | 606/41 |
| 5,687,737 A | 11/1997 | Branham et al. | 128/710 |
| 5,688,270 A | 11/1997 | Yates et al. | 606/51 |
| 5,690,611 A | 11/1997 | Swartz et al. | 604/53 |
| 5,693,051 A | 12/1997 | Schulze et al. | 606/51 |
| 5,697,925 A | 12/1997 | Taylor | 606/34 |
| 5,697,928 A | 12/1997 | Walcott et al. | 606/41 |
| 5,702,359 A | 12/1997 | Hofmann et al. | 604/20 |
| 5,702,390 A | 12/1997 | Austin et al. | 606/48 |
| 5,702,438 A | 12/1997 | Avitall | 607/122 |
| 5,709,680 A | 1/1998 | Yates et al. | 606/50 |
| 5,718,703 A | 2/1998 | Chin | 606/49 |
| 5,722,403 A | 3/1998 | McGee et al. | 128/642 |
| 5,725,512 A | 3/1998 | Swartz et al. | 604/280 |
| 5,728,143 A | 3/1998 | Gough et al. | 607/101 |
| 5,730,127 A | 3/1998 | Avitall | 128/642 |
| 5,730,704 A | 3/1998 | Avitall | 600/374 |
| 5,733,280 A | 3/1998 | Avitall | 606/23 |
| 5,735,847 A | 4/1998 | Gough et al. | 606/45 |
| 5,735,849 A | 4/1998 | Baden et al. | 606/51 |
| 5,740,808 A | 4/1998 | Panescu et al. | 128/662 |
| 5,755,664 A | 5/1998 | Rubenstein | 600/377 |
| 5,755,717 A | 5/1998 | Yates et al. | 606/51 |
| 5,759,158 A | 6/1998 | Swanson | 600/508 |
| 5,776,130 A | 7/1998 | Buysse et al. | |
| 5,782,827 A | 7/1998 | Gough et al. | 606/41 |
| 5,782,828 A | 7/1998 | Chen et al. | 606/42 |
| 5,785,706 A | 7/1998 | Bednarek | 606/41 |
| H1745 H | 8/1998 | Paraschac | 606/51 |
| 5,797,906 A | 8/1998 | Rhum et al. | 606/48 |
| 5,797,960 A | 8/1998 | Stevens et al. | 606/213 |
| 5,800,484 A | 9/1998 | Gough et al. | 607/104 |
| 5,807,393 A | 9/1998 | Williamson, IV et al. | 606/32 |
| 5,807,395 A | 9/1998 | Mulier et al. | 606/41 |
| 5,810,804 A | 9/1998 | Gough et al. | 606/41 |
| 5,810,805 A | 9/1998 | Sutcu et al. | 606/45 |
| 5,810,811 A | 9/1998 | Yates et al. | 606/50 |
| 5,814,028 A | 9/1998 | Swartz et al. | |
| 5,817,091 A | 10/1998 | Nardella et al. | 606/38 |
| 5,823,955 A | 10/1998 | Kuck et al. | 600/374 |
| 5,823,956 A | 10/1998 | Roth et al. | 600/374 |
| 5,829,447 A | 11/1998 | Stevens et al. | 128/898 |
| 5,833,690 A | 11/1998 | Yates et al. | 606/52 |
| 5,833,703 A | 11/1998 | Manushakian | 606/174 |
| 5,842,984 A | 12/1998 | Avitall | 600/374 |
| 5,843,075 A | 12/1998 | Taylor | 606/34 |
| 5,843,122 A | 12/1998 | Riza | 606/207 |
| 5,846,238 A | 12/1998 | Jackson et al. | 606/41 |
| 5,849,011 A | 12/1998 | Jones et al. | 606/47 |
| 5,849,020 A | 12/1998 | Long et al. | 606/167 |
| 5,853,411 A | 12/1998 | Whayne et al. | 606/41 |
| 5,855,590 A | 1/1999 | Malecki et al. | |
| 5,855,614 A | 1/1999 | Stevens et al. | 623/11 |
| 5,860,975 A | 1/1999 | Goble et al. | 606/45 |
| 5,863,290 A | 1/1999 | Gough et al. | 606/41 |
| 5,863,291 A | 1/1999 | Schaer | 606/41 |
| 5,868,737 A | 2/1999 | Taylor et al. | 606/34 |
| 5,871,483 A | 2/1999 | Jackson et al. | 606/41 |
| 5,873,896 A | 2/1999 | Ideker | 607/14 |
| 5,876,398 A | 3/1999 | Mulier et al. | |

| | | | |
|---|---|---|---|
| 5,876,400 A | 3/1999 | Songer .................. 606/45 |
| 5,876,401 A | 3/1999 | Schulze et al. ............. 606/51 |
| 5,891,135 A | 4/1999 | Jackson et al. ............. 606/41 |
| 5,891,136 A | 4/1999 | McGee et al. ............. 606/41 |
| 5,891,138 A | 4/1999 | Tu et al. |
| 5,893,863 A | 4/1999 | Yoon ................. 606/170 |
| 5,897,554 A | 4/1999 | Chia et al. |
| 5,899,898 A | 5/1999 | Arless et al. .............. 606/22 |
| 5,899,899 A | 5/1999 | Arless et al. .............. 606/22 |
| 5,902,289 A | 5/1999 | Swartz et al. ............. 604/281 |
| 5,910,129 A | 6/1999 | Koblish et al. ............. 604/95 |
| 5,913,855 A | 6/1999 | Gough et al. ............. 606/41 |
| 5,921,924 A | 7/1999 | Avitall ................. 600/374 |
| 5,924,424 A | 7/1999 | Stevens et al. ............ 128/898 |
| 5,925,038 A | 7/1999 | Panescu et al. ............. 606/41 |
| 5,925,042 A | 7/1999 | Gough et al. ............. 606/41 |
| 5,928,229 A | 7/1999 | Gough et al. ............. 606/41 |
| 5,931,836 A | 8/1999 | Hatta et al. ............. 606/38 |
| 5,935,126 A | 8/1999 | Riza ................. 606/51 |
| 5,938,660 A | 8/1999 | Swartz et al. ............. 606/45 |
| 5,941,251 A | 8/1999 | Panescu et al. ............ 128/899 |
| 5,941,845 A | 8/1999 | Tu et al. ................. 604/53 |
| 5,944,718 A | 8/1999 | Austin et al. ............. 606/48 |
| 5,947,938 A | 9/1999 | Swartz et al. ............. 604/280 |
| 5,951,547 A | 9/1999 | Gough et al. ............. 606/41 |
| 5,951,552 A | 9/1999 | Long et al. ............. 606/46 |
| 5,954,665 A | 9/1999 | Ben-Haim ............. 600/515 |
| 5,961,514 A | 10/1999 | Long et al. ............. 606/41 |
| 5,967,976 A | 10/1999 | Larsen ................. 600/374 |
| 5,971,983 A | 10/1999 | Lesh ................. 606/41 |
| 5,972,026 A | 10/1999 | Laufer et al. ............. 607/96 |
| 5,980,516 A | 11/1999 | Mulier et al. ............. 606/41 |
| 5,980,517 A | 11/1999 | Gough ................. 606/41 |
| 5,984,281 A | 11/1999 | Hacker et al. ............. 261/71 |
| 5,997,533 A | 12/1999 | Kuhns ................. 606/41 |
| 6,010,516 A | 1/2000 | Hulka ................. 606/148 |
| 6,010,531 A | 1/2000 | Donlon et al. ............. 623/2 |
| 6,012,457 A | 1/2000 | Lesh ................. 128/898 |
| 6,013,074 A | 1/2000 | Taylor ................. 606/34 |
| 6,016,809 A | 1/2000 | Mulier et al. ............. 128/898 |
| 6,017,358 A | 1/2000 | Yoon et al. ............. 606/205 |
| 6,023,638 A | 2/2000 | Swanson ............. 600/510 |
| 6,024,740 A | 2/2000 | Lesh et al. ............. 606/34 |
| 6,024,741 A | 2/2000 | Williamson, IV et al. .... 606/40 |
| 6,030,403 A | 2/2000 | Long et al. ............. 606/185 |
| 6,033,402 A | 3/2000 | Tu et al. |
| 6,036,670 A | 3/2000 | Wijeratne et al. ............ 604/96 |
| 6,039,731 A | 3/2000 | Taylor et al. ............. 606/34 |
| 6,039,733 A | 3/2000 | Buysse et al. ............. 606/40 |
| 6,039,748 A | 3/2000 | Savage et al. ............. 606/180 |
| 6,047,218 A | 4/2000 | Whayne et al. ............. 607/122 |
| 6,048,329 A | 4/2000 | Thompson et al. .......... 604/95 |
| 6,050,996 A * | 4/2000 | Schmaltz et al. ............. 606/51 |
| 6,064,902 A | 5/2000 | Haissaguerre et al. |
| 6,068,653 A | 5/2000 | LaFontaine |
| 6,071,281 A * | 6/2000 | Burnside et al. ............. 606/41 |
| 6,083,150 A | 7/2000 | Aznoian et al. |
| 6,083,222 A | 7/2000 | Klein et al. |
| 6,096,037 A | 8/2000 | Mulier et al. |
| 6,110,098 A | 8/2000 | Renirie et al. ............. 600/16 |
| 6,113,595 A | 9/2000 | Muntermann |
| 6,113,598 A * | 9/2000 | Baker ................. 606/51 |
| 6,117,101 A | 9/2000 | Diederich et al. |
| 6,123,703 A | 9/2000 | Tu et al. |
| 6,126,658 A | 10/2000 | Baker |
| 6,142,994 A | 11/2000 | Swanson et al. |
| 6,156,033 A | 12/2000 | Tu et al. |
| 6,161,543 A | 12/2000 | Cox et al. |
| 6,162,220 A | 12/2000 | Nezhat |
| 6,193,713 B1 | 2/2001 | Geistert et al. |
| 6,237,605 B1 | 5/2001 | Vaska et al. |
| 6,264,087 B1 | 7/2001 | Whitman |
| 6,267,761 B1 | 7/2001 | Ryan |
| 6,273,887 B1 | 8/2001 | Yamauchi et al. |
| 6,277,117 B1 | 8/2001 | Tetzlaff et al. |
| 6,292,678 B1 | 9/2001 | Hall et al. |
| 6,296,640 B1 | 10/2001 | Wampler et al. |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,332,089 B1 | 12/2001 | Acker et al. |
| 6,334,860 B1 * | 1/2002 | Dorn ................. 606/48 |
| 6,356,790 B1 | 3/2002 | Maguire et al. |
| 6,358,249 B1 | 3/2002 | Chen et al. |
| 6,391,024 B1 | 5/2002 | Sun et al. |
| 6,443,970 B1 | 9/2002 | Schulze et al. |
| 6,447,507 B1 | 9/2002 | Bednarek et al. |
| 6,464,700 B1 | 10/2002 | Koblish et al. |
| 6,474,340 B1 | 11/2002 | Vaska et al. |
| 6,488,678 B1 | 12/2002 | Sherman |
| 6,488,680 B1 | 12/2002 | Francischelli et al. |
| 6,506,189 B1 | 1/2003 | Rittman, III et al. |
| 6,517,536 B1 * | 2/2003 | Hooven et al. ................. 606/41 |
| 6,540,740 B1 | 4/2003 | Lehmann et al. |
| 6,546,935 B1 | 4/2003 | Hooven |
| 6,575,969 B1 | 6/2003 | Rittman, III et al. |
| 6,610,055 B1 | 8/2003 | Swanson et al. |
| 6,632,222 B1 | 10/2003 | Edwards et al. |
| 6,679,882 B1 | 1/2004 | Kornerup |
| 2001/0031961 A1 | 10/2001 | Hooven |
| 2001/0039419 A1 | 11/2001 | Francischelli et al. |
| 2002/0002329 A1 | 1/2002 | Avitall |
| 2002/0019629 A1 | 2/2002 | Dietz et al. |
| 2002/0032440 A1 | 3/2002 | Hooven |
| 2002/0052602 A1 | 5/2002 | Wang et al. |
| 2002/0082595 A1 | 6/2002 | Langberg et al. |
| 2002/0091382 A1 | 7/2002 | Hooven |
| 2002/0091383 A1 | 7/2002 | Hooven |
| 2002/0091384 A1 | 7/2002 | Hooven |
| 2002/0099364 A1 | 7/2002 | Lalonde |
| 2002/0103484 A1 | 8/2002 | Hooven |
| 2002/0107513 A1 | 8/2002 | Hooven |
| 2002/0107514 A1 | 8/2002 | Hooven |
| 2002/0115990 A1 | 8/2002 | Acker |
| 2002/0120263 A1 | 8/2002 | Brown et al. |
| 2002/0120316 A1 | 8/2002 | Hooven |
| 2002/0128643 A1 | 9/2002 | Simpson et al. |
| 2002/0183738 A1 | 12/2002 | Chee et al. |
| 2003/0004507 A1 | 1/2003 | Francischelli et al. |
| 2003/0009094 A1 | 1/2003 | Segner et al. |
| 2003/0018329 A1 | 1/2003 | Hooven |
| 2003/0028187 A1 | 2/2003 | Vaska et al. |
| 2003/0032952 A1 | 2/2003 | Hooven |
| 2003/0045887 A1 | 3/2003 | Jain et al. |
| 2003/0050557 A1 | 3/2003 | Susil et al. |
| 2003/0060822 A1 | 3/2003 | Schaer et al. |
| 2003/0069572 A1 | 4/2003 | Wellman et al. |
| 2003/0069577 A1 | 4/2003 | Vaska et al. |
| 2003/0073991 A1 | 4/2003 | Francischelli et al. |
| 2003/0078570 A1 | 4/2003 | Heiner et al. |
| 2003/0078574 A1 | 4/2003 | Hall et al. |
| 2003/0093068 A1 | 5/2003 | Hooven |
| 2003/0093104 A1 | 5/2003 | Bonner et al. |
| 2003/0097124 A1 | 5/2003 | Lehmann et al. |
| 2003/0100895 A1 | 5/2003 | Simpson et al. |
| 2003/0114844 A1 | 6/2003 | Ormsby et al. |
| 2003/0120268 A1 | 6/2003 | Bertolero et al. |
| 2003/0125726 A1 | 7/2003 | Maguire et al. |
| 2003/0125729 A1 | 7/2003 | Hooven |
| 2003/0125730 A1 | 7/2003 | Berube et al. |
| 2003/0130598 A1 | 7/2003 | Manning et al. |
| 2003/0135207 A1 | 7/2003 | Langberg et al. |
| 2003/0144657 A1 | 7/2003 | Bowe et al. |
| 2003/0158548 A1 | 8/2003 | Phan et al. |
| 2003/0171745 A1 | 9/2003 | Francischelli et al. |
| 2003/0178032 A1 | 9/2003 | Ingle et al. |

FOREIGN PATENT DOCUMENTS

| | | |
|---|---|---|
| EP | 0 450 608 A1 | 10/1991 |
| EP | 0 765 639 | 4/1997 |
| WO | WO 92/05828 A1 | 4/1992 |
| WO | WO 93/25267 A1 | 12/1993 |
| WO | WO 97/10764 A1 | 3/1997 |
| WO | WO 97/32525 | 9/1997 |
| WO | WO 98/17187 | 4/1998 |
| WO | WO 98/53750 | 12/1998 |
| WO | WO 99/02096 | 1/1999 |
| WO | WO 99/04696 | 2/1999 |
| WO | WO 99/12487 | 3/1999 |
| WO | WO 99/44519 | 9/1999 |
| WO | WO 99/56486 | 11/1999 |
| WO | WO 99/56644 | 11/1999 |
| WO | WO 99/56648 | 11/1999 |
| WO | WO 99/59486 | 11/1999 |
| WO | WO 00/21449 | 4/2000 |
| WO | WO 00/27311 | 5/2000 |
| WO | WO 00/27312 | 5/2000 |
| WO | WO 00/27313 | 5/2000 |
| WO | WO 11/27310 A2 | 5/2000 |
| WO | WO 11/27310 A3 | 5/2000 |
| WO | WO 00/42931 | 7/2000 |
| WO | WO 00/42932 | 7/2000 |
| WO | WO 00/42933 | 7/2000 |
| WO | WO 00/42934 | 7/2000 |
| WO | WO 01/82812 A1 | 11/2001 |
| WO | WO 01/82813 A2 | 11/2001 |
| WO | WO 01/82813 A3 | 11/2001 |
| WO | WO 02 / 087454 A1 | 11/2002 |

OTHER PUBLICATIONS

Yoshio Kosakai, M.D., et al., "Cox Maze Procedure for Chronic Atrial Fibrillation Associated with Mirtal Valve Disease," The Journal of Thoracic and Cardiovascular Surgery, 1994; Vol. 108, No. 6, pp. 1049-1055.

Ki-Bong Kim, M.D., et al., Abstract "The Cox-Maze III Procedure for Atrial Fibrillation Associated with Rheumatic Mitral Valve Disease," The Annals of Thoracic Surgery, 2000; pp. 1-5.

Hiroshi Nakagawa, et al., Abstract, "Creation of Long Linear Transmural Radiofrequencey Lesions in Atrium Using a Novel Spiral Ribbon—Saline Irrigated Electrode Catheter," Journal of American College of Cardiology, Feb. 1996.

Taijiro Sueda, et al., "Efficacy of a Simple Left Atrial Procudure for Chronic Atrial Procedure for Chronic Atrial Fibrillation in Mitral Valve Operations," The Annals of Thoracic Surgery, 1997, Vol. 63, pp. 1070-1073.

Re: Dr. Adam E. Saltman, New Program in Surgical Electrophysiology Established, Interet Website of Departmental News, Dept. of Surgery, University Hospital & Medical Center, Stony Brook State University of New York (www.informatics.synysb.edu/surgery/electro-news.html); 2000, pp. 1-2.

Mien-Cheng Chen, M.D., et al., "Radiofrequency and Cryoablation of Atrial Fibrillation in Patients Undergoing Valvular Operations," Anals of Thoracic Surgery, 1998:65: 1666-1672.

Arif Elvan, M.D., et al., Abstract, "Radiofrequency Catheter Ablation of the Atria Reduces Inducibility and Duration of Atrial Fibrillation in Dogs," Circulation, 1995:91:2235-2244.

Warren M. Jackman, M.D., et al.., "Radiofrequency Current Directed Across the Mitral Anulus With a Bipolar Epicardial—Endocardial Catheter Electrode Configuration in Dogs," CIRCULATION, 1988; vol. 78, No. 5, pp. 1288-1297.

James L. Cox, M.D., Ed., "Seminars in Thoracic and Cardiovascular Surgery: The Maze Procedure for Atrial Fibrillation," 2000, vol. 12, No. 1.

Lauran Neergaard, "Slicing a Heart to Make it Beat," Article from The Associated Press, Mar. 26, 1998, Website (www.nando.com/newsroom/ntn/health/032698/health24_22737_body.html).

Yoshito Inoue, et al., "Video Assisted Thoracoscopic and Cardioscopic Radiofrequency Maze Ablation," Asaio Journal, 1997, pp. 334-337.

Yoshito Inoue, et al., Abstract, "Video Assisted Thoracoscopic and Cardioscopic Radiofrequency Maze Ablation," Asaio Journal, 1997.

Mary O. Palazzo, RN, MS, CCRN, "What You Need To Know—a-fib 101, " from the Atrial Fibrillation Page Website (www.members.aol.com/mazern/afib101.htm) Jun. 5, 2000.

Mary O. Palazzo, RN, MS, CCRN, "What You Need To Know—maze FAQ," from the Atrial Fibrillation Page Website (www.members.aol.com/mazern/mazefaq.htm) Nov. 25, 1999.

Mary O. Palazzo, RN, MS, CCRN, "What You Need To Know—maze FAQ," from the Atrial Fibrillation Page Website (www.members.aol.com/mazern/mazefaq.htm) Jun. 21, 2000.

Stuart P. Thomas, et al., "Mechanism, Localization and Cure of Atrial Arrhythmias Occurring After a New Intraoperative Endocardial Radiofrequency Ablation Procedure for Atrial Fibrillation," Journal of the American College of Cardiology, 2000, vol. 35, No. 2, pp. 442-450.

Ivan M. Robbins, M.D., et al., "Pulmonary Vein Stenosis After Catheter Ablation of Atrial Fibrillation," Circulation, 1998; 98:1769-1775.

Akira T. Kawaguchi, et al., "Factors Affecting Rhythm After the Maze Procedure for Atrial Fibrillation," CIRCULATION, 1998; Vol. 78, No. 5, pp. 1288-1296.

Taijiro Sueda, et al., "Simple Left Atrial Procedure for Chronic Atrial Fibrillation Associated with Mitral Valve Disease," The Annals of Thoracic Surgery, 1996;62:1796-1800.

Berjano, Enrique J. et al. "Bipolar Electrosurgery With Long Electrodes for RF Coagulation of Atrial Tissue" Proccedings 19th International Conference—IEEE/EMBS Oct. 30-Nov. 2, 1997 Chicago, Il. USA. pp. 2528-2530.

* cited by examiner

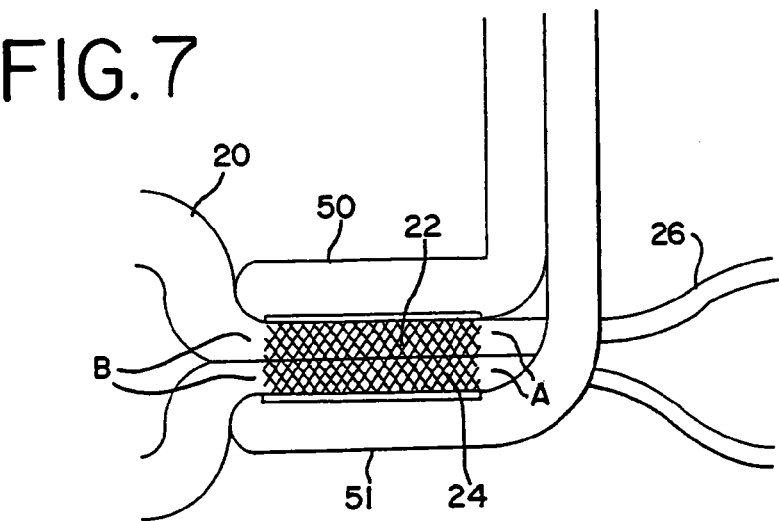
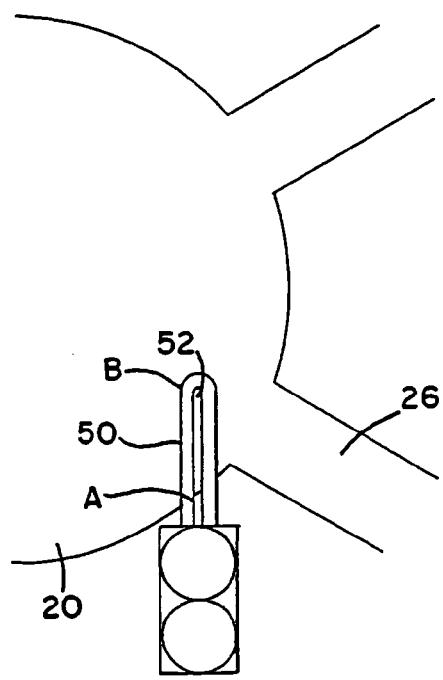
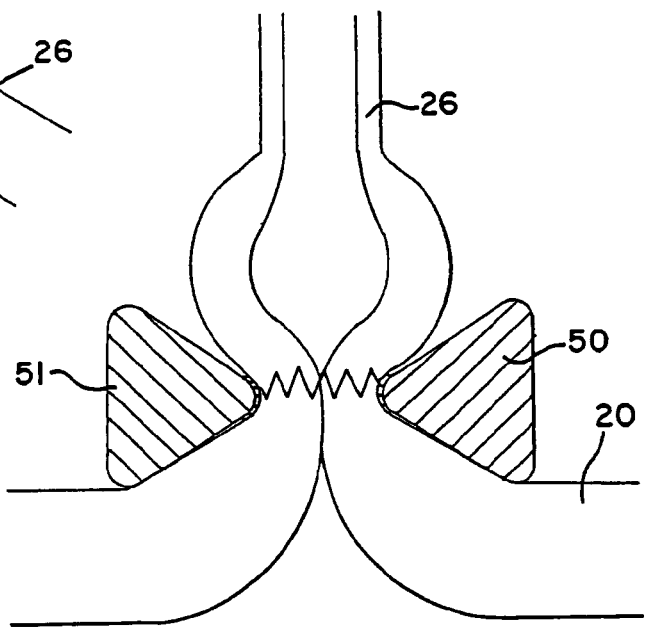

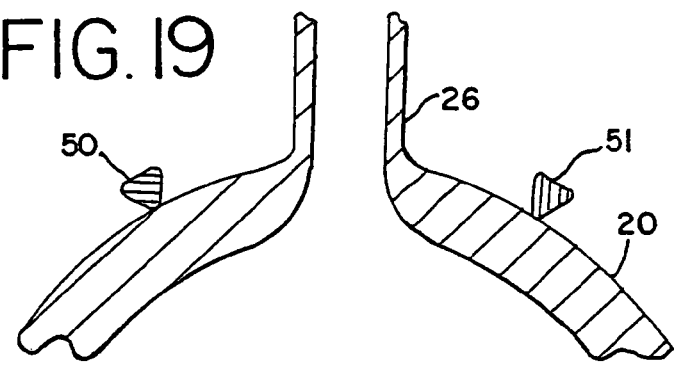
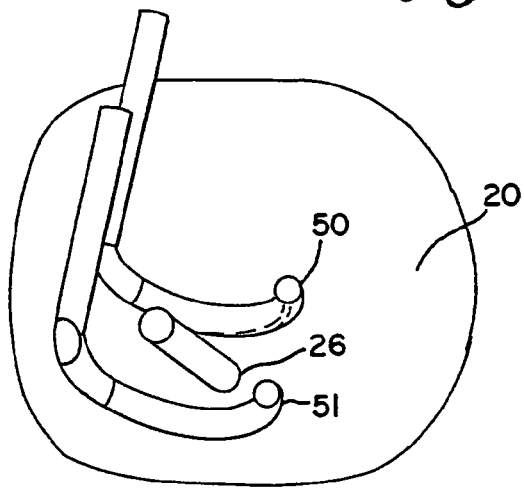
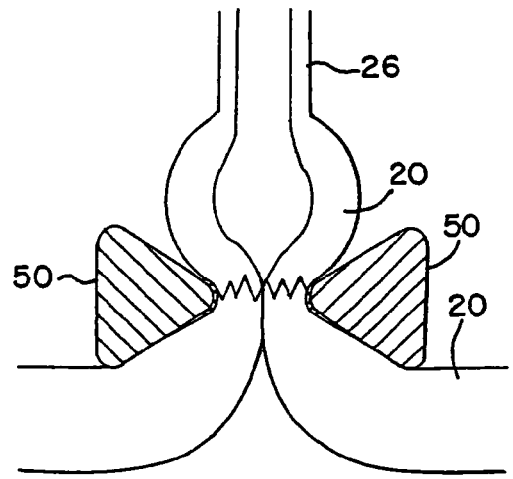
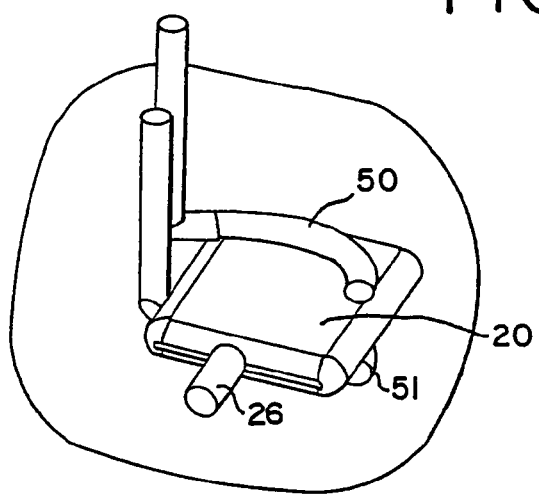
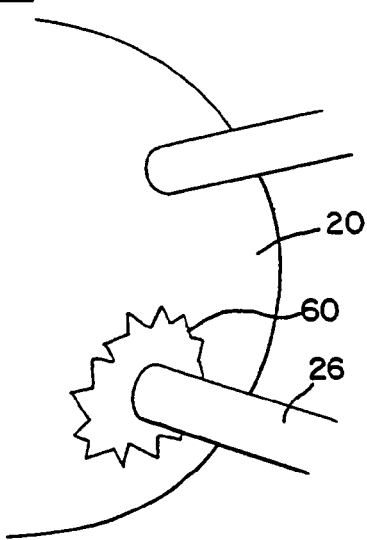

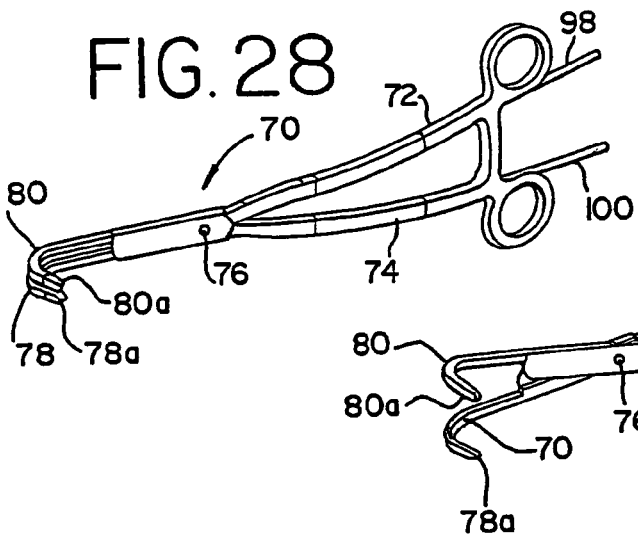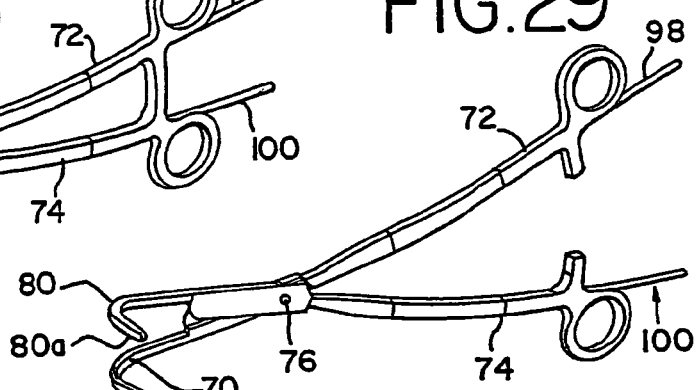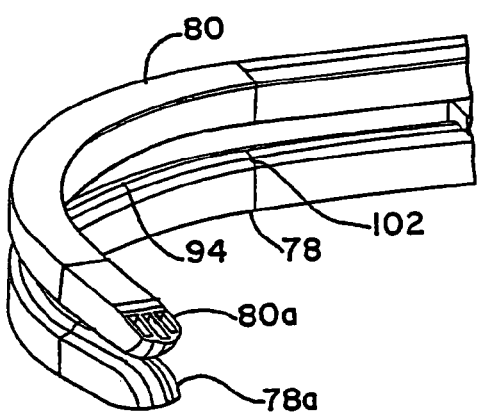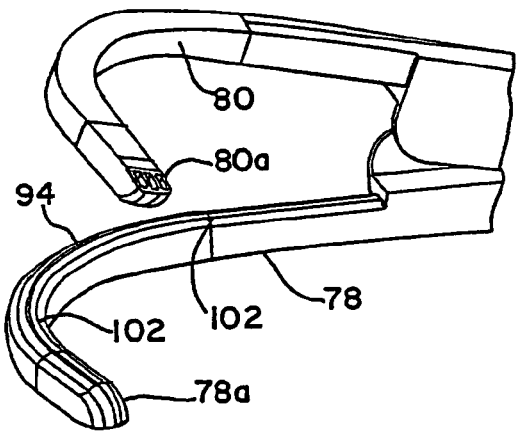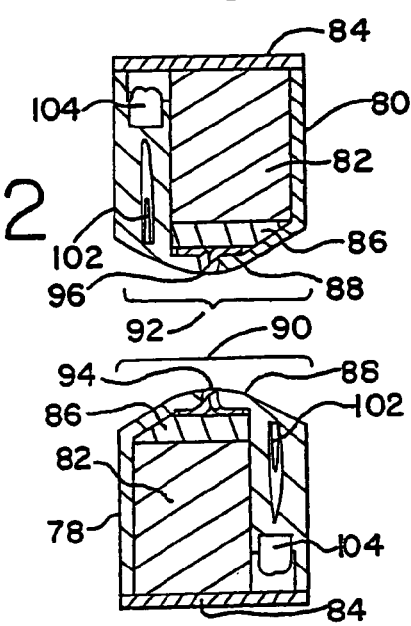

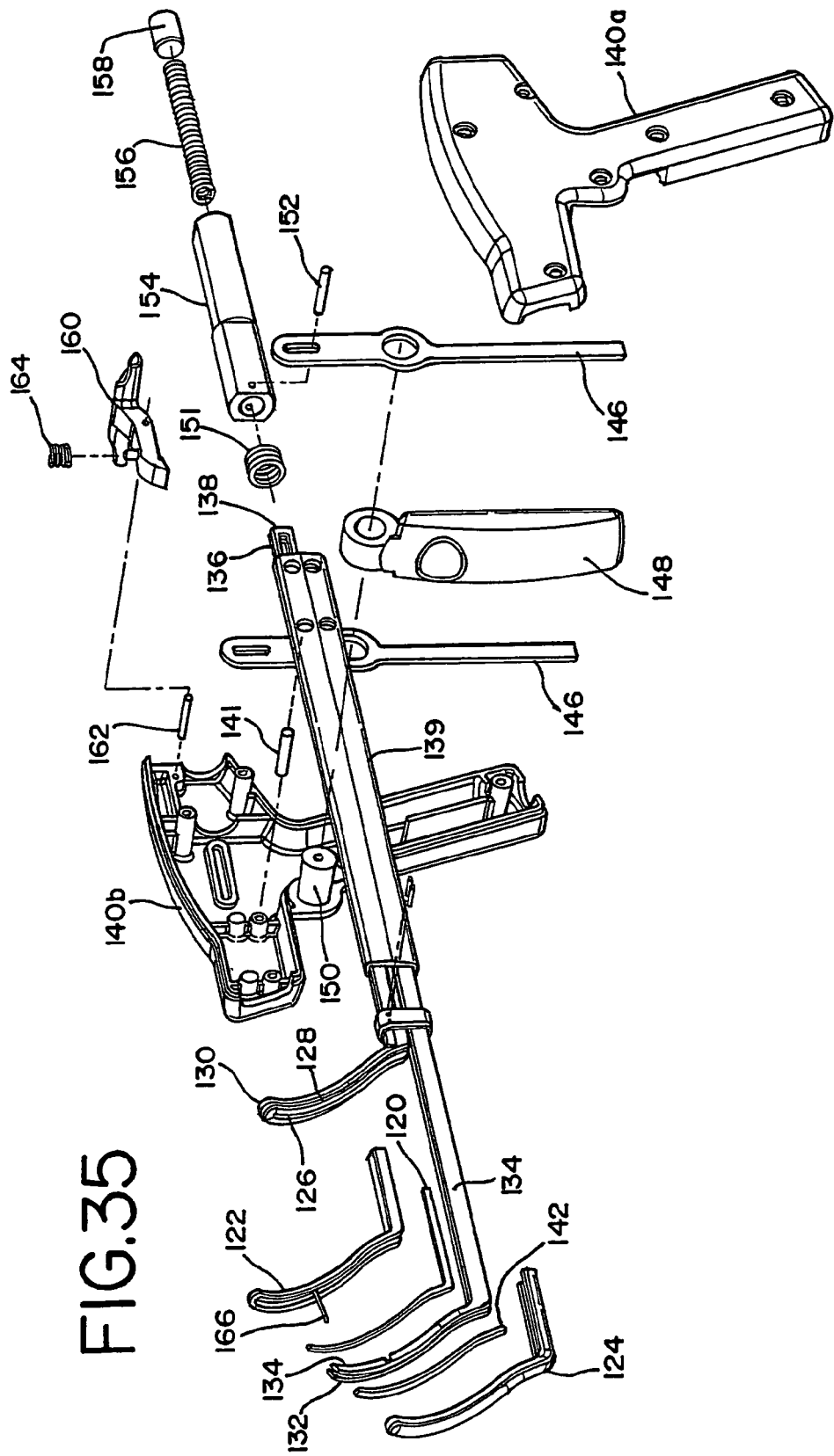

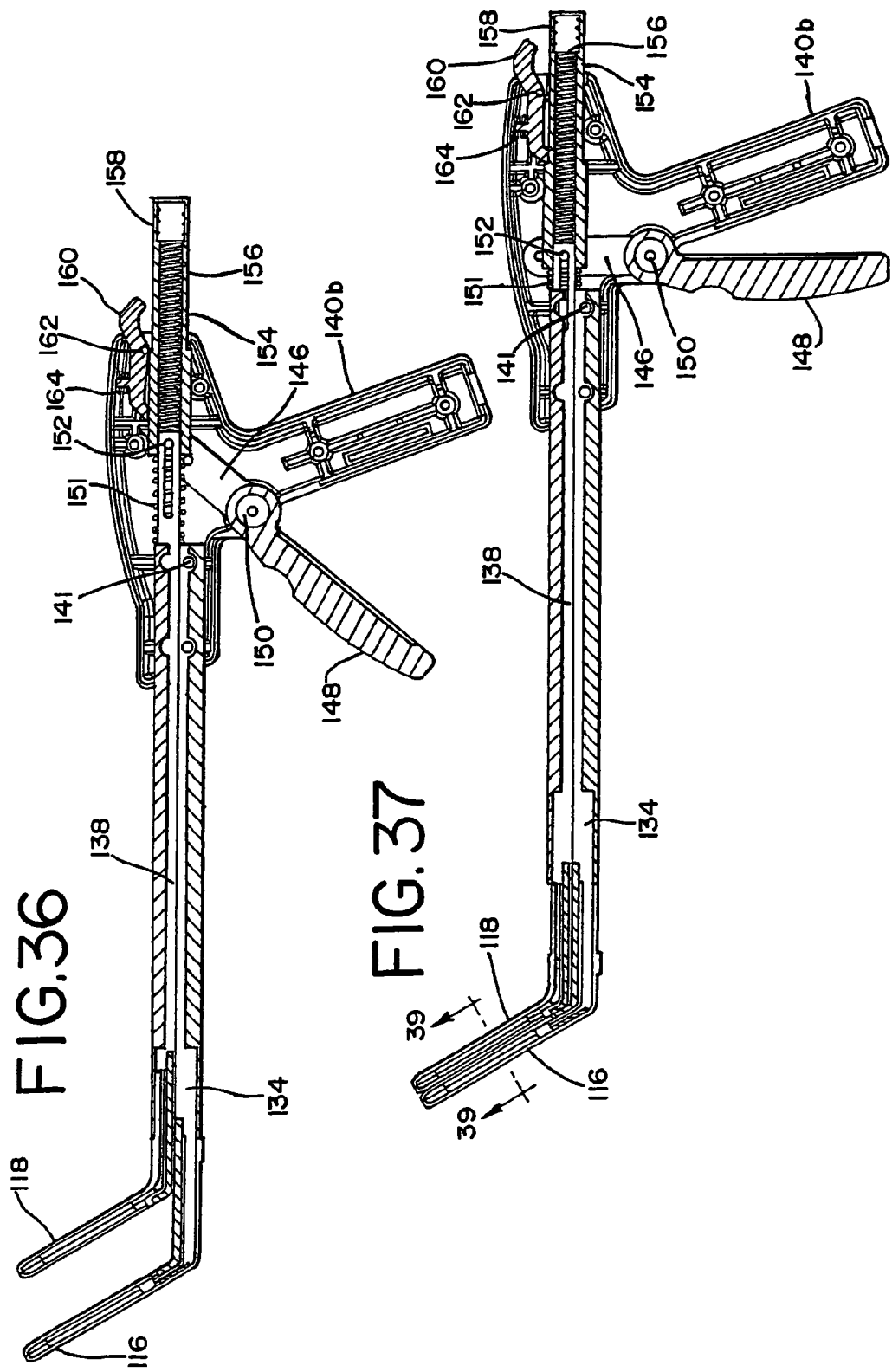

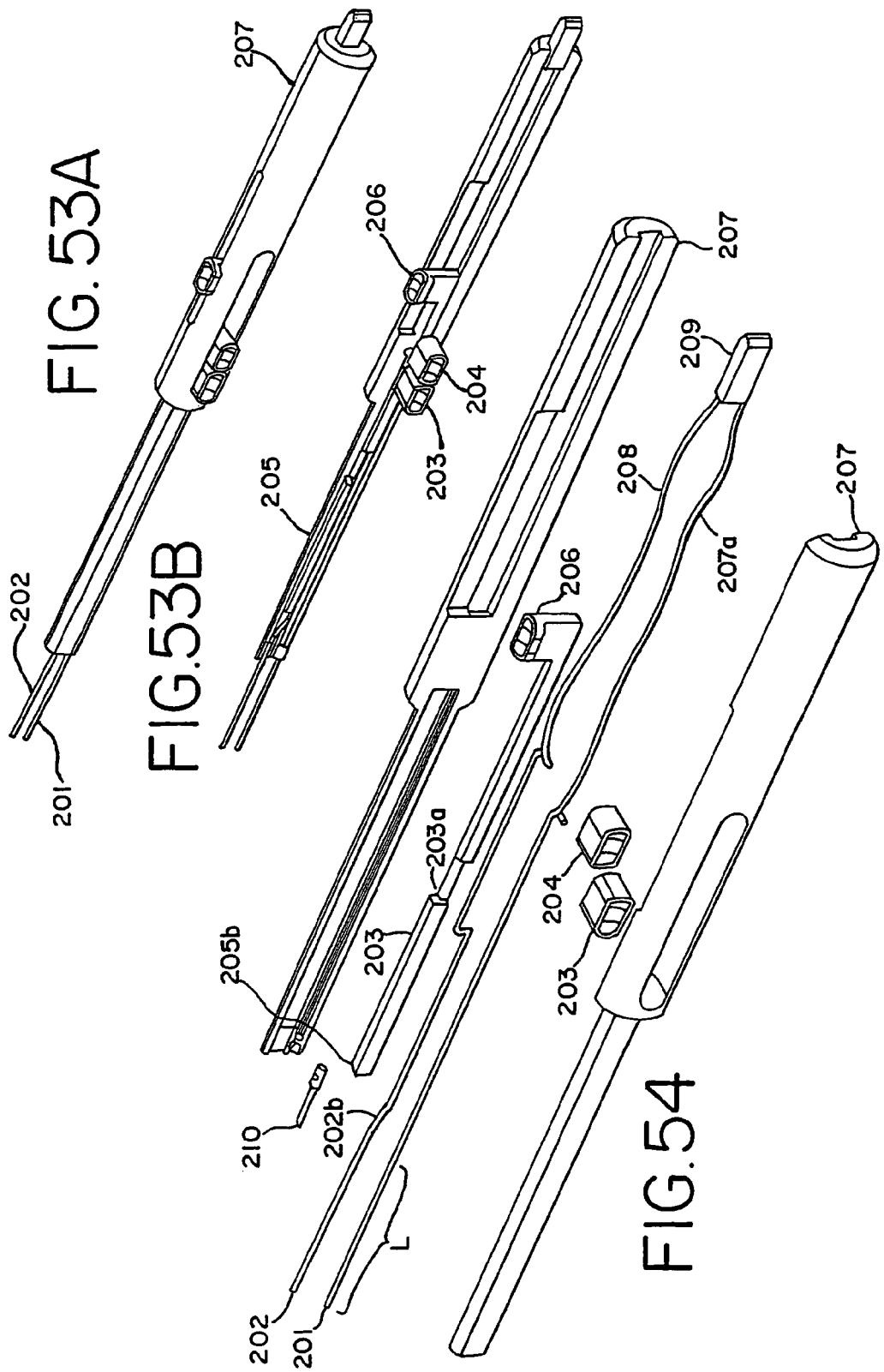

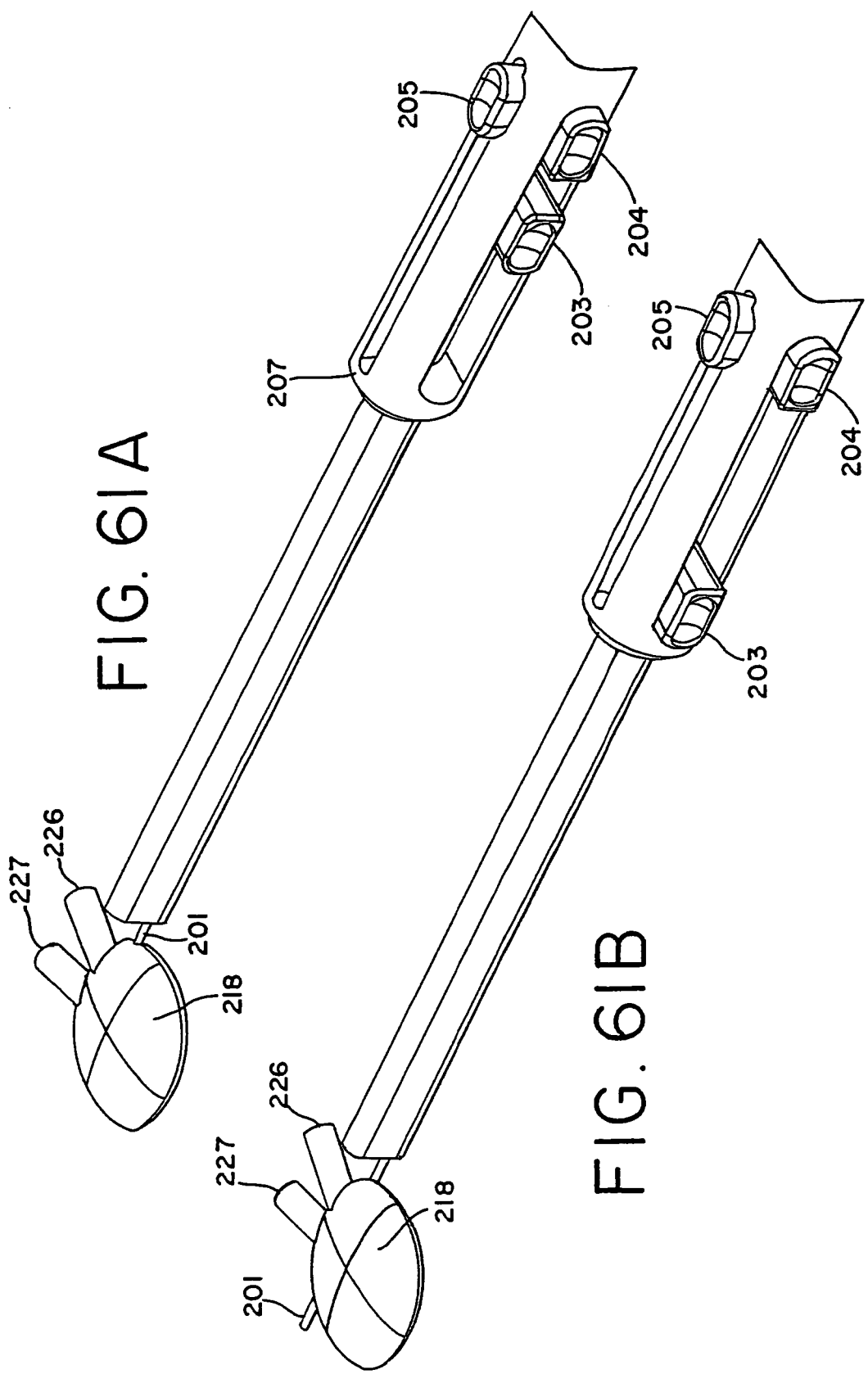

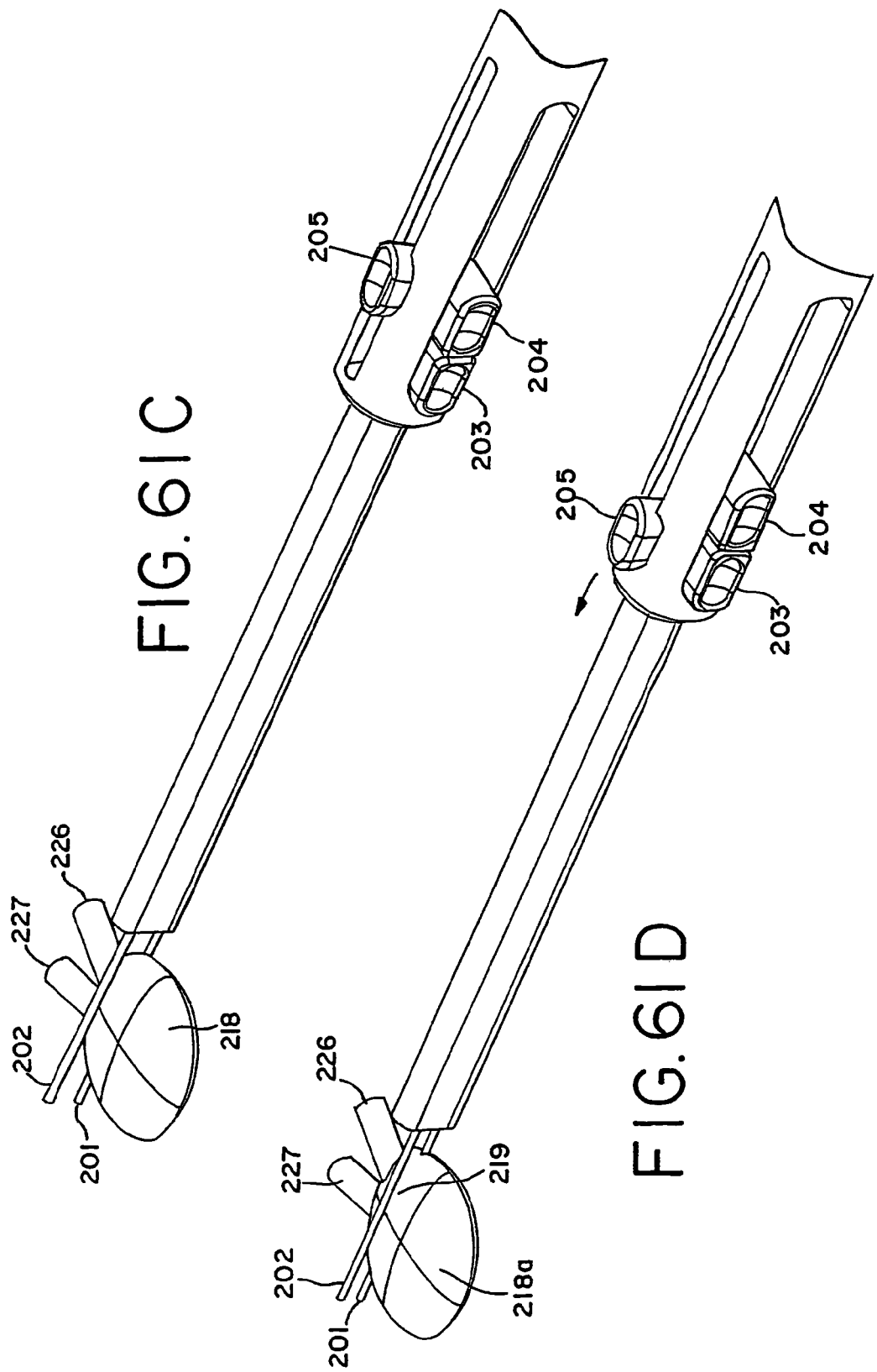

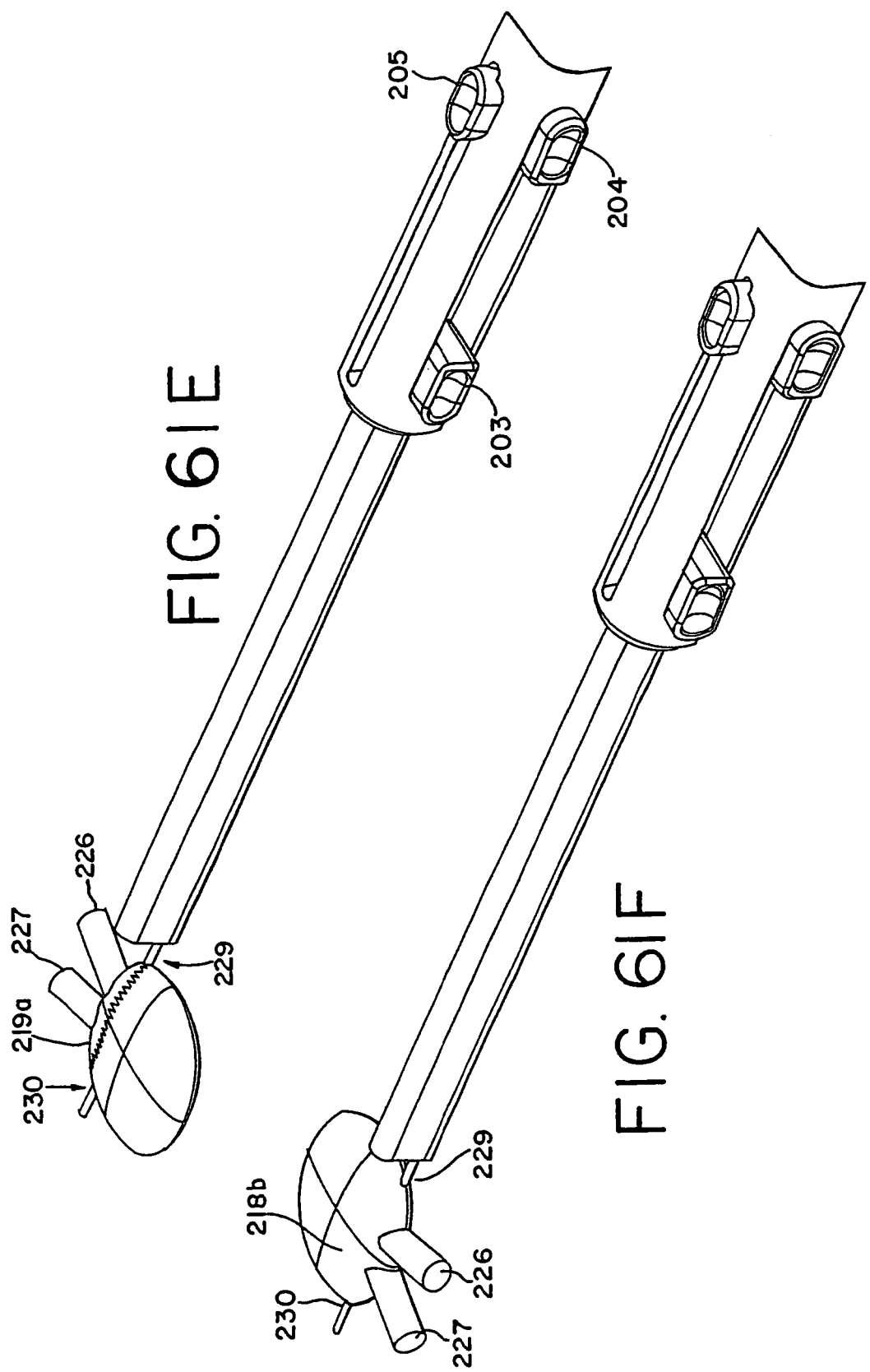

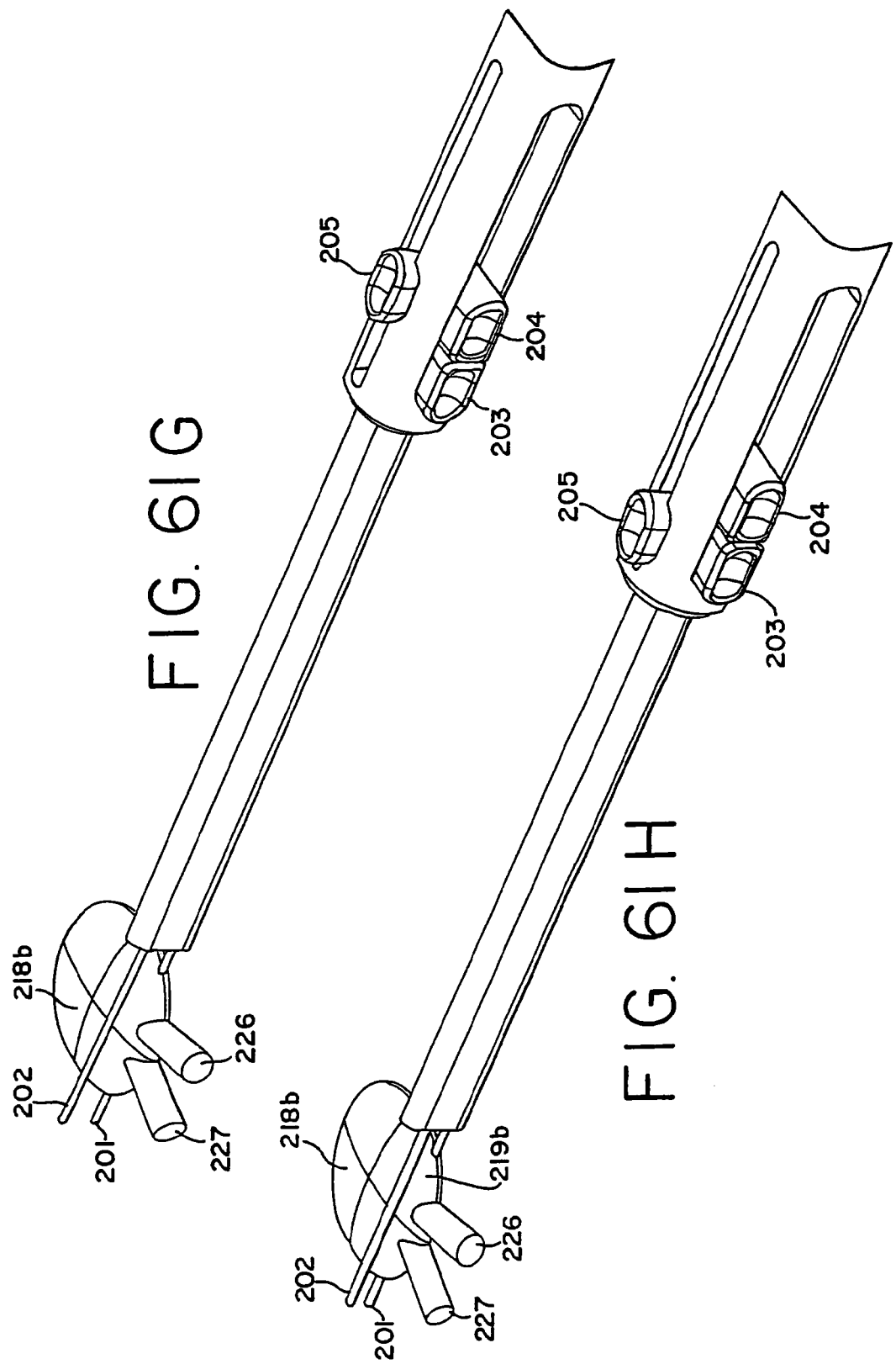

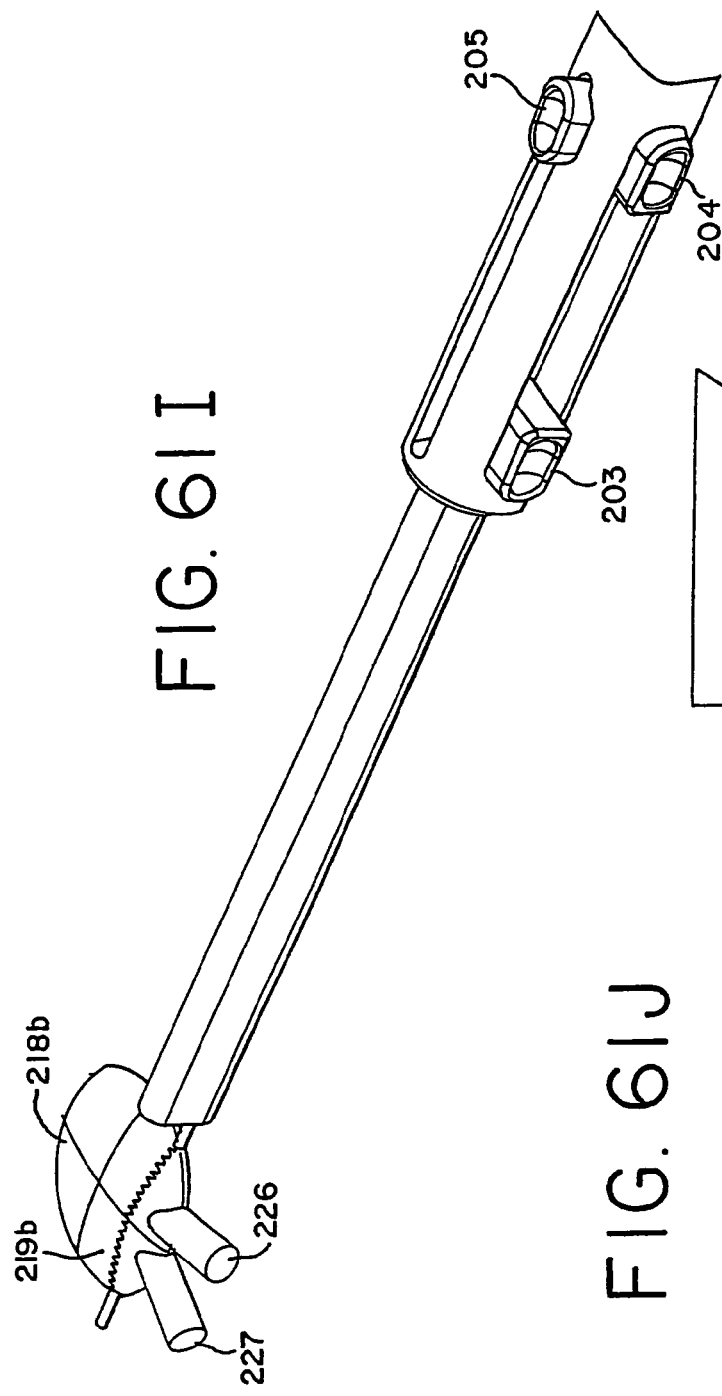
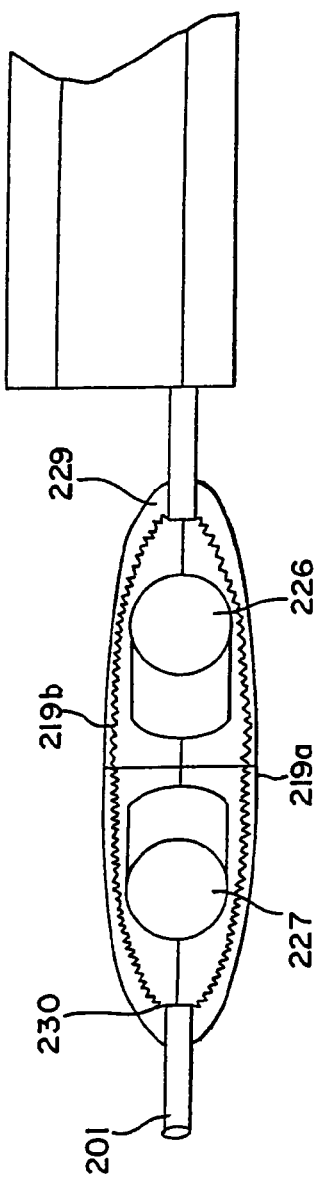
FIG. 61I
FIG. 61J

RECEIVER

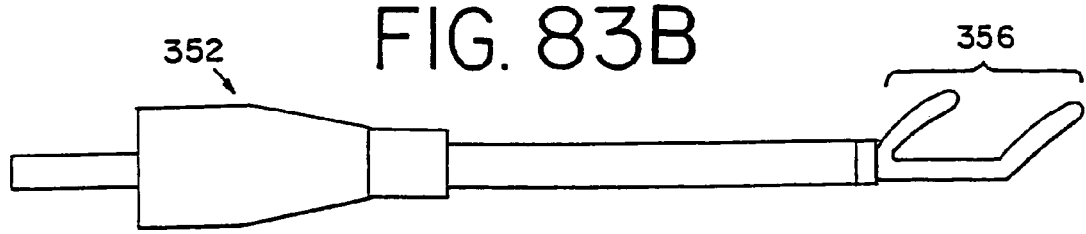
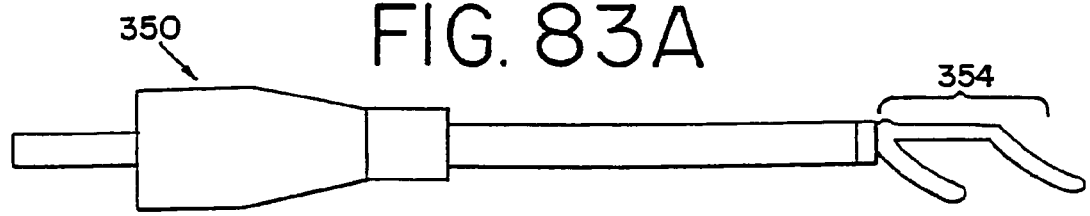
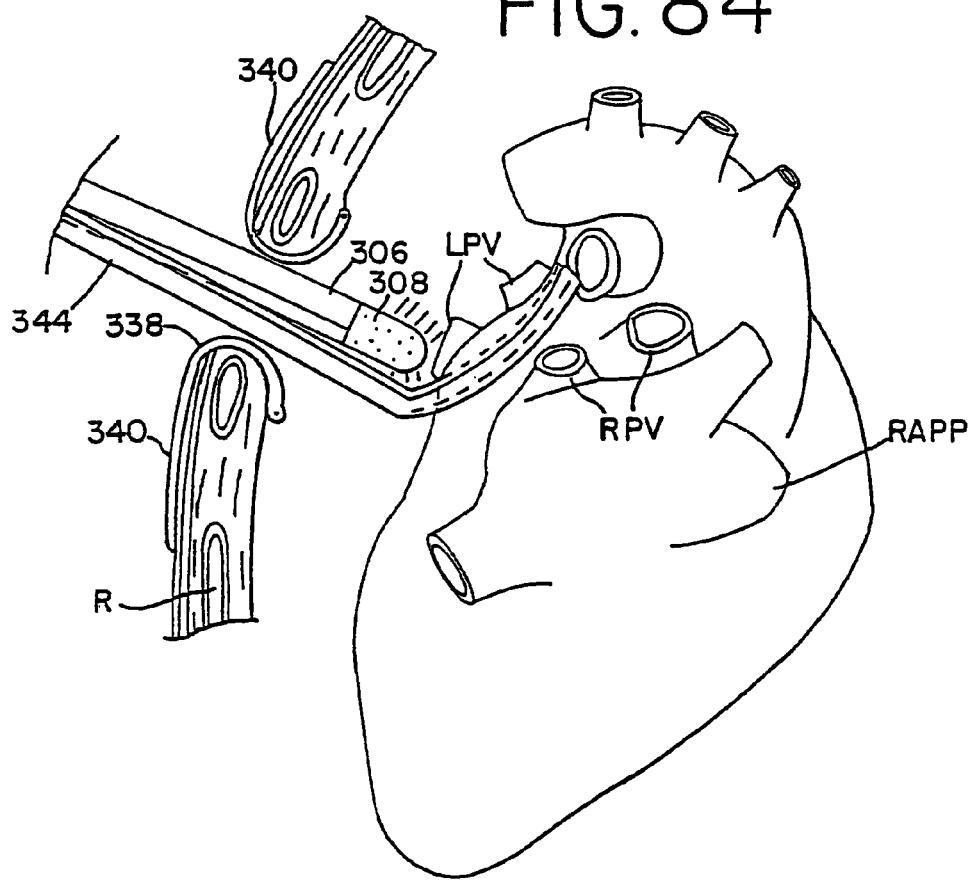

TRANSMURAL ABLATION DEVICE

CROSS REFERENCE TO RELATED APPLICATION

This application is a division of application Ser. No. 10/038,506, filed Nov. 9, 2001, which is a continuation-in-part of application Ser. No. 10/032,378, filed Oct. 26, 2001, now U.S. Pat. No. 6,932,811 which is a continuation-in-part of application Ser. No. 09/844,225 filed Apr. 27, 2001, now U.S. Pat. No. 6,517,536 which is a continuation-in-part of application Ser. No. 09/747,609 Dec. 22, 2000, now U.S. Pat. No. 6,546,935 which claims the benefit of provisional application Ser. No. 60/200,072, filed Apr. 27, 2000.

BACKGROUND OF THE INVENTION

Atrial fibrillation is the most common heart arrhythmia in the world, affecting over 2.5 million people in the United States alone. Ablation of cardiac tissue, in order to create scar tissue that poses an interruption in the path of the errant electrical impulses in the heart tissue, is a commonly performed procedure to treat cardiac arrhythmias. Such ablation may range from the ablation of a small area of heart tissue to a series of ablations forming a strategic placement of incisions in both atria to stop the conduction and formation of errant impulses.

Ablation has been achieved or suggested using a variety of techniques, such as freezing via cryogenic probe, heating via RF energy, surgical cutting and other techniques. As used here, "ablation" means the removal or destruction of the function of a body part, such as cardiac tissue, regardless of the apparatus or process used to carry out the ablation. Also, as used herein, "transmural" means through the wall or thickness, such as through the wall or thickness of a hollow organ or vessel.

Ablation of cardiac tissue may be carried out in an open surgical procedure, where the breastbone is divided and the surgeon has direct access to the heart, or through a minimally invasive route, such as between the ribs or via catheter that is introduced through a vein, and into the heart.

Prior to any ablation, the heart typically is electronically mapped to locate the point or points of tissue which are causing the arrhythmia. With minimally invasive procedures such as via a catheter, the catheter is directed to the aberrant tissue, and an electrode or cryogenic probe is placed in contact with the endocardial tissue. RF energy is delivered from the electrode to the tissue to heat and ablate the tissue (or the tissue may be frozen by the cryogenic probe), thus eliminating the source of the arrhythmia.

Common problems encountered in this procedure are difficulty in precisely locating the aberrant tissue, and complications related to the ablation of the tissue. Locating the area of tissue causing the arrhythmia often involves several hours of electrically "mapping" the inner surface of the heart using a variety of mapping catheters, and once the aberrant tissue is located, it is often difficult to position the catheter and the associated electrode or probe so that it is in contact with the desired tissue.

The application of either RF energy or ultra-low temperature freezing to the inside of the heart chamber also carries several risks and difficulties. It is very difficult to determine how much of the catheter electrode or cryogenic probe surface is in contact with the tissue since catheter electrodes and probes are cylindrical and the heart tissue cannot be visualized clearly with existing fluoroscopic technology. Further, because of the cylindrical shape, some of the exposed electrode or probe area will almost always be in contact with blood circulating in the heart, giving rise to a risk of clot formation.

Clot formation is almost always associated with RF energy or cryogenic delivery inside the heart because it is difficult to prevent the blood from being exposed to the electrode or probe surface. Some of the RF current flows through the blood between the electrode and the heart tissue and this blood is coagulated, or frozen when a cryogenic probe is used, possibly resulting in clot formation. When RF energy is applied, the temperature of the electrode is typically monitored so as to not exceed a preset level, but temperatures necessary to achieve tissue ablation almost always result in blood coagulum forming on the electrode.

Overheating or overcooling of tissue is also a major complication, because the temperature monitoring only gives the temperature of the electrode or probe, which is, respectively, being cooled or warmed on the outside by blood flow. The actual temperature of the tissue being ablated by the electrode or probe is usually considerably higher or lower than the electrode or probe temperature, and this can result in overheating, or even charring, of the tissue in the case of an RF electrode, or freezing of too much tissue by a cryogenic probe. Overheated or charred tissue can act as a locus for thrombus and clot formation, and over freezing can destroy more tissue than necessary.

It is also very difficult to achieve ablation of tissue deep within the heart wall. A recent study reported that to achieve a depth of ablation of 5 mm, it was necessary to ablate an area almost 8 mm wide in the endocardium. See, "Mechanism, Localization, and Cure of Atrial Arrhythmias Occurring After a New Intraoperative Endocardial Radiofrequency Ablation Procedure for Atrial Fibrillation," Thomas, et al., *J. Am. Coll. Cardiology*, Vol. 35, No. 2, 2000. As the depth of penetration increases, the time, power, and temperature requirements increase, thus increasing the risk of thrombus formation.

In certain applications, it is desired to obtain a continuous line of ablated tissue in the endocardium. Using a discrete or point electrode or probe, the catheter must be "dragged" from point to point to create a line, and frequently the line is not continuous. Multielectrode catheters have been developed which can be left in place, but continuity can still be difficult to achieve, and the lesions created can be quite wide.

Because of the risks of char and thrombus formation, RF energy, or any form of endocardial ablation, is rarely used on the left side of the heart, where a clot could cause a serious problem (e.g., stroke). Because of the physiology of the heart, it is also difficult to access certain areas of the left atrium via an endocardial, catheter-based approach.

Recently, epicardial ablation devices have been developed which apply RF energy to the outer wall of the heart to ablate tissue. These devices do not have the same risks concerning thrombus formation. However, it is still difficult to create long, continuous lesions, and it is difficult to achieve good depth of penetration without creating a large area of ablated tissue.

As noted above, other forms of energy have been used in ablation procedures, including ultrasound, cryogenic ablation, and microwave technology. When used from an endocardial approach, the limitations of all energy-based ablation technologies to date are the difficulty in achieving continuous transmural lesions, and minimizing unnecessary damage to endocardial tissue. Ultrasonic and RF energy endocardial balloon technology has been developed to create circumferential lesions around the individual pulmonary veins. See e.g., U.S. Pat. No. 6,024,740 to Lesh et al. and U.S. Pat. Nos. 5,938,660 and 5,814,028 to Swartz et al. However, this technology creates rather wide (greater than 5 mm) lesions which could lead to stenosis (narrowing) of the pulmonary veins. See, "Pulmonary Vein Stenosis after Catheter Ablation of Atrial Fibrillation," Robbins, et al., *Circulation,* Vol. 98, pages 1769–1775, 1998. The large lesion area can also act as a locus point for thrombus formation. Additionally, there is no feedback to determine when full transmural ablation has been achieved. Cryogenic ablation has been attempted both endocardially and epicardially (see e.g., U.S. Pat. No. 5,733,280 to Avitall, U.S. Pat. No. 5,147,355 to Friedman et al., and U.S. Pat. No. 5,423,807 to Milder, and WO 98/17187, the latter disclosing an angled cryogenic probe, one arm of which is inserted into the interior of the heart through an opening in the heart wall that is hemostatically sealed around the arm by means of a suture or staples), but because of the time required to freeze tissue, and the delivery systems used, it is difficult to create a continuous line, and uniform transmurality is difficult to verify.

Published PCT applications WO 99/56644 and WO 99/56648 disclose an endocardial ablation catheter with a reference plate located on the epicardium to act as an indifferent electrode or backplate that is maintained at the reference level of the generator. Current flows either between the electrodes located on the catheter, or between the electrodes and the reference plate. It is important to note that this reference plate is essentially a monopolar reference pad. Consequently, there is no energy delivered at the backplate/tissue interface intended to ablate tissue. Instead, the energy is delivered at the electrode/tissue interface within the endocardium, and travels through the heart tissue either to another endocardial electrode, or to the backplate. Tissue ablation proceeds from the electrodes in contact with the endocardium outward to the epicardium. Other references disclose epicardial multielectrode devices that deliver either monopolar or bipolar energy to the outside surface of the heart.

It is important to note that all endocardial ablation devices that attempt to ablate tissue through the full thickness of the cardiac wall have a risk associated with damaging structures within or on the outer surface of the cardiac wall. As an example, if a catheter is delivering energy from the inside of the atrium to the outside, and a coronary artery, the esophagus, or other critical structure is in contact with the atrial wall, the structure can be damaged by the transfer of energy from within the heart to the structure. The coronary arteries, esophagus, aorta, pulmonary veins, and pulmonary artery are all structures that are in contact with the outer wall of the atrium, and could be damaged by energy transmitted through the atrial wall.

Accordingly, it is the object of the present invention to provide an improved method and device for making transmural ablations to heart tissue.

It is a related object to provide a method and device for making transmural ablation in heart tissue that minimizes unnecessary damage to the heart tissue.

It is a further object to provide a method and device for making transmural ablation in heart tissue that creates continuous lesions in a single step.

SUMMARY OF THE INVENTION

These objects, and others which will become apparent upon reference to the following detailed description and attached drawings, are achieved by the use of a clamping and ablating device for use in treating cardiac arrhythmia having first and second handle members, with first and second mating jaw members associated with the first and second handle members. The jaw members are movable by the handle members between a first open position and a second clamped position, and the jaw members have opposed mating surfaces. An elongated electrode extends along the mating surface of each jaw. The electrodes are adapted to be connected to an RF energy source so that, when activated, the electrodes are of opposite polarity. In a preferred embodiment, the electrodes are made of gold-plated copper and measure between approximately 3 to 8 cm in length and approximately 0.12 to 0.6 mm in width.

BRIEF DESCRIPTION OF THE DRAWINGS

FIG. 7 shows a further step in the inventive procedure in which tissue is clamped between the ablation elements.

FIGS. 8–12 schematically illustrate the inventive procedure so as to make a transmural lesion that fully circumscribes a pulmonary vein, with FIG. 9 showing a cross-sectional view of the clamp/ablation element in contact with the atrial tissue to express blood from the clamped area.

FIGS. 18–22 show a further procedure in which a transmural lesion is made so as to circumscribe a single pulmonary vein.

FIG. 28 is a perspective view of a further embodiment of a grasper for use in an open chest procedure in accordance with the present invention showing the grasper in its "closed" position.

FIG. 29 is a perspective view of the grasper of FIG. 28 with the grasper in its "open" position.

FIG. 30 is an enlarged perspective view of the working position of the grasper of FIG. 28 with the grasper jaws in the "closed" position.

FIG. 31 is an enlarged perspective view of the working portion of the grasper of FIG. 28 with the grasper jaws in the "open" position.

FIG. 32 is an enlarged cross-sectional view of the grasper jaws for the grasper of FIG. 28.

FIG. 35 is an exploded perspective view of the grasper of FIG. 33.

FIG. 36 is a side cross-sectional view of the grasper of FIG. 33 with the grasper jaws in the "open" position.

FIG. 37 is a side cross-sectional view of the grasper of FIG. 33 with the grasper jaws in the "closed" position.

FIG. 53A is a perspective view of a further embodiment of device for performing transmural ablation according to the present invention.

FIG. 53B is a perspective view of the transmural ablation device of FIG. 53A with a portion removed to show detail.

FIG. 54 is an exploded perspective view of the transmural ablation device of FIG. 52.

FIG. 61A–61J show the use of the instrument of FIG. 52 for forming a continuous transmural ablation around a pair of pulmonary veins.

FIG. 83A is a plan view of a cardiac grasper similar to the grasper shown in FIGS. 33–37 with right curved jaw members.

FIG. 83B is a plan view of a cardiac grasper similar to the grasper shown in FIGS. 33–37 with left curved jaw members.

FIG. 84 is a sectional view along plan 84—84 of FIG. 83 with portions of the patient's body removed.

DETAILED DESCRIPTION OF THE PREFERRED EMBODIMENTS

With reference to the present invention, the compression of the atrial tissue is important because it insures that the exposed electrode surface or cryogenic probe is not in contact with any tissue or blood except the clamped tissue to be ablated. Specifically, the clamping of the tissue between the electrodes or cryogenic probes insures that the conductive or cooled area is only in contact with the clamped tissue. The compressed tissue acts to isolate the electrically active or cryogenically cooled surface, and prevents inadvertent energy delivery to other parts of the heart or blood. The outside temperature of the electrode can easily be monitored to insure that the temperature of the insulation in contact with blood remains below a critical temperature (40° C., for example).

In one form of the invention, transmural ablation using RF energy is accomplished by providing an atrial ablation device having a lower "j" clamp/electrode element and placing it on the atrial tissue below the pulmonary veins.

Once the pulmonary veins have been isolated, an upper clamp/electrode element is introduced, and the clamp assembly "J" is worked back onto the epicardial atrial tissue. Once the jaws are positioned below the ostia of the pulmonary veins, the tissue is partially clamped, allowing continued flow from the pulmonary veins to the left atrium. Once the clamps are safely away from the pulmonary vein tissue, and onto atrial tissue, the clamps are closed together to compress the tissue. Once the tissue is compressed, bipolar RF energy is used to ablate the clamped atrial tissue. The clamps are then removed, the lesion having been created. Lesions may also be created by inserting one clamp/electrode element through an incision in the heart so as to permit contact with endocardial tissue. This incision may be created with a separate instrument. Alternatively, the tip of one of the jaws may have a piercing structure associated therewith for making the entry incision. Once the clamps are properly located, the tissue is compressed and RF energy is applied.

Figure 1:
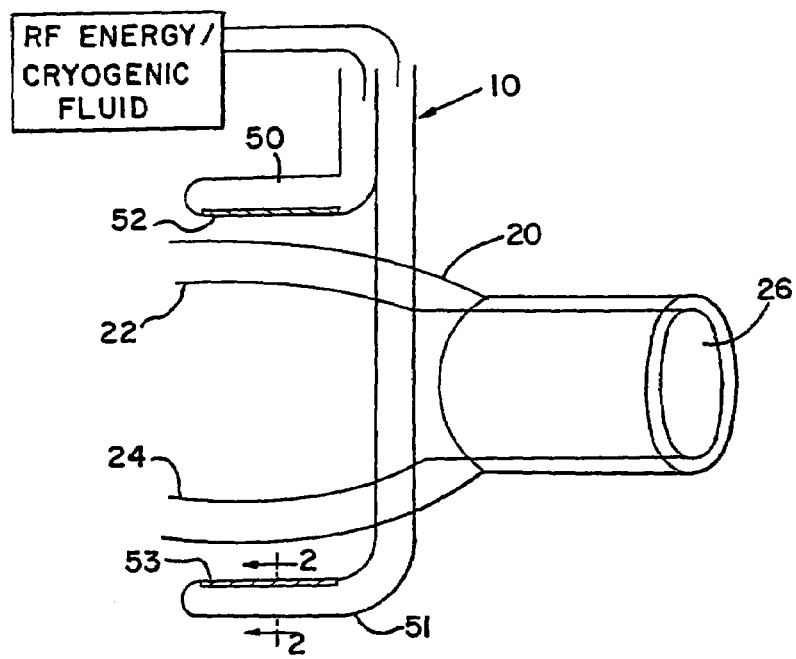
FIG. 1 is a schematic view showing a procedure in accordance with the present invention utilizing ablation elements operatively connected to either a source of RF energy or cryogenic fluid.
Figure 2:
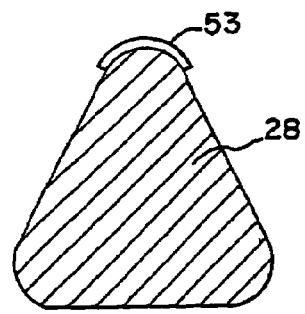
FIG. 2 is a cross-section of an ablation element for use in the present invention taken along lines 2—2 of FIG. 1.
Figure 3:
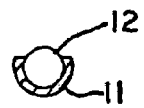
FIGS. 3–6 show alternate configurations for the ablation elements of FIG. 2.

Turning now to the figures of the drawings, a method embodying the present invention is shown schematically in FIG. 1. A clamping type device 10 is provided to group the two walls 22, 24 of the atrium 20, and delivers bipolar RF energy through both walls held between the two upper and lower clamp jaws 50, 51. FIG. 1 shows the upper and lower parallel clamp jaws 50, 51 and electrodes 52, 53 positioned above and below atrial tissue 22, 24, distal to the pulmonary veins. FIG. 2, Section 2—2 of FIG. 1, shows a cross-section of the clamping member including the insulator 28 and electrode 53. Alternate configurations of the clamping members are shown in FIGS. 3–6. FIG. 3 shows a cross section of the electrode consisting of an insulating layer 11, and a conductive strip 12. The electrode of FIG. 3 may be constructed of a tungsten wire as the conductive material 12, with polyamide as the insulating material 11. The conductive strip is created by exposing a part of the tungsten wire through the polyamide.

Figure 4:
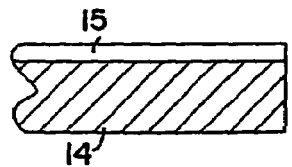
Figure 5:
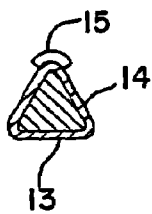
Figure 6:
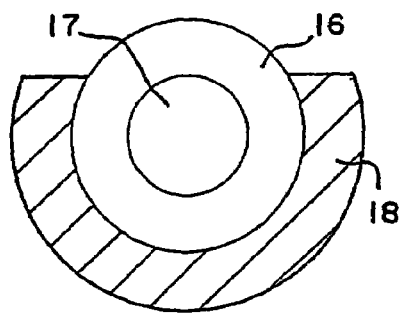
Figure 10:
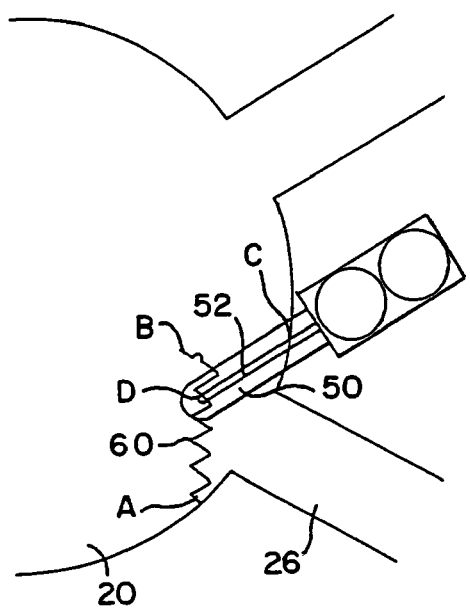

FIGS. 4 and 5 show an alternate electrode construction consisting of a carbon fiber element 13, and an insulating material 14, such as ABS. The conductive strip 15 may be comprised of a copper/gold electrode plated onto the ABS. FIG. 6 shows a cross section of yet another possible electrode design where the conductive material 16 consists of a stainless steel needle with lumen 17 and insulating material 18.

FIG. 7 shows the parallel jaws 50, 51 clamping and ablating the atrial tissue 20 distal to the pulmonary veins 26. Proximal point A is clamping and ablating the atrial tissue distal to the pulmonary veins. Proximal point A is the most proximal point of ablated tissue on both the upper and lower atrial wall. Distal point B is the most distal point of ablated tissue on both the upper and lower atrial wall.

FIGS. 8–12 show the inventive procedure that fully circumscribes a pulmonary vein with transmural lesions. FIG. 8 shows a top view of the instrument jaws positioned for a 2-step isolation of a single pulmonary vein. The lower jaw is directly beneath the upper jaw, and is not shown. Proximal point A and distal point B correspond to FIG. 7.

Figure 26:
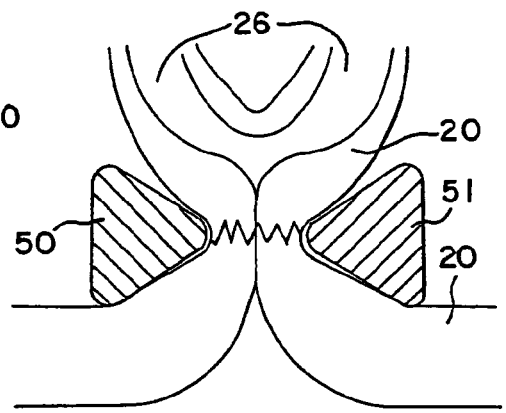
Figure 27:
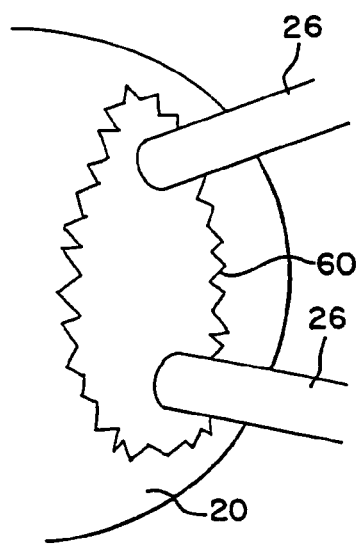

FIG. 9 shows a cross-sectional view of the jaws clamping and ablating atrial tissue. Importantly, FIG. 9 shows that the electrode/clamp configuration provides a clamped zone of tissue that is wider than the zone of ablated tissue. This is achieved by using an electrode width that is narrower than the clamped tissue width, and preferably less than one-third of the clamped tissue width. As shown in FIG. 9 (and better illustrated in FIG. 26), the electrode forms the apex of the triangular clamping member. Other convex shapes are also contemplated.

The wider zone of clamped tissue serves several purposes. When the clamping members are closed onto tissue, any blood in the clamped zone is squeezed or expressed out. Further, the distance between the electrodes is minimized, so that the ablation zone remains narrow. It is important to isolate the blood from the ablation zone to avoid creating thrombus. Accordingly, a clamped zone that isolates the ablation zone from the blood minimizes the temperature at the periphery of the ablation zone and will reduce the likelihood of the formation of thrombus by the blood in contact with the clamped zone.

Figure 11:
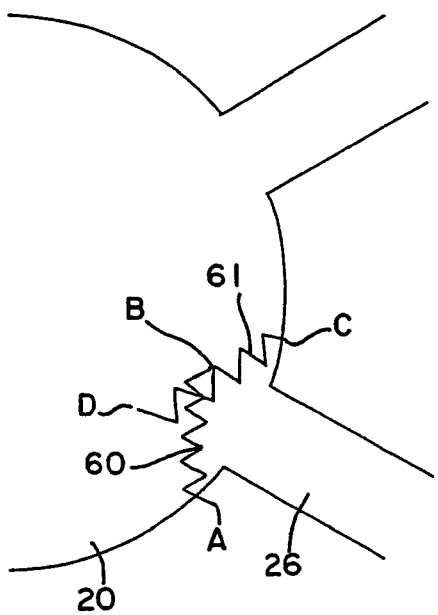
Figure 12:
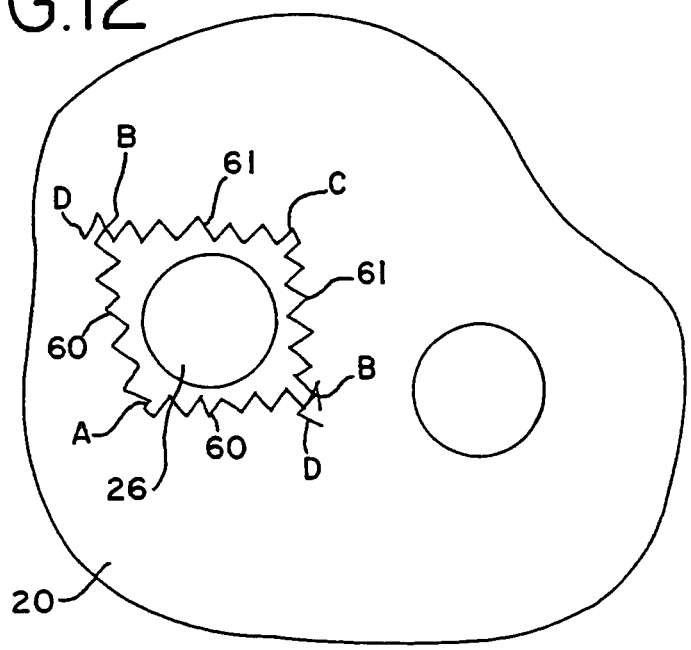
Figure 13:
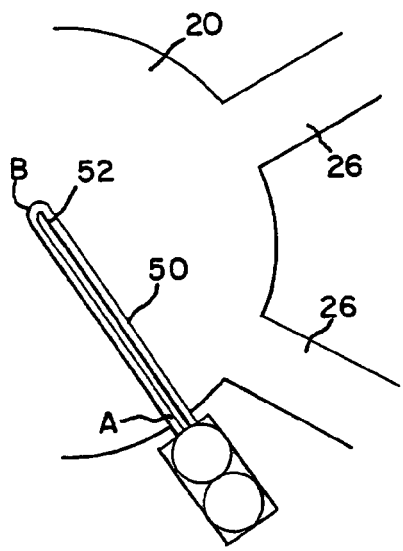
FIGS. 13–17 show a further method according to the present invention in which transmural lesions are made so as to circumscribe both pulmonary veins.
Figure 14:
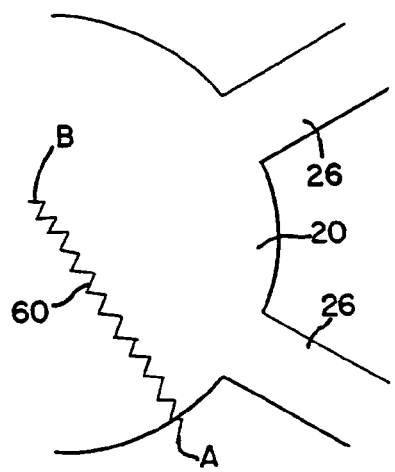
Figure 16:
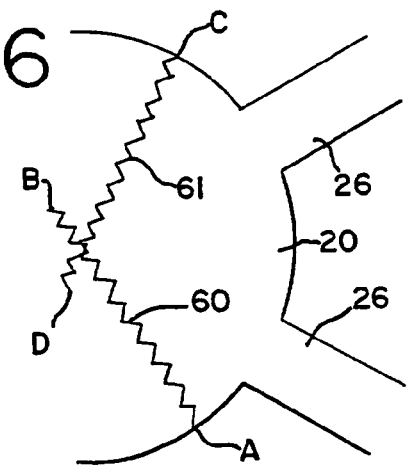
Figure 15:
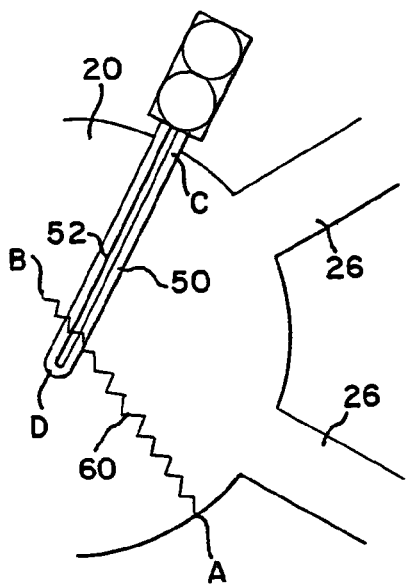
Figure 17:
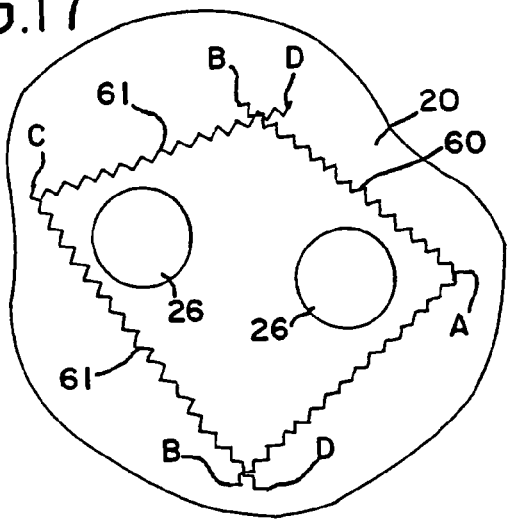
Figure 23:
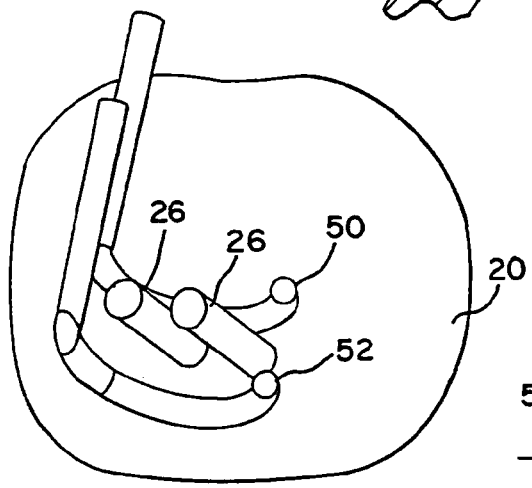
FIGS. 23–27 illustrate a further procedure in which a transmural lesion is made so as to circumscribe both pulmonary veins.
Figure 24:
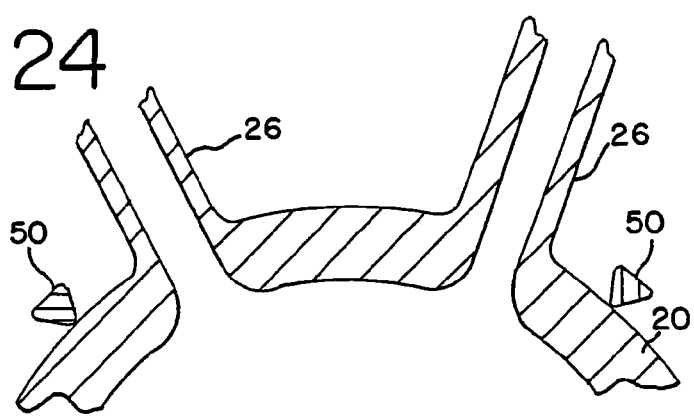
Figure 25:
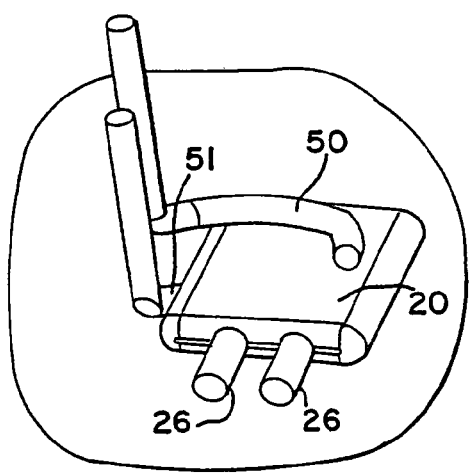

Once tissue has been fully ablated with the clamp in the position shown in FIG. 8, an ablation line of tissue on both upper and lower atrial walls is created. This is shown as ablation line 60 in FIG. 10. The clamp is then repositioned to the position shown in FIG. 10, so that the distal point D overlaps the ablation line 60. The tissue is clamped and ablated as shown in FIGS. 7 and 9, and a second ablation line 61 (FIG. 11) is formed on both the upper and lower atrial walls. Proximal point C and distal point D correspond to points A and B respectively. The full ablation line is shown in FIGS. 11 and 12 with points A–D as shown.

This "clamping" method and device for creating transmural lesions has a number of advantages. First, using a two step method as shown allows for clamping and ablation of atrial tissue without stopping the blood flow from the pulmonary vein. Secondly, by clamping both walls together, and delivering energy through the clamped tissue, the atrial tissue is not penetrated. Because the atrial tissue is not penetrated, a larger jaw can be used, and the clamping force can be much higher because of the increased stiffness of the jaw. Also, there is no concern of bleeding from an atrial puncture.

Another advantage of this method and device is that ablation of tissue within the pulmonary veins is avoided, as recent articles have shown that ablation of tissue within the pulmonary veins can cause pulmonary hypertension and stenosis. Specifically referring to FIGS. 13–17, a longer jaw could be used to create an ablation line through atrial tissue which electrically isolates both pulmonary veins using the same method.

FIGS. 18–22 show the clamping device in a curved-jaw embodiment that creates a circumferential lesion around the pulmonary vein in one step. FIGS. 18 and 19 show the clamp jaws positioned around the pulmonary vein. FIGS. 20 and 21 show the device clamping and ablating atrial tissue distal to the pulmonary vein. FIG. 22 shows the resulting ablation line 60.

FIGS. 23–27 show the same concept applied to a device and method for creating a lesion around both pulmonary veins. The advantage of this concept is that the entire lesion is created in one step. The disadvantage is that blood flow from the pulmonary vein(s) is cut off during ablation. Using a curved electrode also allows the user to ablate tissue more distal to the pulmonary vein than would be possible with a straight electrode. Note that this curved type electrode could be used with a two step procedure as described above, using "left" and "right" curved devices to create a lesion which was more distal to the pulmonary veins. Note also that this method and device are not limited to use around the pulmonary veins, but could be used anywhere in the atrium that the clamp could be applied.

Turning to FIGS. 28–32, there is seen a further version of a cardiac grasper 70 suitable for an open chest procedure in accordance with the present invention. The grasper 70 includes two ring handles 72, 74 joined together for relative movement by a pivot screw or pin 76. Each handle 72, 74 has a jaw member 78, 80 respectively associated therewith, each jaw being curved so that it has a major portion that is substantially perpendicular to the handles. This gives the grasper 70 an L-shaped appearance, with a working portion of the jaws being between approximately 3–8 cm in length.

The grasper is made of a rigid material, such as stainless steel, and is substantially encased in a durable insulating material, such as ABS plastic. With reference to FIG. 32, which shows the opposed jaw members in cross section, the stainless steel structural support is designated 82. The structural support 82 is completely encased by insulating members 84, 86 and 88. The tips 78a, 80a of the jaws may be made of a soft, atraumatic material in order to reduce the likelihood of unintentional injury of tissue by the jaws.

In keeping with the invention, the grasper jaws have raised or convex, opposed tissue clamping surfaces, 90, 92, respectively, with each clamping surface, 90, 92 centrally supporting an electrode 94, 96, respectively, of opposite polarity. The spacing between the jaws is substantially uniform or constant when in the closed or clamped position. RF energy of opposite polarity is supplied to the electrodes 94, 96 through conductors 98, 100, which are connected to an RF generator. As with the previously-described jaw members, this electrode/clamp configuration provides a clamped zone of tissue that is significantly wider than the zone of ablated tissue created by the opposed electrodes. This causes for any blood in the clamp zone to be squeezed or expressed out of the ablation zone, thus reducing the likelihood of thrombus formation, as well as minimizing the distance between the electrodes, so that the ablation zone remains narrow. The clamping also eliminates the cooling effect of circulating blood.

With reference to FIG. 32, the electrodes 94, 96 have a T-shaped cross section, with the cross portion of the T resting on the insulating member 88 and the upright portion of the T protruding through a narrow opening in the insulating member 84, thus creating an exposed electrode surface that contacts the tissue grasped between the jaws. In practice, the electrodes are preferably made of gold-plated copper and extend along substantially the entire working surface of the jaw members. The exposed portions of the electrode are generally less than 1.25 mm in width, and preferably between approximately 0.12–0.6 mm in width. This insures that most of the jaw surface is insulator, and that the electrode comprises generally less than one-third of the width of the jaw.

In keeping with a further aspect of the invention, the graspers may provide feedback that permits the user to gauge the completeness (i.e., degree of transmurality) of the ablation. Specifically, a transmural lesion blocks electrical signals because it is non-conductive scar tissue. Because impedance is simply the inverse of conductivity, the ability of the lesion to block electrical signals is accurately indicated by its impedance, which can be measured simultaneously with the creation of the lesion. During RF energy application to the tissue to be ablated, the current and voltage applied to the tissue are measured, and the impedance calculated and stored. Based upon a function of the impedance (e.g., its value, the change in value, or the rate of change in value) it is determined whether ablation is complete and transmural. See e.g., U.S. Pat. No. 5,403,312, which is incorporated by reference herein. Indicator lights or other types of signals (e.g., audible) may be associated with the grasper to correspond to the degree of ablation determined by the impedance feedback system. For example, once the impedance reaches a certain level for a certain period of time, a red light may be activated to signal that ablation is complete.

In keeping with another aspect of the invention, a feedback system for determining the temperature of the ablated tissue is also provided. To this end, the jaws include a series of thermocouples 102 that are supported in the insulating member 84 remote from the associated electrode 94 near the edge of the jaw 78. The thermocouples 102 protrude slightly through the surface of the insulating member 84 so as to engage any tissue clamped between the jaws 72, 74. Wires 104 are attached to the thermocouples 102 to transmit the information received to a remote location. Again, a visual or other indicator may be provided to alert the user that a certain pre-determined critical temperature (e.g., 40° C.) has been reached, thus permitting the user to avoid undesired thermal spread.

Figure 33:
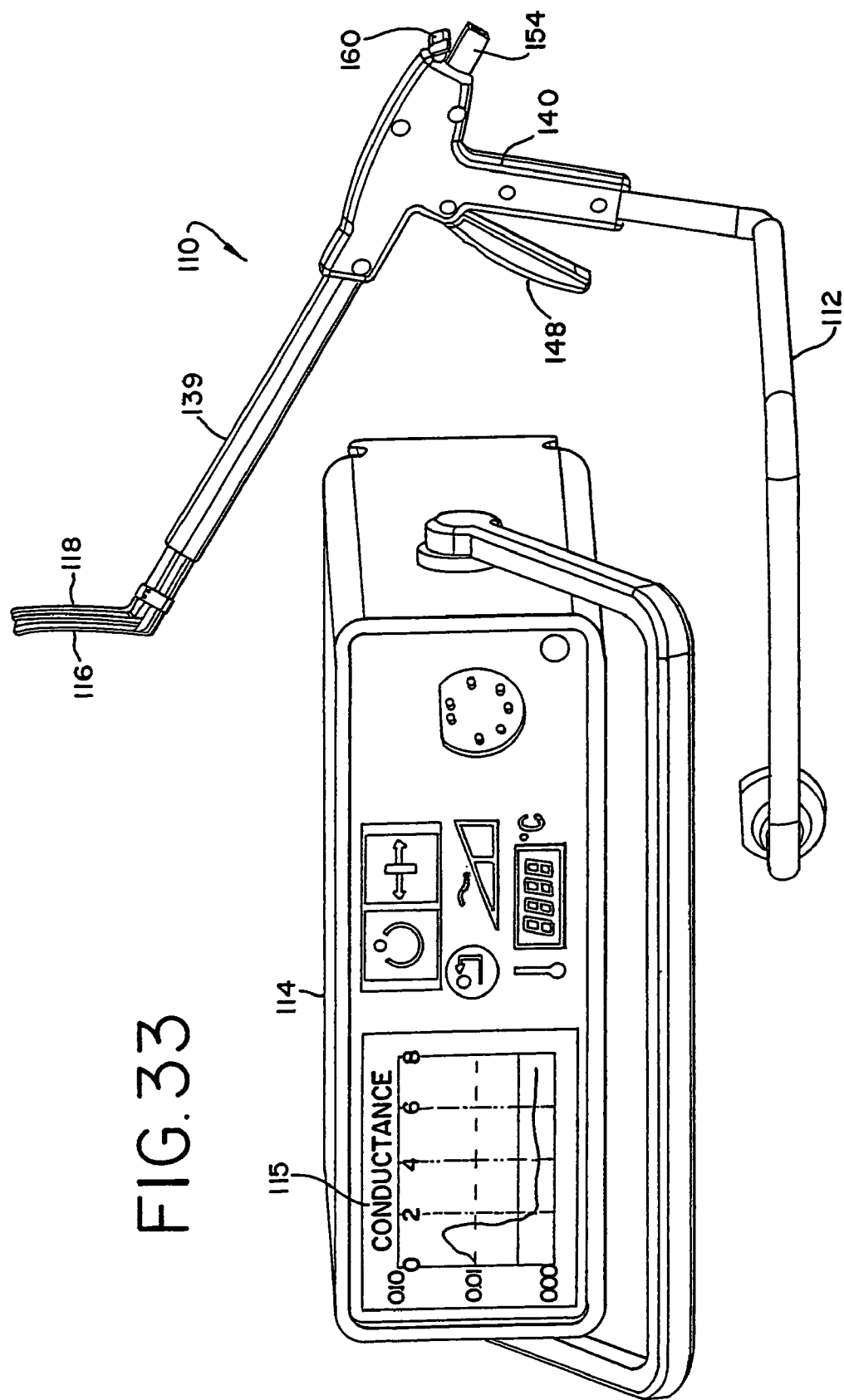
FIG. 33 is a perspective view of a further embodiment of a grasper, which may be used in either an open or a minimally invasive procedure, along with its associated electrosurgical generator.
Figure 34:
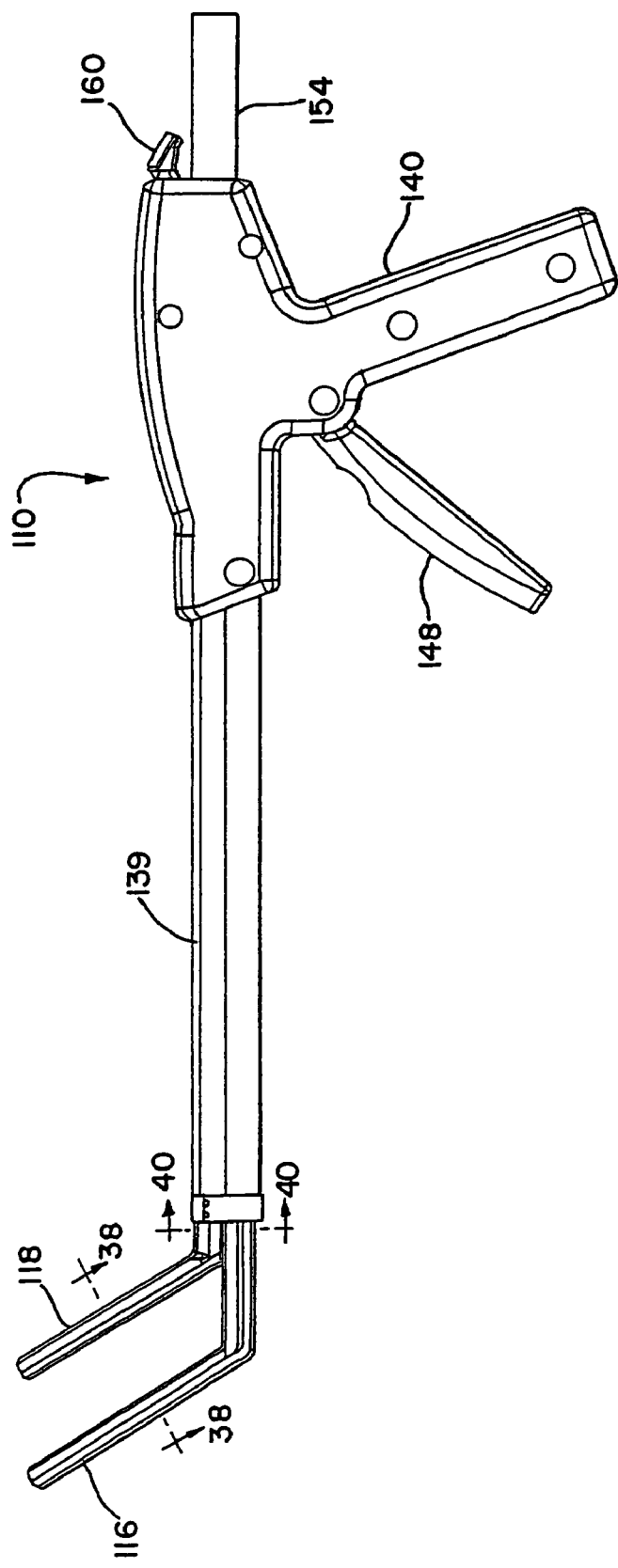
FIG. 34 is a side view of the grasper of FIG. 33 showing the grasper in its "open" position.
Figure 38:
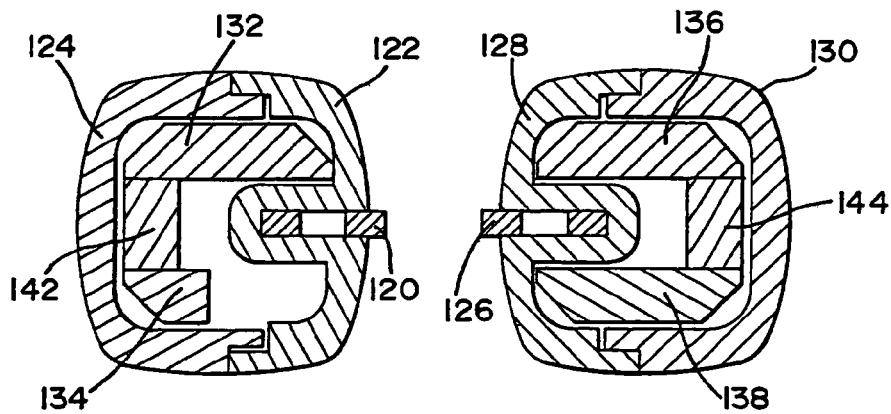
FIG. 38 is a cross-sectional view taken along line 38—38 of FIG. 34 showing the grasper jaws in the "open" position.

Turning to FIGS. 33–37, there is a further version of a cardiac grasper 110 suitable for both open and minimally-invasive procedures in accordance with the present invention. As seen in FIG. 33, the grasper 110 includes a cord 112 for housing the conductors (not shown) and for plugging into an electrosurgical generator 114 to provide current to the grasper 110. As discussed above, the generator 114 includes a display 115 to provide a simultaneous visual indication of the degree of conductance of the tissue being ablated. The instrument 110 includes opposed parallel, curved jaw assemblies 116, 118 with jaw assembly 116 being fixed and jaw assembly 118 being movable between an open position (as seen in FIGS. 34 and 36) to a closed position (shown in FIG. 37), the spacing between the jaws being substantially uniform or constant. The fixed jaw assembly 116 comprises a fixed electrode 120, a fixed insulator 122 and a fixed jaw cap 124. The fixed electrode 120 provides an electrical pathway adjacent to the tissue to be ablated and is located on the inside of the fixed jaw assembly 116 (the "inside" being defined as the side that contacts the tissue to be ablated). The fixed insulator 122 surrounds the fixed electrode 120 and forms the inside of the fixed jaw assembly 116. The fixed jaw cap 124 forms the backside of the fixed jaw assembly 116 (the "backside" being defined as the surface opposite the fixed electrode 120).

The drive jaw assembly 118 comprises a drive electrode 126, a drive insulator 128, and a drive jaw cap 130. The drive electrode 126 provides a second electrical pathway adjacent the tissue to be ablated and is located on the inside of the drive jaw assembly 118 ("inside" being defined as the side contacting the tissue to be ablated). The drive insulator 128 surrounds the drive electrode 126 and forms the inside of the drive jaw assembly 118. The drive jaw cap 130 forms the backside of the drive jaw assembly 118 ("backside" being defined as the surface opposite the drive electrode 126).

Each of the electrodes 120, 126 is attached to an electrically conductive means, such as a wire, that runs the length of the extension shaft and through the conductor cord 112 for coupling to the RF generator 114.

Each jaw assembly 116, 118 is supported by a two piece extension shaft comprising a right fixed member 132 and left fixed member 134 (for the fixed jaw) and a right drive member 136 and left drive member 138 (for the drive jaw 118). A shaft cap 139 covers the coextensive portions of the fixed members 132, 134 and the drive members 136, 138 (when the jaws are in the open position as seen in FIG. 34). The right fixed member 132 and left fixed member 134 combine to form a structure that extends from a handle 140, through the shaft cap 139, and then terminating at the distal end of the instrument 110 in the fixed jaw assembly 116 on the right and left sides, respectively, of the instrument. Similarly, the right drive member 136 and left drive member 138 extend from the handle 140, through the shaft cap 139, and then terminate in the drive jaw assembly 118 on the right and left sides, respectively, of the instrument. The portions of the fixed members 132, 134 co-extensive with the fixed jaw assembly 116 are joined by a fixed bridge 142 along the length of the jaw. Similarly, the portions of the drive members 136, 138 co-extensive with the drive jaw assembly 118 are joined together by a drive bridge 144 along the length the drive jaw 118.

The handle 140 comprises two mating halves 140a, 140b for encapsulating the actuation and force control mechanisms for the grasper, as well as providing for grounding of the shaft components by means of a conductive shaft pin 141. In order to move the drive jaw assembly 118 between its open and closed positions, the handle 140 includes a lever comprising a pair of lever plates 146 and a lever shroud 148. The lever is pivotally mounted on a support member 150 extending between the two halves 140a, 140b of the handle 140, with a lever spring 151 biasing the lever to its open position (FIG. 34). The lever plates 146 are coupled by a lever pin 152 to a carriage 154 that captures the proximal ends of the drive members 136, 138, so as to provide translational motion to these members.

The carriage 154 includes a lost motion assembly comprising a carriage spring 156 for controlling the minimum and maximum loads that can be applied to tissues that are to be captured between the jaw assemblies 116, 118. As can be readily appreciated, the thicker the tissue that is grasped between the jaws, the greater the compression of the spring 156, and the greater the compression force exerted by the jaws on the tissue. (The range of tissue thickness is expected to be between about 1–15 mm.) In other words, the force exerted by the jaws on the tissue held therebetween increases as the distance between the jaws increases. Adjustment of the compression force is accomplished by preloading the carriage spring 156 with a load adjustment screw 158. The lost motion assembly also includes a thumb latch 160 for releasing the clamping pressure and for providing a mechanical stop for the spring-loaded carriage 154. The thumb latch 160 is pivotally mounted on a latch pin 162 to secure the thumb latch to the handle 140. Additionally, a latch spring 164 is provided for biasing the thumb latch 160 to its locked position. A latching step on the carriage 154 interfaces with the tip of the thumb latch 160 to provide for the mechanical stop.

When the lever is pivoted with respect to the handle 140, the drive jaw assembly 118 and its drive members 136, 138 slide along the longitudinal direction of the shaft to bring the two jaw assemblies 116, 118 into contact with the tissue intended to be grasped.

In order to ablate a narrow, long region of biological tissue with the instrument 110, the tissue is first placed between the open instrument jaws 116, 118. The user then grasps the actuation lever comprising the lever plates 146 and lever shroud 148 to apply the force required to drive the drive members 136, 138 and drive jaw assembly 118 distally, thus compressing the tissue and automatically engaging the thumb latch 160. The thumb latch 160 locks the position of the drive members 136, 138 and the drive jaw assembly 118 with respect to the handle 140 and the fixed jaw assembly 116. The amount of jaw force on the tissue is controlled by the lost motion assembly between the lever and the drive members 136, 138.

With the jaws closed on the tissue, the operator activates the RF generator 114. RF energy passes through the tissue between the electrodes 120, 126, thus ablating the tissue between these electrodes. After completion of the ablation cycle, the operator releases the clamping of the tissue by depressing the thumb latch 160, thus releasing the carriage 154. With the carriage 154 released, the lever spring 151 drives the drive members 136, 138 and the drive jaw assembly 118 proximally to their open positions. The actuation lever, since it is directly coupled to the carriage 154, also returns to the open position.

Turning to FIGS. 41–51 there is seen in schematic form various configurations for the electrodes 120, 126 for use in conjunction with the grasper 110. Each of FIGS. 41 and 43–51 show a cross-section through the instrument jaws as clamped on the tissue to be ablated. Each electrode is formed of a piece of electrically conductive metal that may be plated with a biocompatible material.

Figure 41:
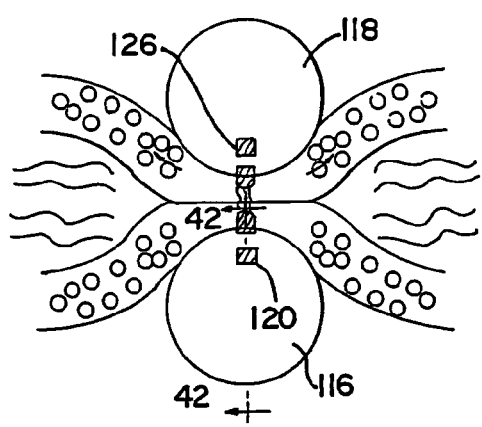
FIGS. 41–51 show alternate constructions for the electrodes suitable for use in the present invention, with FIGS. 41 and 43–51 being cross-sectional views similar to FIGS. 38 and 39, and FIG. 42 being a cross-sectional view taken along line 42—42 of FIG. 41.
Figure 42:
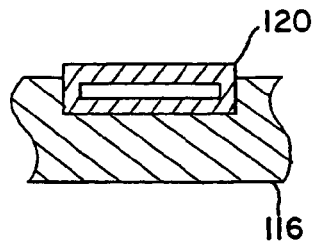

With reference to FIGS. 41 and 42, the electrode geometry consists of a largely rectangular electrode with a window of material removed from the central region. The window area is filled with the insulator material 122, 128. At the clamping surface the electrode insulator material leads away from the electrode on a radius. The electrode material protrudes outside the clamping surface of the insulating material. However, the electrode may also be flush with the clamping surface.

Figure 43:
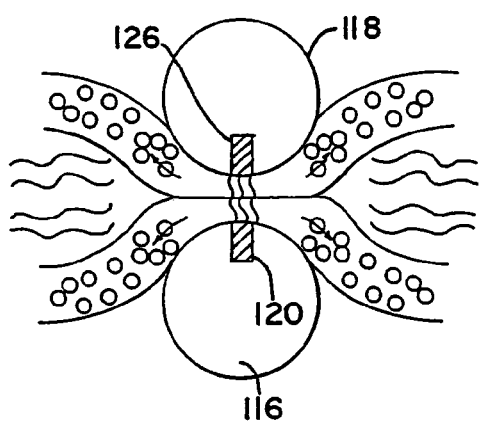

With reference to FIG. 43, the electrode geometry is largely rectangular and the electrode insulator material leads away from the electrode on a radius. The electrode is flush with the clamping surface of the insulator material.

Figure 44:
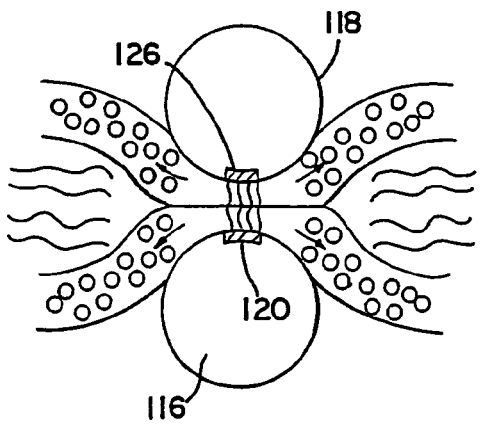

With reference to FIG. 44, the electrode is applied to fill a groove in the insulator material by way of a plating process. The electrode geometry is largely rectangular and the electrode insulator material leads away from the electrode on a radius. The electrode plating is largely flush with the clamping surface of the insulator material.

Figure 45:
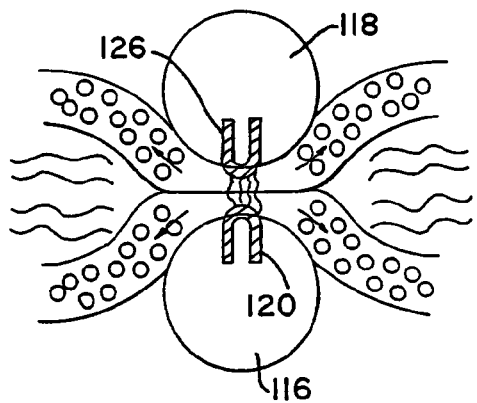

With reference to FIG. 45, the electrode is formed into a U-shaped element. The electrode insulator material leads away from the electrode on a radius. As shown, the electrode material extends outside the clamping surface of the insulator material. However, the electrode material may also be flush with the insulator clamping surface.

Figure 46:
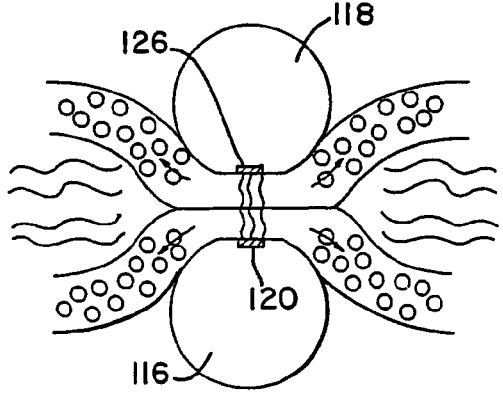

With reference to FIG. 46, the electrode is applied to fill a groove in the insulator material by way of a plating process, with the electrode geometry being largely rectangular. The electrode insulator material creates a small flat surface perpendicular to the closure plane that is largely flush with the surface of the plate or electrode. As shown, the electrode material is flush with the clamping surface of the insulator material. However, the electrode material may also be applied so that it extends outside the insulator clamping surface.

Figure 47:
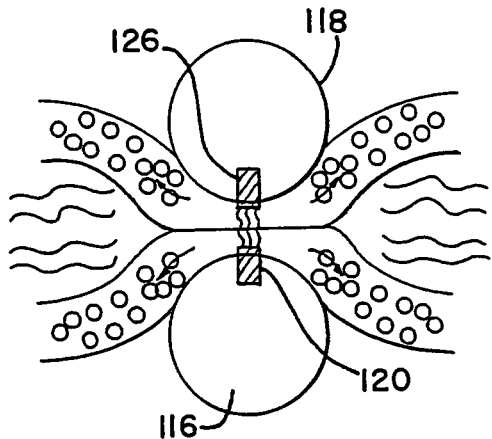

With reference to FIG. 47, the electrode geometry is largely rectangular and the electrode insulator material leads away from the electrode on a radius. The electrode material extends outside the clamping surface of the insulator material.

Figure 39:
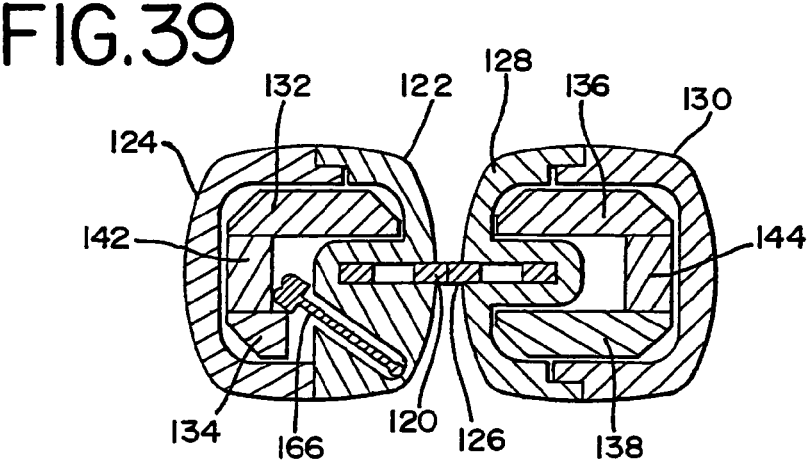
FIG. 39 is a cross-sectional view of the grasper jaws taken along the line 39—39 of FIG. 37 showing the grasper jaws in the "closed" position.
Figure 40:
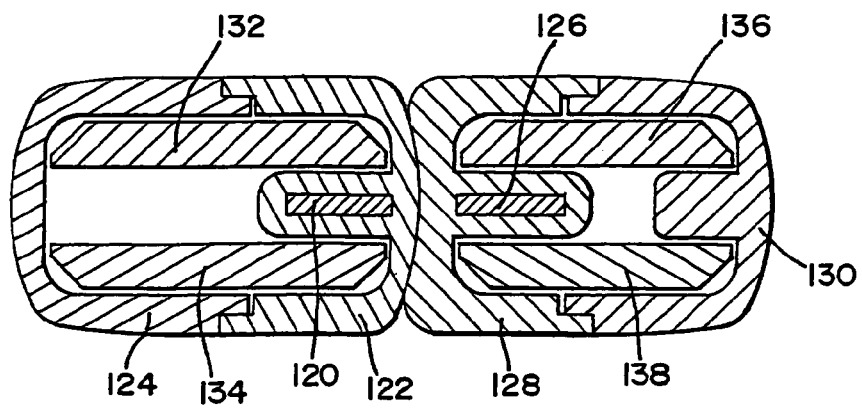
FIG. 40 is a cross-sectional view of the graspers taken along line 40—40 of FIG. 34.
Figure 48:
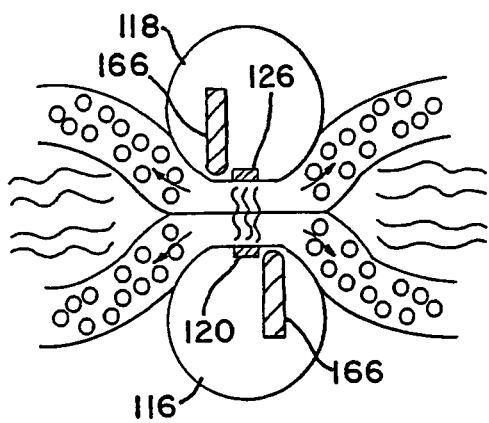

With reference to FIG. 48, the electrode configuration is again largely rectangular, with the electrode insulator material creating a small flat surface perpendicular to the closure plane that is largely flush with the surface of the plate or electrode. The electrode is flush with the clamping surface of the insulator material and a temperature sensing means, such as a thermocouple 166 (see also FIGS. 35 and 39), is positioned in close proximity to the electrode, but electrically isolated from the RF energy.

Figure 49:
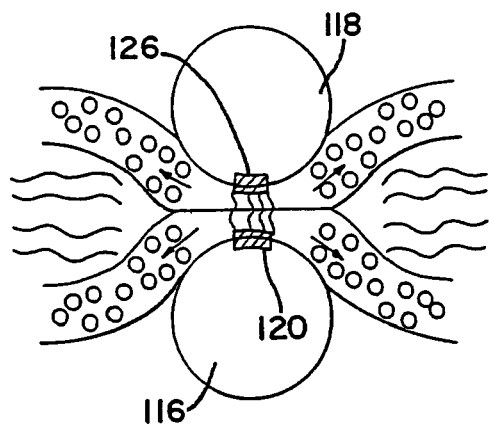

With reference to FIG. 49, the electrode is applied to fill a groove in the insulator material by way of a plating process. The electrode geometry is largely rectangular and the electrode insulator material leads away from the electrode on a radius.

Figure 50:
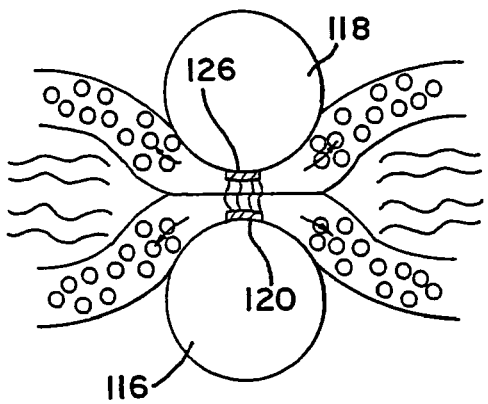
Figure 51:
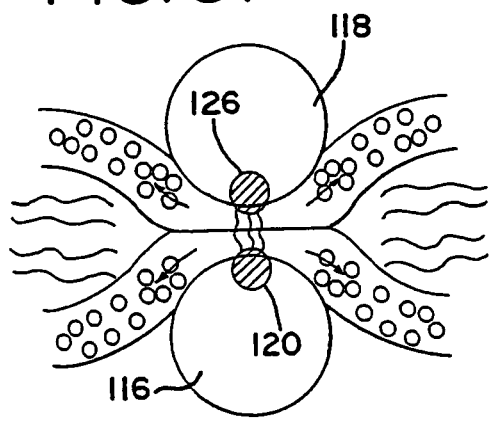

With reference to FIG. 50, the electrode is applied to the surface of the electrode insulator material by way of a plating process. The electrode geometry is largely rectangular with the electrode insulator material leading away from the electrode on a radius. The electrode plating is largely flush with the clamping surface of the insulator material. With reference to FIG. 51, the electrode is round wire made from an electrically conductive metal that may be plated with a biocompatible material. The electrode insulator material leads away from the electrode on a radius. As shown, the electrode material extends outside the clamping surface of the insulator material. However, the electrode material may also be flush with the insulator clamping surface.

Figure 63:
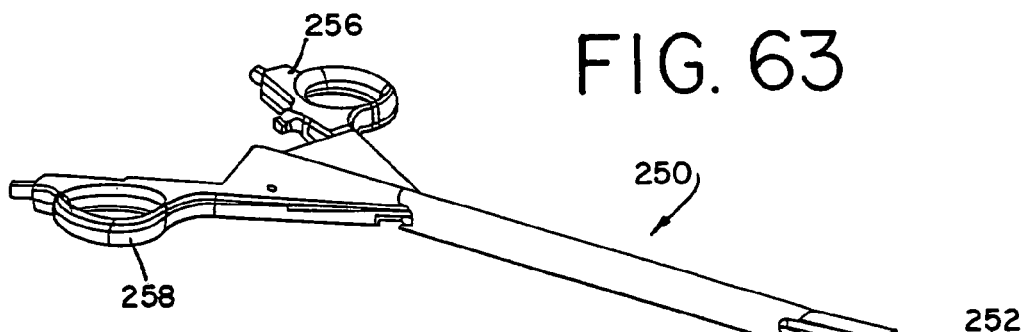
FIG. 63 is a perspective view of a further embodiment of a grasper adapted for use in minimally invasive procedures.
Figure 64:
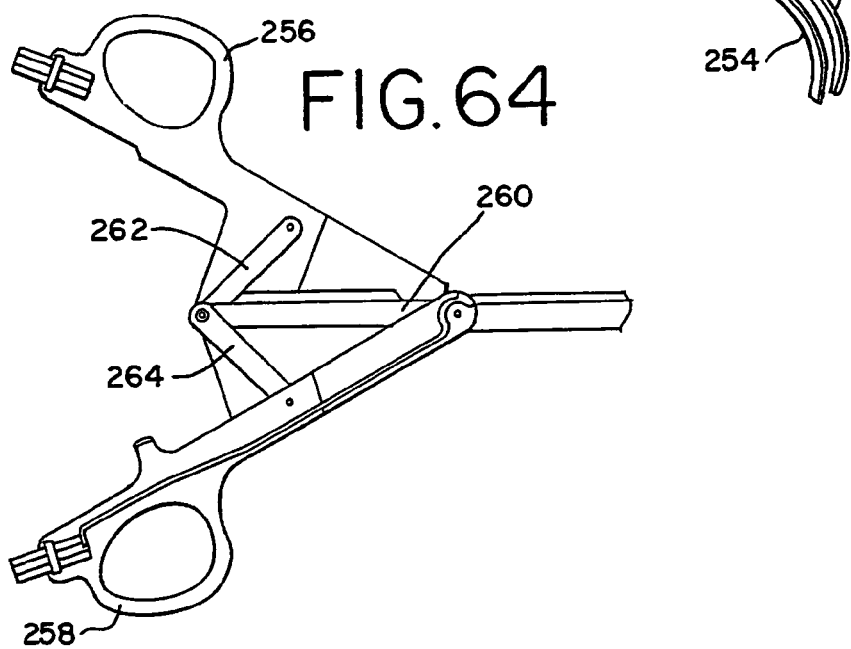
FIG. 64 is an enlarged plan view of the handle position of the grasper of FIG. 63, with portions removed to show detail.
Figure 65A:
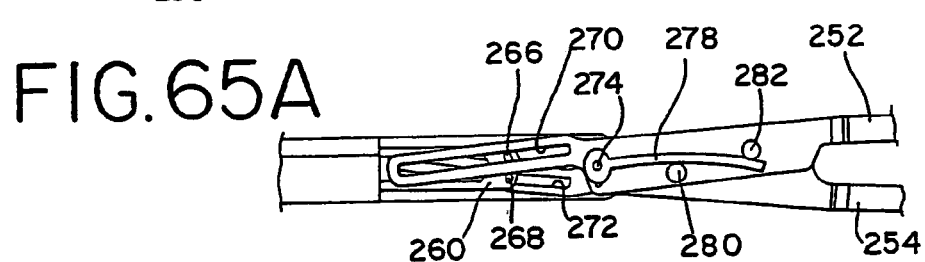
FIGS. 65A and 65B are enlarged plan views of the jaw actuation mechanism for the grasper of FIG. 63.
Figure 65B:
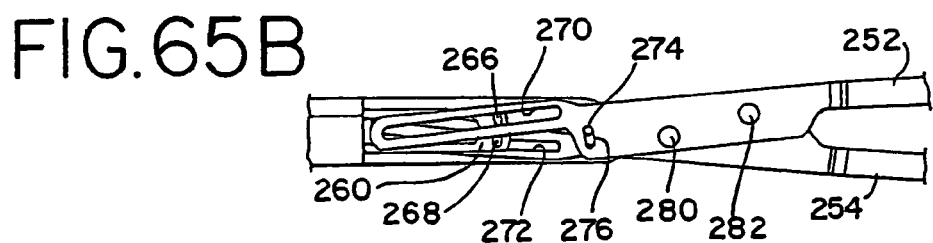

A further embodiment of a grasper according to the present invention is shown in FIGS. 63–65 and is designated generally 250. The grasper 250 has jaws 252, 254 similar in structure to those described above in connection with the embodiments of FIGS. 28–32 and 33–40, but includes a different actuation mechanism. Specifically, the jaws 252, 254 of the grasper 250 are biased so that they are normally in the closed position, the jaws being moved to the open position by moving the two handle members 256, 258 towards each other. This action serves to withdraw a push-rod 260 (FIG. 64), which is pivotally connected to the handle members 256, 258 by links 262, 264. With reference to FIG. 65A and FIG. 65B. The distal end of the push rod 260 includes two pins 266, 268 which are captured in slots 270, 272 in their respective jaw members 252, 254. When the pins 266, 268 are located in the distal ends of the slots 270, 272, the jaws are in the closed position. The jaws 252, 254 open as the pins 266, 268 move proximally in the slots 270, 272 through the withdrawal of the push rod 260 by the closing of the handle members 256, 258.

The jaws 252, 254 also include a lost motion connection including a spring to bias the jaws toward the closed position. With reference again to FIG. 65A and FIG. 65B, the jaws 252 and 254 are pivotally connected to each other by means of a pin 274. The pin 274 is secured to the jaw member 254, but is received in an elongated slot 276 in jaw member 252. The pin 274 is biased to the top of the slot 276, thus biasing the jaws 252, 254 to the closed position, by means of a leaf spring 278 having one end secured to the pin 274 and the other end captured between two studs 280, 282 carried on the jaw member 252.

Figure 52A:
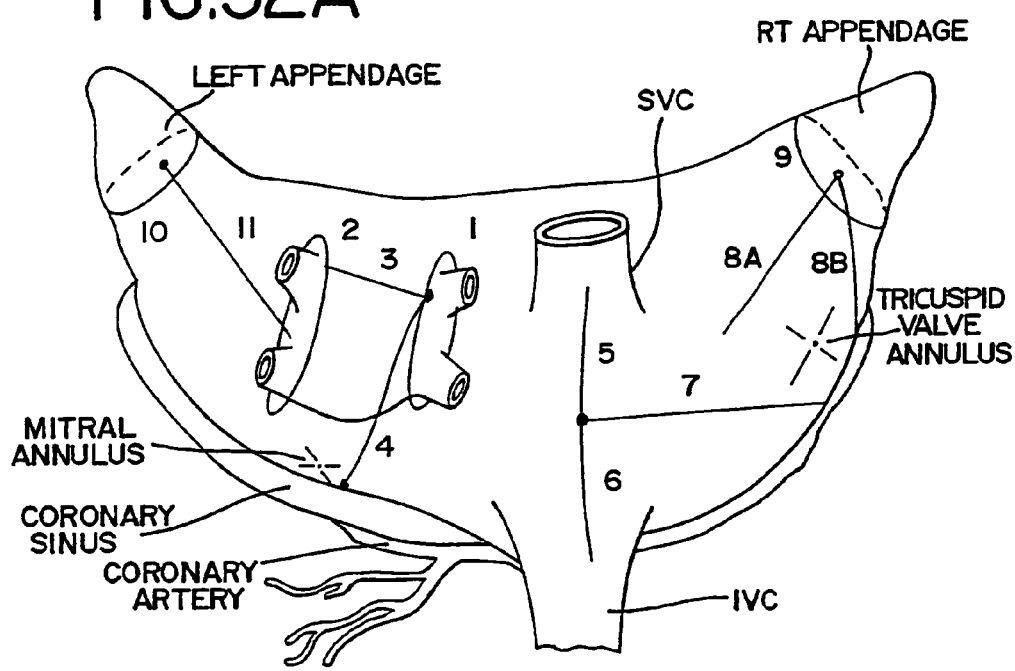
FIGS. 52A–K illustrate eleven different ablations to the left and right atrium (as seen from behind in FIG. 52A) and the methods for making the lesions (FIGS. 52B–K).

FIGS. 52A–K illustrate a series of 11 different lesions or ablations that may be made using either an open or a minimally invasive technique with the graspers described above. Turning first to FIG. 52A, there is seen a view of the heart showing the right and left atriums (as viewed from behind). The heart includes the left atrial appendage (LAA) and the right atrial appendage (RAA). The right pulmonary veins (RPVs) and left pulmonary veins (LPVs) enter into the top of the left atrium. The superior vena cava (SVC) and inferior vena cava (IVC) are also shown. The mitral valve annulus is designated as MVA, while the tricuspid valve annulus designated TVA. In FIG. 52A, 11 different lesions are indicated by the reference numerals 1–11. A method for making each of these lesions is illustrated in the following FIGS. 52B–K. It should be appreciated that, depending upon a particular patient's indications, the lesions 1–11 may be created in a variety of combinations.

Figure 52B:
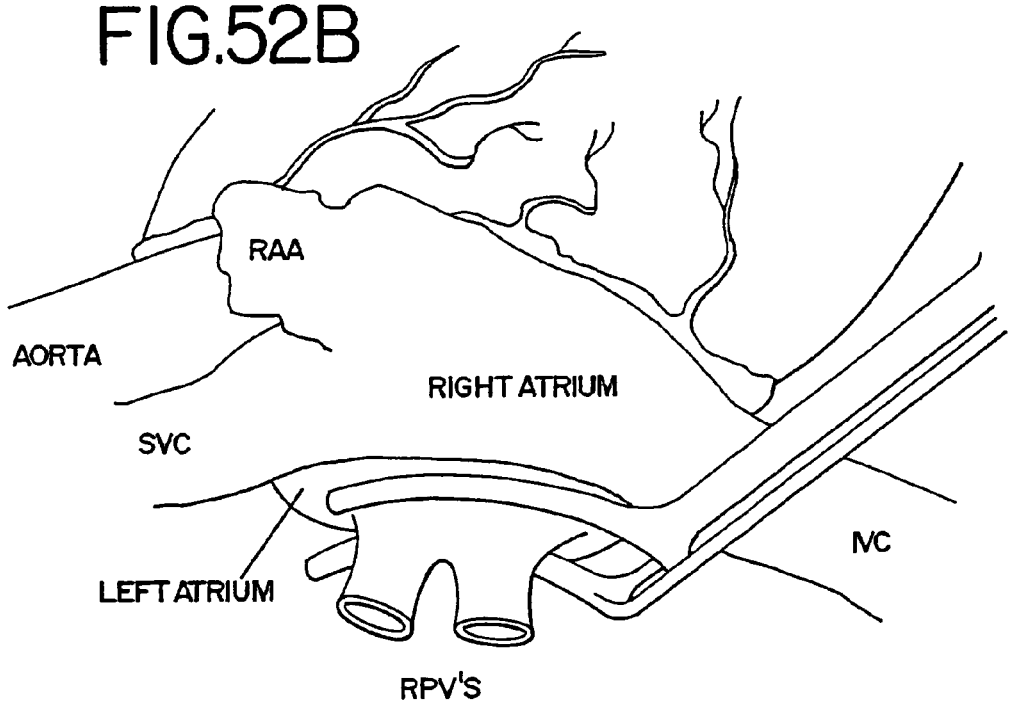
Figure 52C:
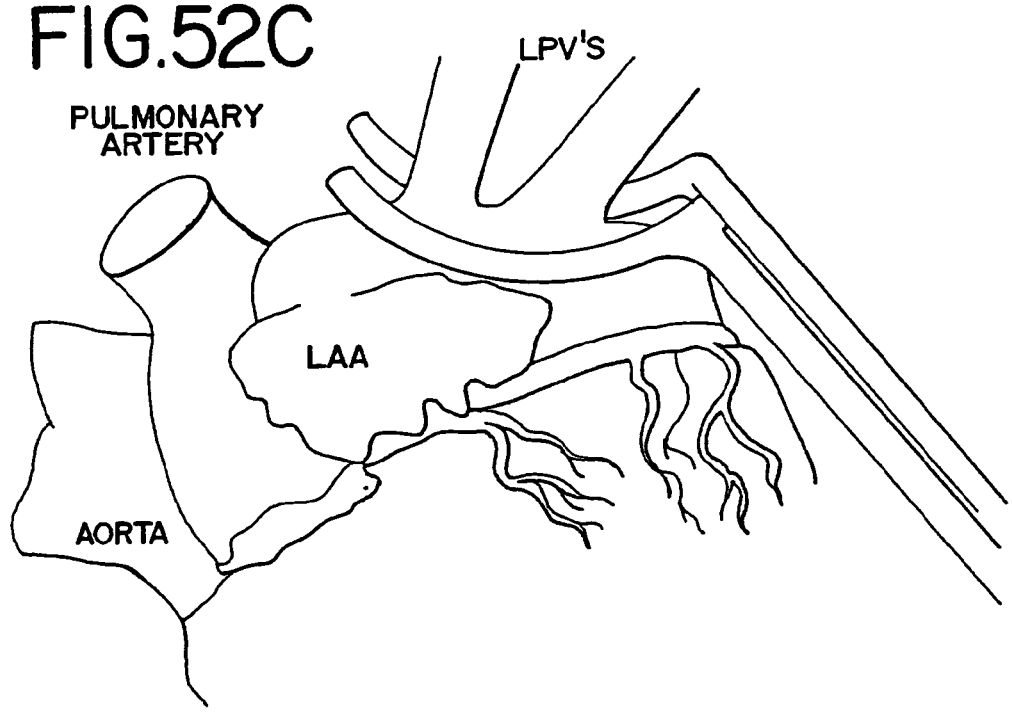

With reference to FIG. 52B, a method for making lesion 1 to circumscribe the right pulmonary veins (RPVs) is shown. This lesion is made completely epicardially in a manner similar to that illustrated in FIGS. 23–27. FIG. 52C illustrates lesion 2, an epicardial ablation that fully circumscribes the left pulmonary veins (LPVs). Again, this lesion may be made in a manner similar to that illustrated in FIGS. 23–27.

Figure 52D:
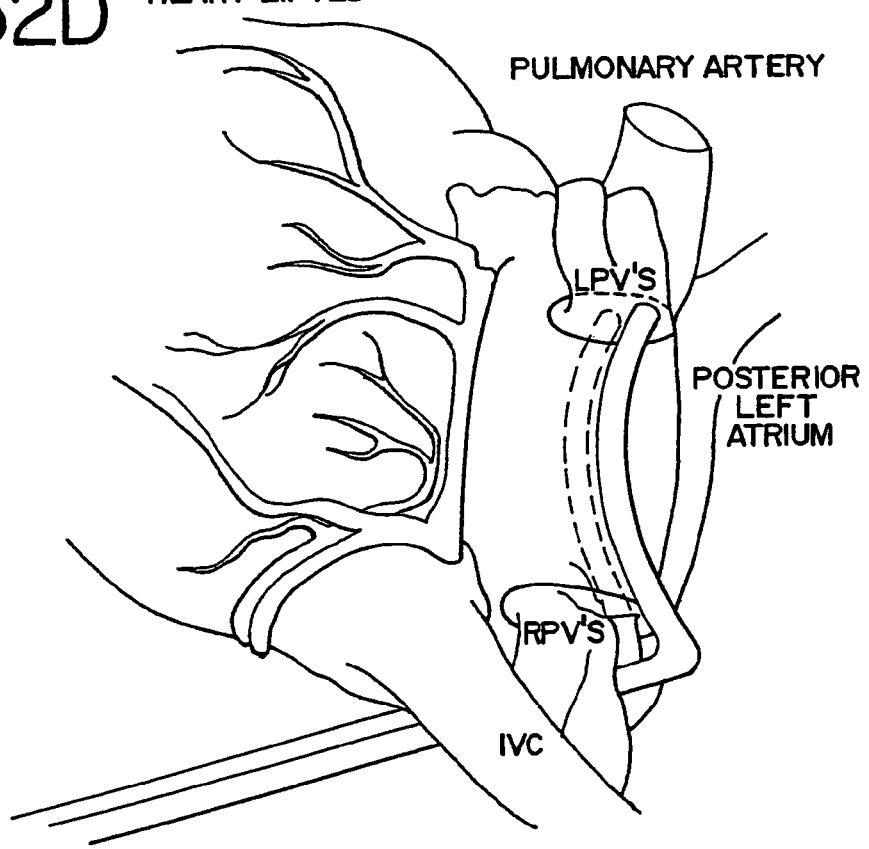

FIG. 52D illustrates a method for making lesion 3, which connects lesions 1 and 2. Lesion 3 is made with only one of the jaws of the graspers being located epicardially. The mating jaw is inserted into the interior of the heart through a small incision which is sealed using a purse-string suture. The incision as illustrated is made interior the lesion 1 encircling the right pulmonary veins (RPVs).

In order to be sure that lesions 1 and 2 are fully transmural and completely encircle the RPV's and LPV's so as to effectively electrically isolate the RPVs and LPVs from the atrium, one of the jaw members of the grasper may be provided with an EKG sensor intermediate the ends of the jaw. The EKG sensor is located on the jaw so that, when the grasper jaws are closed on the tissue intended to be ablated, the EKG sensor contacts the tissue outside of the ablation line on the pulmonary vein side of the line of ablation. Thus, by monitoring the EKG of the atrial tissue adjacent the pulmonary vein, the surgeon can determine simultaneously with the creation of the ablation line whether the pulmonary veins have been electrically isolated from the atrium.

In addition, the grasper jaw may include pacing electrodes intermediate its ends. The pacing electrodes are located on the opposite side of the ablation electrode from the EKG sensor, again outside the line of ablation. Thus, a pacing pulse can be transmitted by the pacing electrodes which will be sensed by the EKG sensors when the jaws of the grasper are closed on the tissue. The pacing and sensing continues as the ablation electrodes are activated to create the lesion. When the lesion is complete, the EKG sensors will no longer be able to detect the pacing signal.

Figure 66:
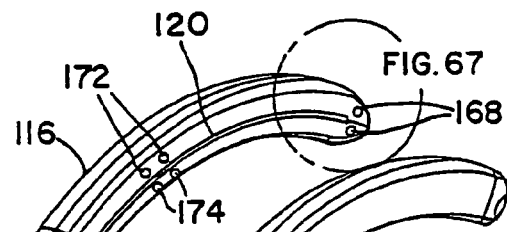
FIGS. 66 is an enlarged fragmentary perspective view of the jaws of grasper of FIGS. 33–40.

When a pacing electrode is paired with the EKG sensor, the EKG sensors may be on either side of the jaw, i.e., on either the pulmonary vein side or the atrial side of the ablation line created by the ablation electrodes. The EKG electrodes and pacing electrodes are best seen in FIG. 66, where there is seen a pair of bipolar pacing electrodes 172 and a pair of bipolar EKG electrodes or sensors 174. The pacing electrodes 172 and the EKG electrodes 174 are connected to a pulse generator and monitor, respectively, in the well-known manner.

Lesion 4 connects the lesion 1, which surrounds the right pulmonary veins, to the mitral valve annulus (MVA). It may be made through the same incision and purse-string suture used for making lesion 3. With reference again to FIG. 52D, the jaws of the grasper are merely rotated down so that the distal end of the jaw overlies the mitral valve annulus.

When making lesion 4, care must be exercised in locating the grasper jaws so that the electrodes, when RF energy is applied, do not damage the mitral valve leaflets. It is known that the electrical signals generated by atrial tissue differ from the electrical signals generated by ventricular tissue. Consequently, the distal tip of one of the jaw members of the grasper includes an EKG sensor so that the EKG of the tissue contacted by the tip of the grasper can be monitored.

Figure 67:
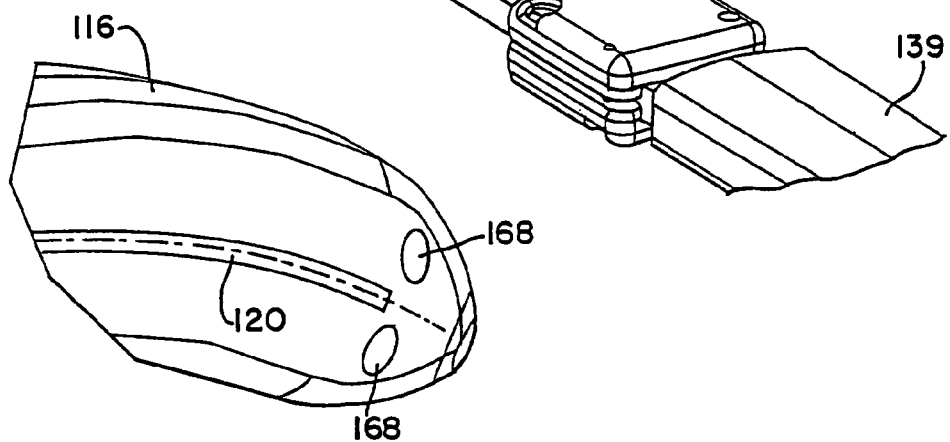
FIGS. 67 is an enlarged perspective view of the tip of the fixed jaw shown in FIG. 66.

As best seen in FIGS. 66 and 67, the distal tip of the fixed jaw 116 includes a pair of laterally-opposed bipolar EKG electrodes or sensors 168 spaced slightly distally from the distal-most end of the electrode 120. The sensors 168 are connected to conductive leads 170 (FIG. 33) that are adapted to be connected to an EKG monitor (not shown) to provide a display of the EKG. Thus, as the jaws of the grasper are rotated downwardly after making lesion 3, the surgeon can constantly monitor the EKG, looking for the change from an atrial EKG to a ventricular EKG, to facilitate accurate placement of the jaw tip on the mitral valve annulus, and away from the mitral valve leaflets.

Figure 52E:
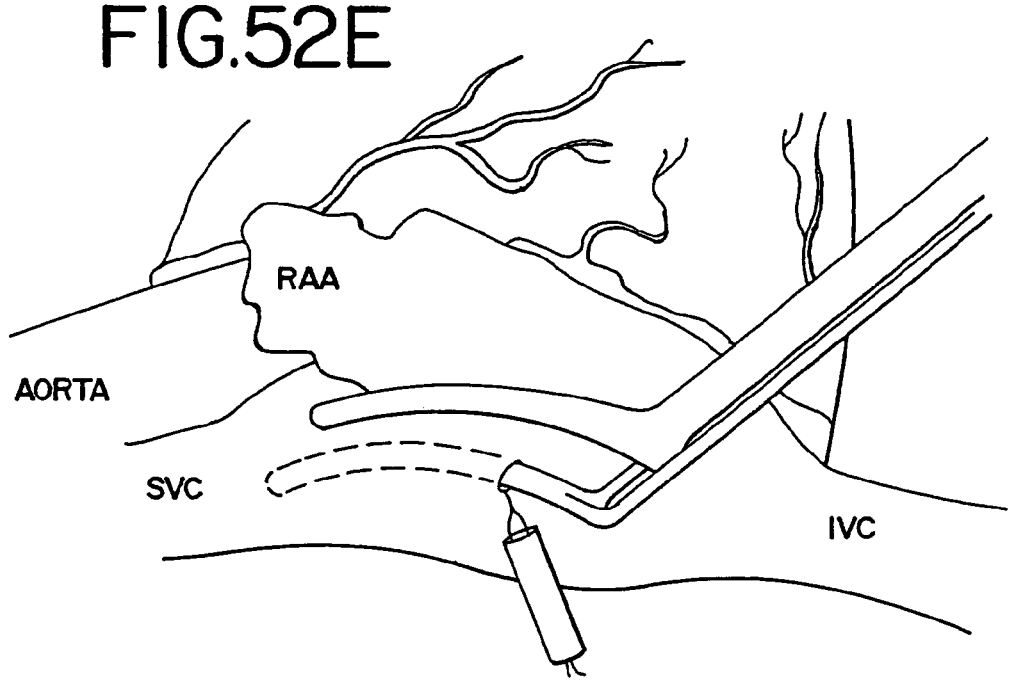
Figure 52F:
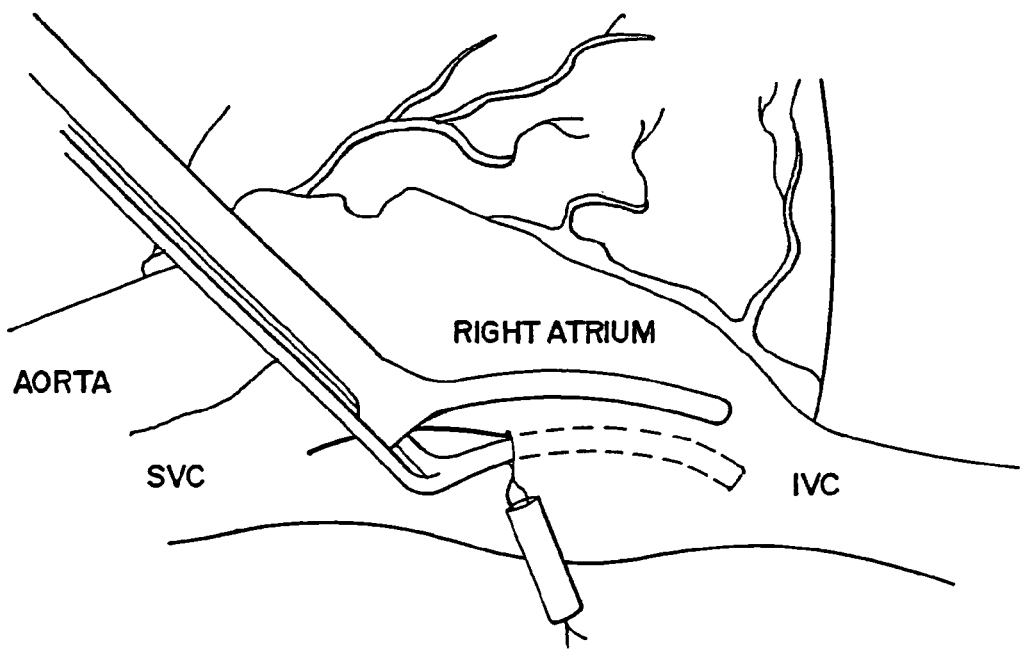
Figure 52G:
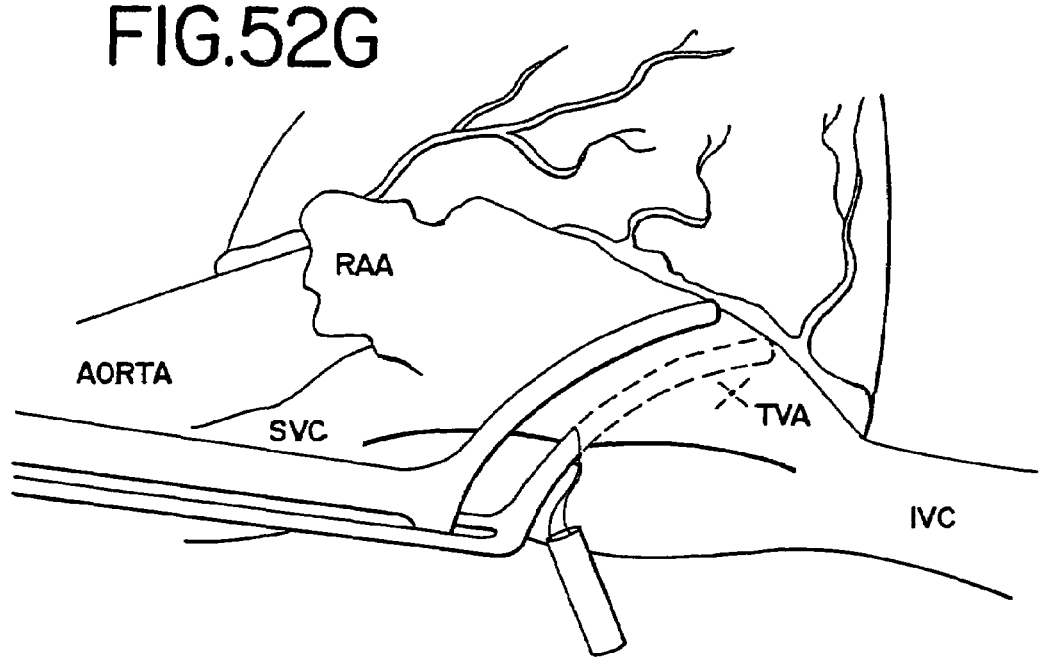

It may also be desirable to make a lesion between the superior vena cava (SVC) and the inferior (IVC). This may be created in two steps, in which lesions 5 and 6 are made. With reference to FIG. 52E, an incision with purse-string suture is made approximately midway between the SVC and IVC, with one of the jaws of the grasper being inserted into the incision so as to have its end adjacent the base of the SVC. The lesion 5 is formed and then the instrument is rotated 180° as shown in FIG. 52F, to make lesion 6. Lesion 7 may conveniently be made through the same incision and purse-string suture as lesions 5 and 6, as shown in FIG. 52G. Lesion 7 extends from between the SVC and IVC out toward the right atrial appendage (RAA).

Figure 52H:
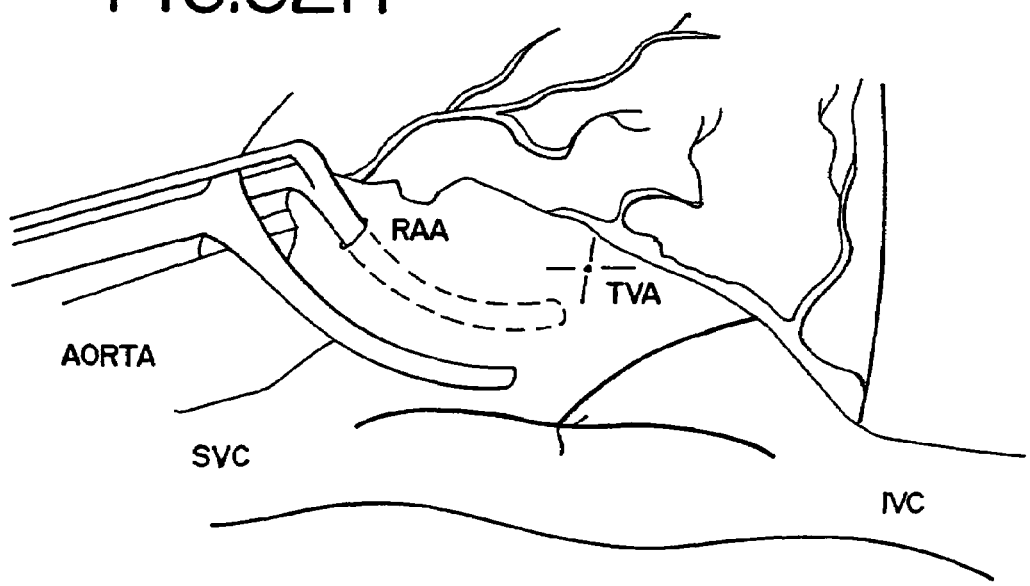
Figure 52I:
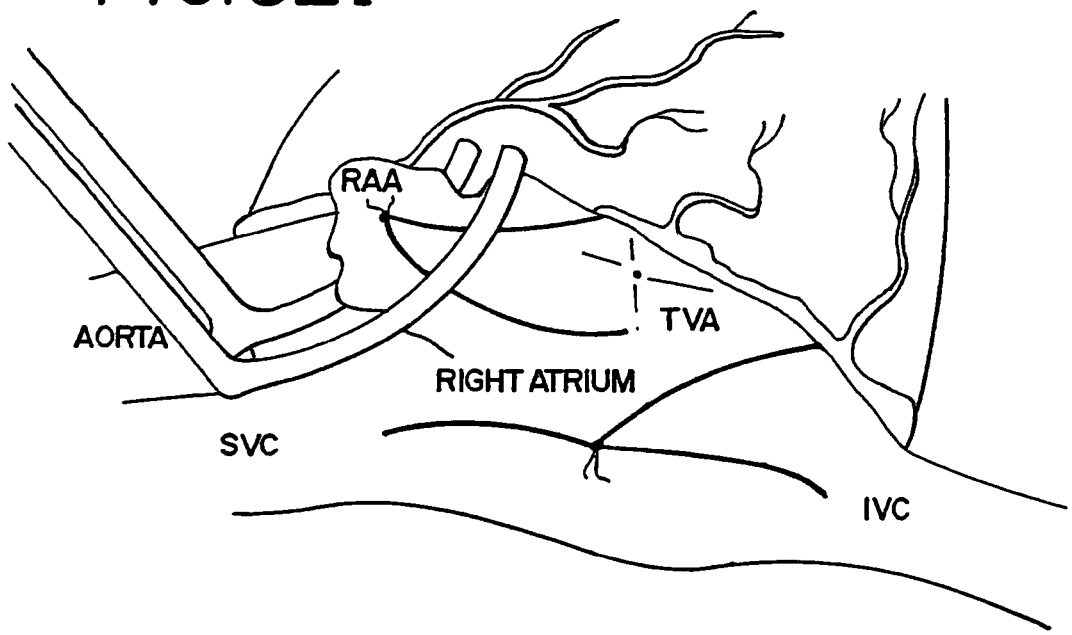
Figure 52J:
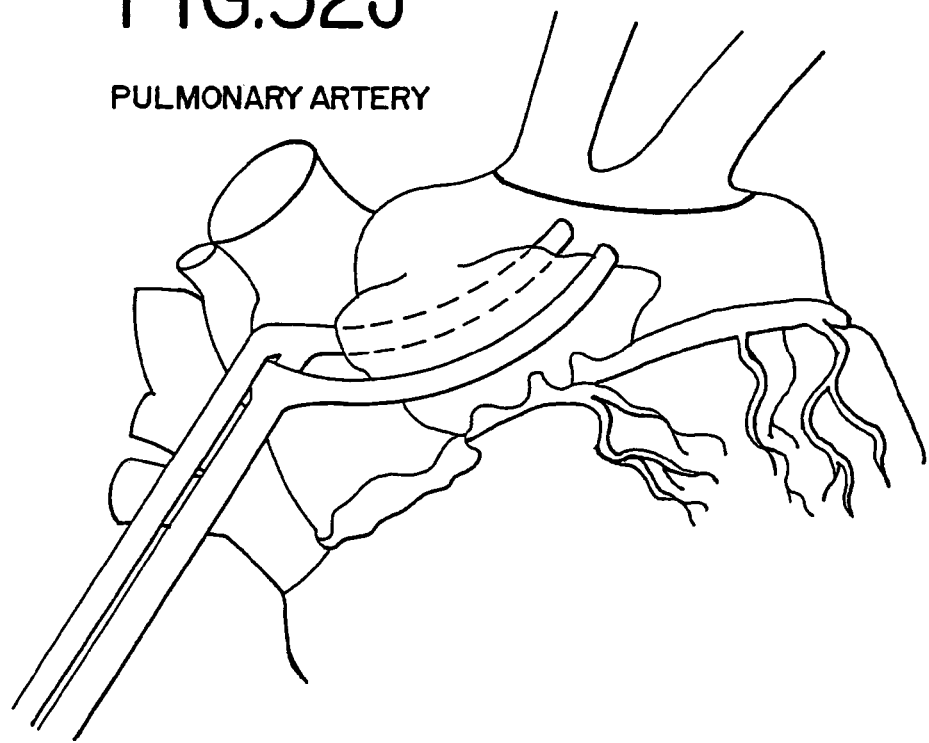
Figure 52K:
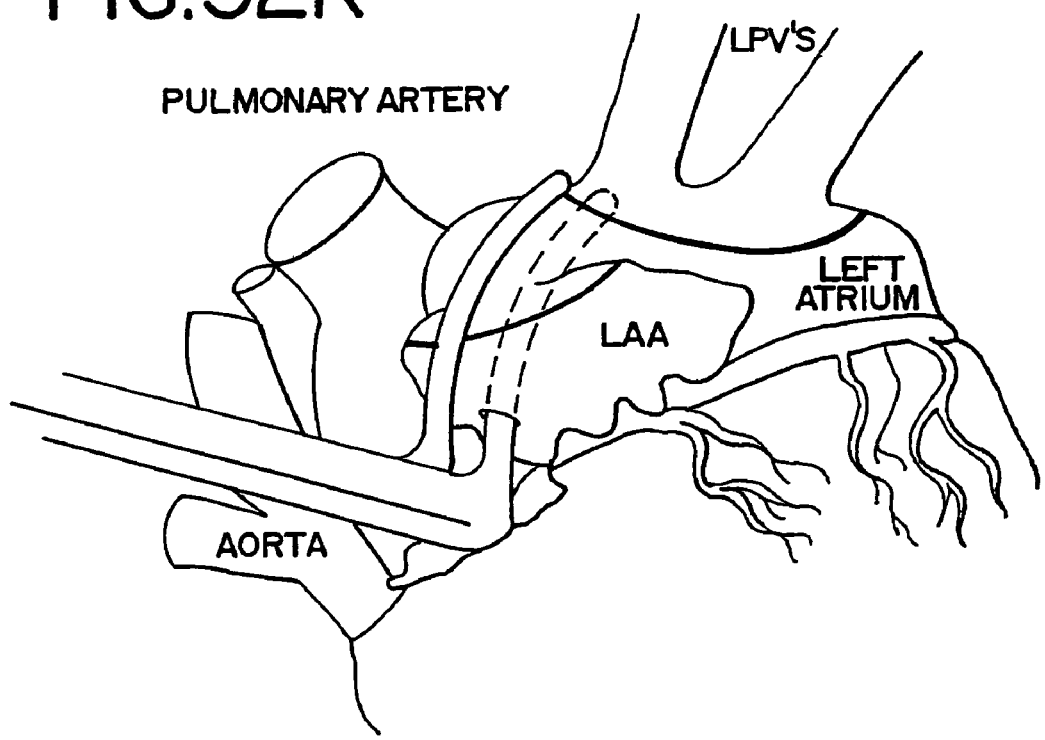

A lesion 8 is made between the right atrial appendage and the tricuspid valve annulus (TVA) utilizing an incision and purse-string suture made in the RAA, as illustrated in FIG. 52H. Lesion 8 is made on the opposite side of the right atrium as lesion 7, and thus is shown in dotted line in FIG. 52A. A lesion 9 may also be made circumscribing the right atrial appendage so as to intersect both lesions 7 and 8. As shown in FIG. 52I, lesion 9 is made epicardially. A similar epicardial ablation circumscribing the left atrial appendage is designated 10 and illustrated in FIG. 52J.

A final lesion 11 is illustrated that connects lesion 10 circumscribing the left atrial appendage with lesion 2 that circumscribes the left pulmonary veins. As illustrated, the lesion 11 is made utilizing an incision and purse string suture through which the grasper jaw is introduced, the incision being located in the left atrial appendage beyond the lesion 10.

In a further embodiment, the present device consists of two long, linear, wire-type electrodes, which are in parallel relationship to each other, each approximately 1 mm in diameter, and 50 mm long. The electrodes are insulated along their entire surface with a thin layer of high dielectric material such as polyamide, except for a thin strip of electrically conductive material that runs along the length of each electrode, in face-to-face relationship with each other. The electrodes are comprised of a high modulus material, such as tungsten or carbon fiber.

One of the electrodes is designed to be introduced into the interior of a hollow organ through a small puncture wound in the wall of the organ. The second electrode is introduced on the opposite side of the hollow organ wall. The device incorporates a mechanism for advancing each electrode individually, or both simultaneously, in parallel relation with each other. The device also includes a clamping mechanism that brings the two electrodes together so that their exposed conductive surfaces are in face-to-face relation and the electrodes exert sufficient pressure to clamp the tissue. Once both electrodes have been advanced to their desired positions, the clamping mechanism is activated which brings the two wires together, and clamps the tissue between the two exposed electrode surfaces. RF energy is then applied between the two electrodes, and the tissue is ablated in a long, continuous, transmural line. A monitoring device measures the voltage, current, impedance, and/or temperature between the two electrodes, and an algorithm determines whether the tissue is fully ablated.

This device provides a way to achieve and verify a fully transmural and continuous line of tissue ablation by locating the atrial tissue between two bipolar wire electrodes, and clamping the tissue. The forceps consist of two electrode pads of opposite polarity designed to grasp and clamp tissue. A well-known method of determining the status of the tissue between the electrode pads is to monitor the current, voltage, and impedance of the tissue, as done using the Richard Wolf generator for bipolar forceps. It is well known in the art that the ablative status of tissue clamped between two bipolar electrodes can easily be determined by monitoring the increase in tissue impedance as the tissue desiccates.

This device is to be used with an RF generator that monitors current, voltage, and impedance to determine the state of tissue ablation of the tissue compressed between the inner and outer electrodes. The RF generator will be equipped with an indicator which informs the user of the status of the clamped tissue, and when ablation is complete (i.e., transmural along the entire length of the electrodes).

This device provides the capability of creating long, transmural lesions through atrial wall tissue of varying thickness because it employs an active bipolar electrode on each side of the atrial wall, and the ablation proceeds from both the inside and outside of the atrial wall. The device is also unique in that the electrodes are used to compress the tissue to be ablated. This compression is critical because the inside and outside surfaces of the atrium can have irregularities, and a high clamping pressure insures that both electrodes are making good contact with tissue along the full length of each electrode. Clamping the tissue also reduces the distance between the electrodes, and makes the ablation more efficient because the electrical energy is more concentrated. Because of this higher concentration of energy, lower powers and temperatures can be used to achieve complete ablation, and the process is considerably faster.

As an example, to fully ablate a 5 mm deep lesion, 30 cm long can take several minutes with an endocardial catheter electrode array, and the temperatures can be as high as 80 to 90 degrees centigrade at the tissue surface with the generator power as high as 40 to 50 watts. In benchtop testing of the present invention in animal hearts, a fully transmural 30 mm line through 5 mm of tissue was achieved in 5 seconds at 20 watts.

With reference to FIGS. 53–54, a further embodiment of the device is shown. The device consists of an inner wire electrode wire electrode 201, an outer wire electrode 202, an inner slider button 203, an outer slider button 204, and a clamping slider tube 205 and button 206. The device body 207 houses the wire electrodes, slider tube and buttons, connector wires 207a and 208, and bipolar connector 209. The device may also include slit needle introducer tip 210.

The operation of the device begins by advancing the inner electrode wire 201 by advancing the slider button 203. Once the inner electrode 201 is advanced to the desired length, the outer electrode 202 is advanced by advancing slider button 204. Note that further advancement of slider button 204 also advances slider button 203, so that both electrodes 201 and 202 advance simultaneously. Because of the bend 202a in the electrode wire 202, and the notch 205a in the slider tube assembly 205, the slider tube advances along with the outer electrode 202. Once both electrodes are advanced to the desired length, the slider tube 205 is advanced so that the end 205b of the slider tube 205 contacts the arcuate wire segment 202b of electrode wire 202. Further advancement of slider tube 205 acts to compress the electrode wires 201 and 202 together along the entire effective length L.

Figure 55:
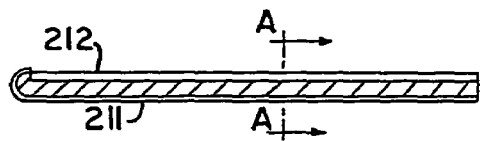
FIG. 55 is a longitudinal cross-sectional view of an obturator tip electrode for use in the device of FIG. 52.
Figure 56:
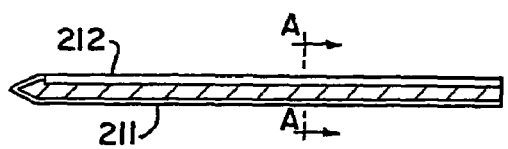
FIG. 56 is a piercing tip electrode for use in the device of FIG. 52.
Figure 57:
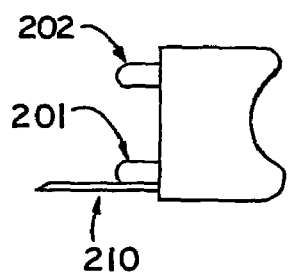
FIG. 57 is an enlarged side view of the tip of the instrument shown in FIG. 52.

FIGS. 55 and 56 show two types of electrode wires, a piercing tip (FIG. 56), and an obturator, or blunt tip (FIG. 55). The electrodes may be similar in construction to those shown in FIGS. 2–6, which are described above. FIG. 57 shows a side view of the instrument tip.

Figure 58A:
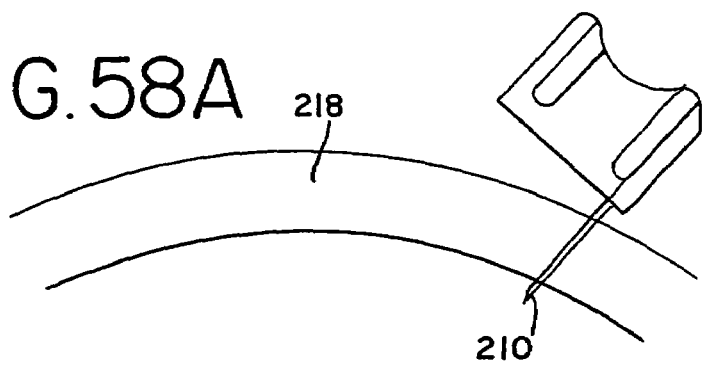
FIGS. 58A–58G illustrate the use of the instrument of FIG. 52 to form a transmural ablation.
Figure 58B:
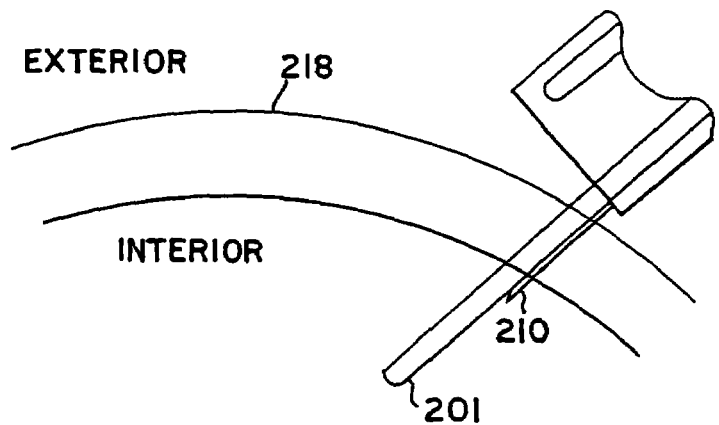
Figure 58C:
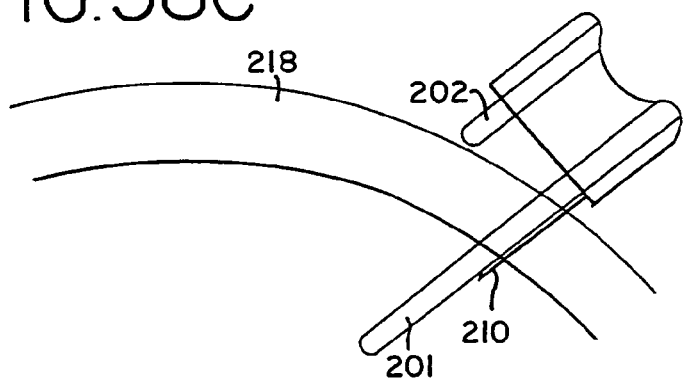
Figure 58D:
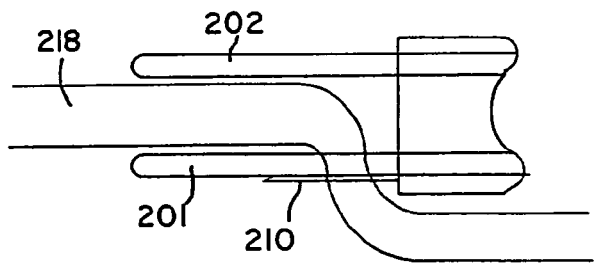
Figure 58E:
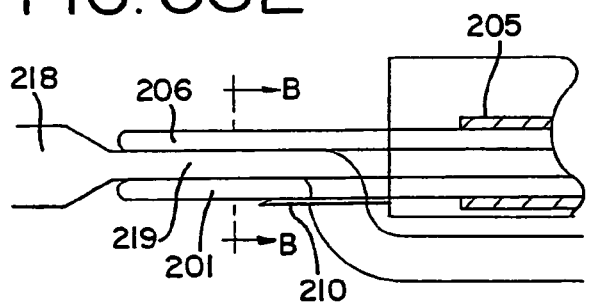
Figure 58F:
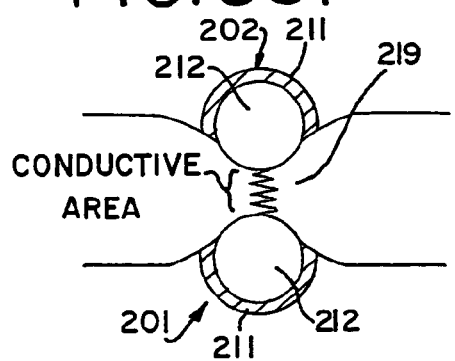
Figure 58G:
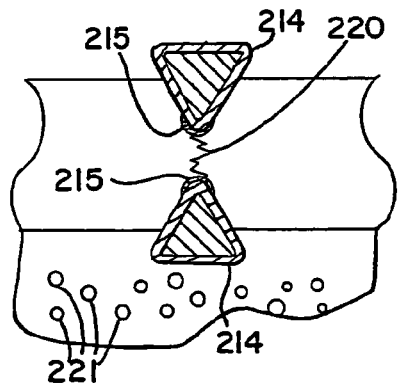

FIG. 58A shows the instrument used to penetrate the wall of a hollow organ, such as the heart. The slit needle 210 penetrates tissue through the wall of the atrium 218. In FIG. 58B, the inner wire electrode 201 is advanced through the puncture wound into the interior of the atrium. In FIG. 58C, the outer needle 202 is initially advanced onto the external surface of the atrial wall 218. FIG. 58D shows the inner 201 and outer 202 needles as they are simultaneously advanced along the inner and outer surfaces of the atrial wall 218. FIG. 58E shows the pusher tube 205 advanced to compress the tissue of the atrial wall 218 at location 219. RF energy is then applied between the conductive strips 212 on each electrode to ablate the compressed tissue 219. FIG. 58F shows section B—B of FIG. 58E, with the inner 201 and outer 202 electrodes compressing the tissue 219. The area of ablated tissue is shown as 220. The alternate electrode configuration of FIG. 5 is shown in FIG. 58G. Blood cells are represented as 221.

The compression of the tissue is important because it insures that the exposed electrode surface is not in contact with any tissue or blood except the clamped tissue to be ablated. Referring to FIGS. 58F and 58G one can see that the clamping of the tissue between the electrodes insures that only the conductive area is in contact with the clamped tissue. Especially important is avoiding any contact between the conductive area of the electrode and blood in the atrium. Contact between an active electrode and blood in the atrium is major cause of thrombus formation in ablation procedures. The compressed tissue acts to isolate the electrically active surface, and prevents inadvertent energy delivery to other parts of the heart or blood. The outside temperature of the electrode can easily be monitored to insure that the temperature of the insulation in contact with blood remains below a critical temperature (40° C., for example).

Figure 59:
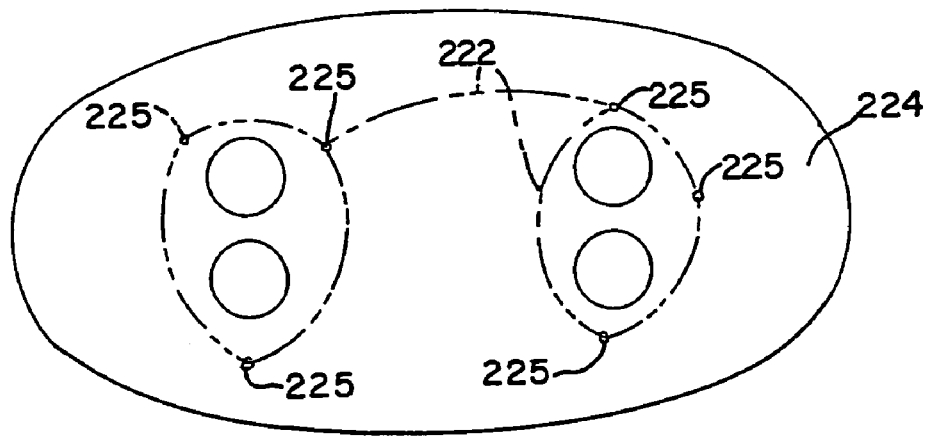
FIG. 59 shows a series of transmural ablations contemplated by the MAZE procedure.

FIG. 59 shows a potential series of continuous transmural ablation lines 222 located around the pulmonary veins 223 in the left atrium 224. A series of puncture wounds 225 are shown as one means to achieve the pattern of ablation lines (shown in dot-dash lines).

Figure 60A:
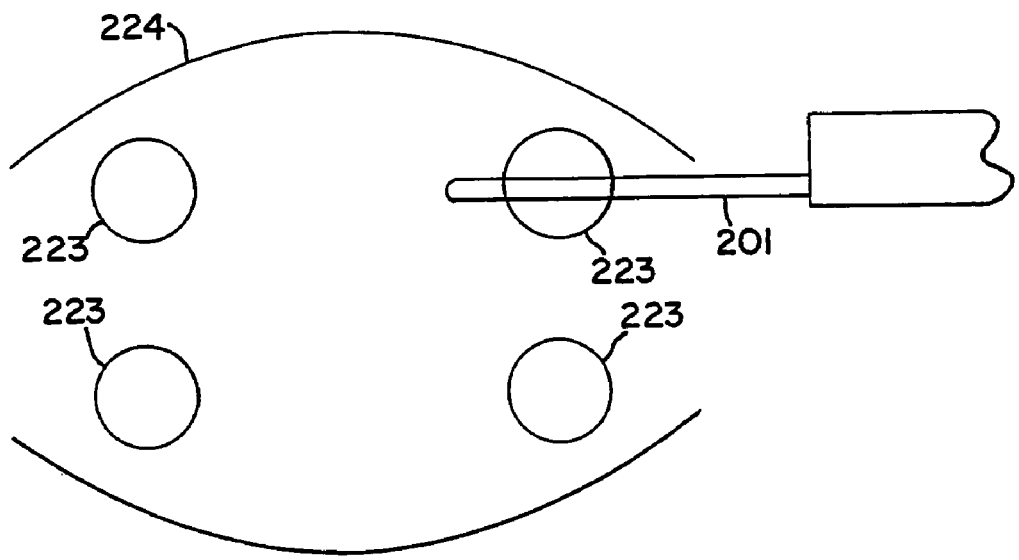
FIGS. 60A–60I illustrate a procedure for performing a circumferential lesion in lumen such as a pulmonary vein.
Figure 60B:
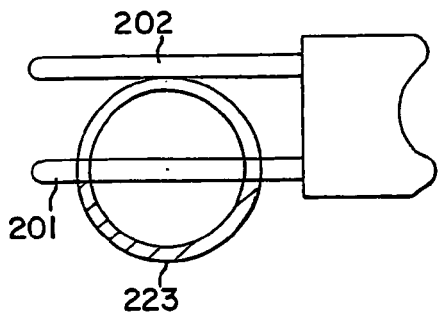
Figure 60C:
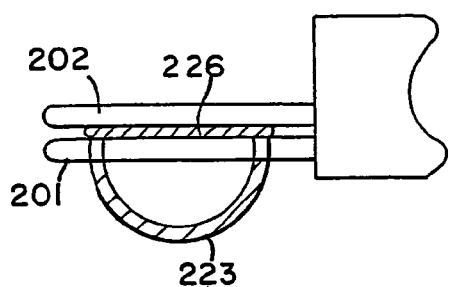
Figure 60D:
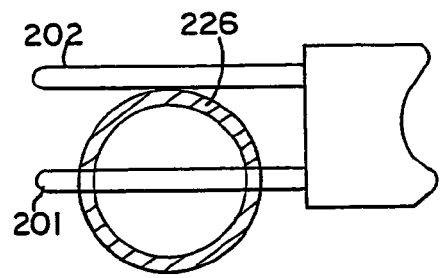
Figure 60E:
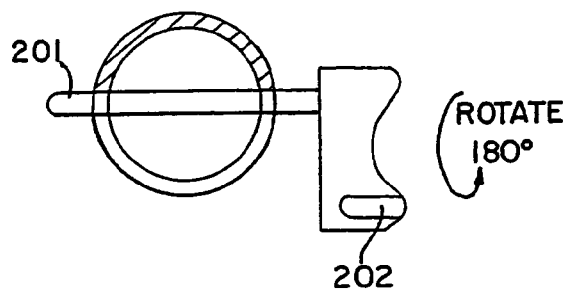
Figure 60F:
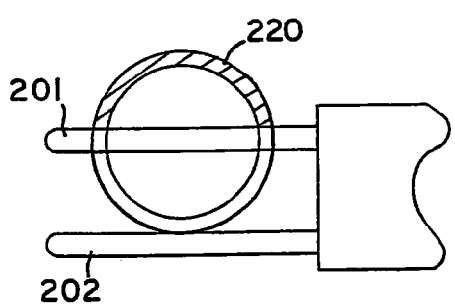

FIG. 60A shows a method for achieving a circumferential lesion in a pulmonary vein 223. The inner needle 201 is a piercing tip as shown in FIG. 56. The needle is advanced completely through the wall of the pulmonary vein until it exits the vein. In FIG. 60B, the outer electrode 2 is advanced parallel to the inner electrode 201. In FIG. 60C, the electrodes are compressed, and the compressed vein wall tissue 226 is ablated by applying RF energy between the two electrodes. In FIG. 60D, the electrodes are released, and the vein wall tissue 226 returns to its original shape. FIG. 60E shows the outer electrode 202 retracted back into the instrument body, and the instrument is rotated 180 degrees about the axis of electrode 201.

Figure 60G:
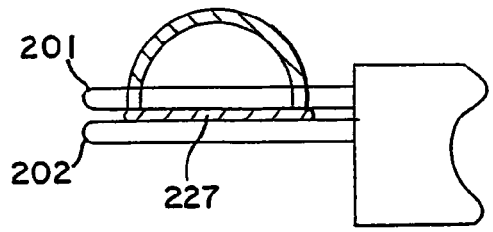
Figure 60H:
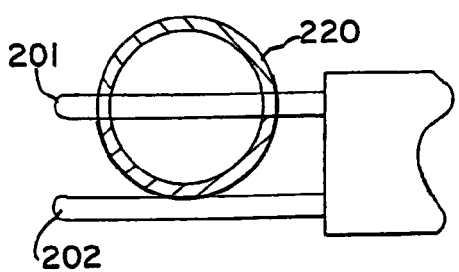
Figure 60I:
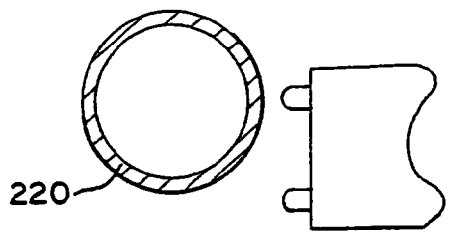

FIG. 6OF shows the outer electrode 202 advanced along the opposite side of the pulmonary vein from the ablated tissue 220. In FIG. 60G, the electrodes are compressed, and the compressed vein wall tissue 227 is ablated by applying RF energy between the electrodes. FIG. 60H shows the position of the electrodes with the pusher tube retracted, and the fully circumferential lesion 220. FIG. 60I shows the instrument retracted from the vein, and the circumferential lesion of ablated tissue 220.

FIGS. 61A–61J show the instrument used in a method to create a circumferential lesion around a pair of pulmonary veins 226 and 227. In FIG. 61A the inner electrode 201 is advanced into the side of the atrial wall 218, just below the ostium of the pulmonary vein 226 by advancing slider button 203. FIG. 61B shows electrode 201 and slider 203 fully advanced, and exiting the atrial tissue 218 just below the ostium of pulmonary vein 227. FIG. 61C shows outer electrode 202 advanced fully in parallel and to the same length as inner electrode 201 by advancing slider 204. Note that slider tube button 205 has advanced to its intermediate position.

FIG. 61D shows slider button 205 fully advanced, which clamps electrodes 201 and 202 together just below the ostia of the pulmonary veins on the side of the veins indicated by tissue surface 218a, and compresses the atrial wall tissue. RF energy is then applied between the two electrodes, and the clamped tissue 219 is ablated. In FIG. 61E, electrode 202 is retracted by retracting slider button 4. The line of ablated tissue is shown as 219a. This line of ablated tissue 219a will be completely continuous and transmural, and connect inner needle entry point 229 with inner needle exit point 230 and extend along the side of the atrial wall.

FIG. 61F shows the device body 207 rotated 180 degrees about the axis of the inner electrode 201 so that the atrial surface 218b on the opposite side of the pulmonary veins is exposed. FIG. 61G shows slider button 204 and outer electrode 202 advanced over the opposite surface of the atrium 218b. FIG. 61H shows slider button 205 advanced, and the electrodes 201 and 202 clamping the tissue 219b just below the ostia of the pulmonary veins 226 and 227 along atrial wall 218b. RF energy is then applied between the electrodes 201 and 202 to ablate the compressed tissue 219b. In FIG. 61I the slider button 205 is retracted, and the electrodes release the tissue 219b. The outer electrode is then retracted, exposing the tissue 219b that is now fully ablated as indicated by the line 219b. FIG. 16J shows a top view of FIG. 61I showing the continuous line of ablated tissue surrounding pulmonary veins 226 and 227, connected by entry point 229 and exit point 230 of internal electrode 201. The electrode is then retracted, leaving a continuous transmural lesion that electrically isolates the pulmonary veins from the rest of the atrial tissue.

In another embodiment of the invention, a penetrating compressive/tensile electrode is used. Once the jaws are positioned below the ostia of the pulmonary veins, the tissue is partially clamped, allowing continued flow from the pulmonary veins to the left atrium. An electrode needle is introduced which enters the left side of the atrial tissue and exits on the right side into a tip securing point on the lower jaw. This point will prevent the tip from moving axially when a needle is pushed. The lower atrial tissue can be compressed by "pushing" on the needle with a force that compresses tissue between the needle electrode and the lower jaw electrode. Bipolar RF energy is then applied between the needle and lower jaw electrodes to ablate a line of tissue from the needle entry to exit point. Once the lower atrial tissue has been ablated, the upper jaw is moved down to contact the tip of the lower jaw. Note that this still provides an open lumen for blood flow from the pulmonary veins to the left atrium. The needle is rotated 180 degrees on its axis so that the electrode surface faces up. The needle is then "pulled" to create tension, and exert a compressive force that compresses tissue between the needle electrode and the upper jaw. Bipolar RF energy is then applied between the needle electrode and upper jaw to ablate the tissue. Note that the partial closing of the upper jaw to contact the tip of the lower jaw could be done prior to compressing the lower atrial tissue.

Figure 62A:
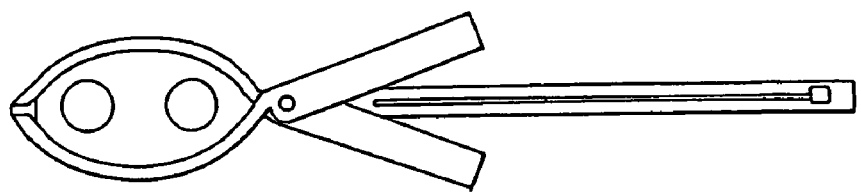
FIG. 62A–I show a further device for performing transmural ablations and the method for making such ablations.
Figure 62B:
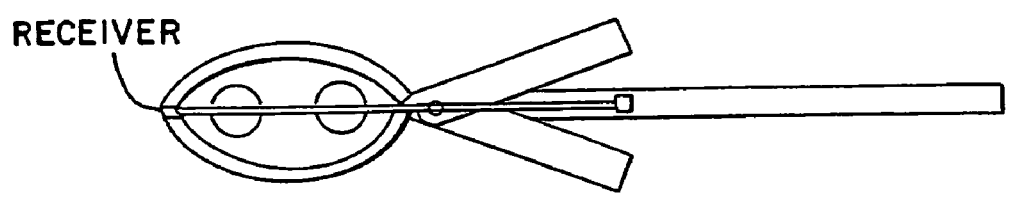
Figure 62C:
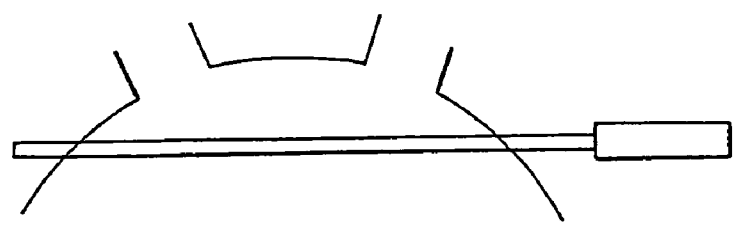
Figure 62D:
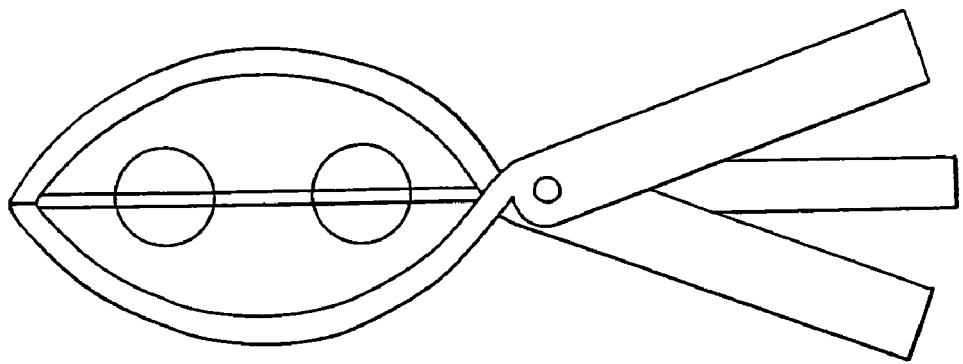
Figure 62E:
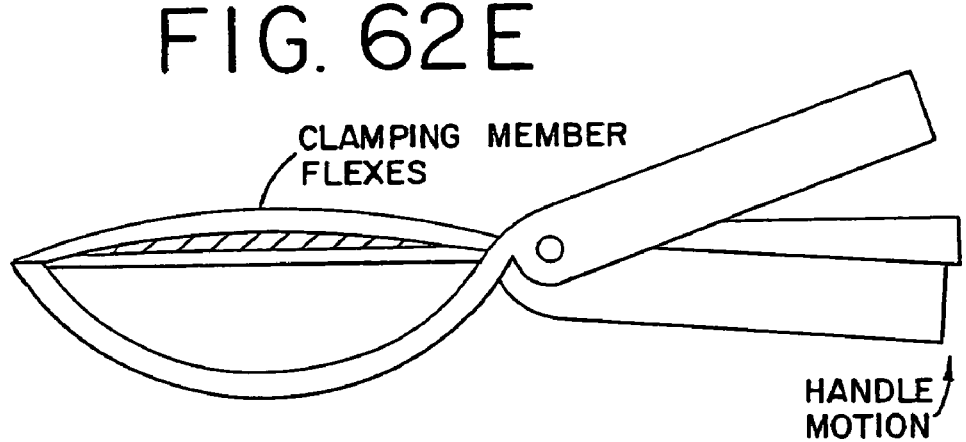
Figure 62F:
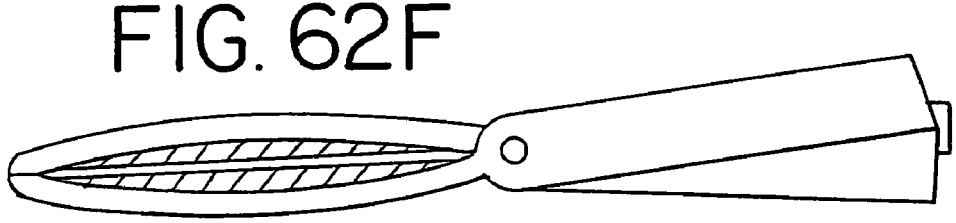
Figure 62G:
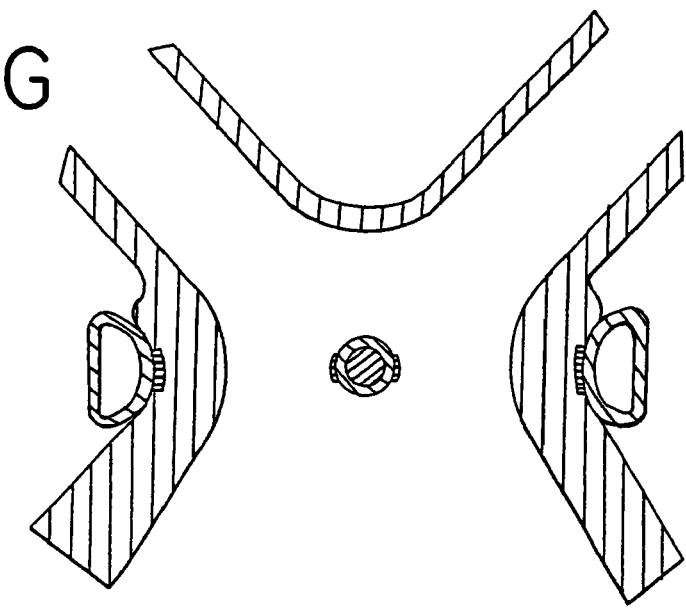
Figure 62H:
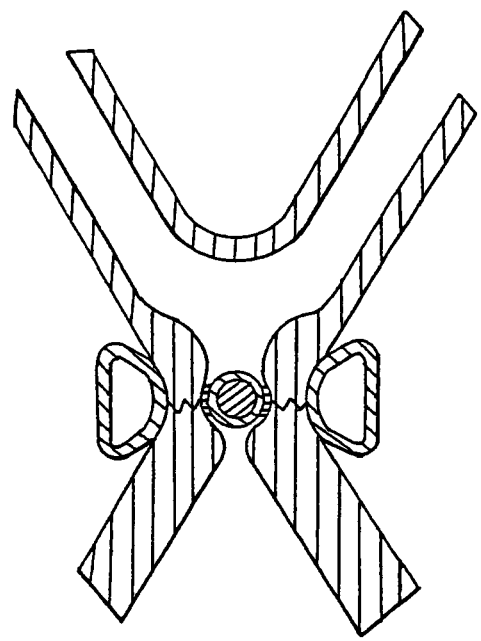

With reference to FIGS. 62A–62I the clamping apparatus as generally described above is shown. As illustrated, the device is a "pliers type" apparatus. The device is shown clamped around the atrial tissue below the ostia of the pulmonary veins. In FIGS. 62B–62D, an electrode needle is advanced through the atrial tissue to contact a receiver at the tip of the device. FIG. 62E shows one method of clamping the tissue to a rigid needle electrode, using a non-rigid outer clamping member that flexes either by further motion of the handle as shown or by further extension of the electrode member. FIG. 62F shows both sides of the clamping member flexed, and the tissue compressed between. FIG. 62G shows the position of the clamping members and electrode prior to tissue clamping. FIG. 62H shows these positions during tissue clamping. Bipolar RF energy is applied between the clamping members, and the inner electrode to ablate the atrial tissue, creating a lesion, as shown in FIG. 62H. Note also, that if the inner electrode had only one exposed electrode surface, the tissue ablation could be carried out first on one side, then the other, without occluding the lumen between the pulmonary veins and the atrium.

Figure 62I:
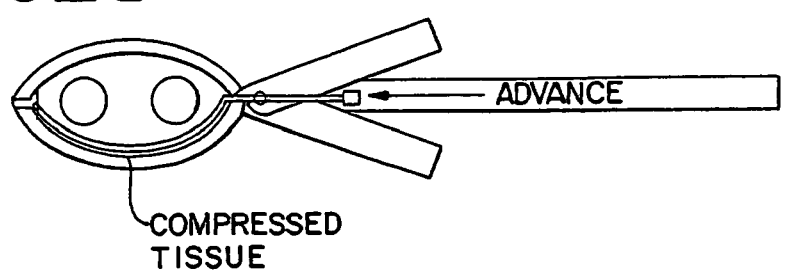

FIG. 62I shows another way to achieve tissue compression by advancing a relatively flexible needle electrode which bends as shown to compress the tissue between the electrode and one of the device jaws.

A further aspect of this invention provides three methods which may be used to gain access to ablate cardiac tissue. The first method gains access to the heart by opening the patient's chest or thoracic region. The second method gains access to the heart by intercostal incisions whereby access to the heart is achieve between the ribs. Finally, the third method utilizes a sub-xyphoid approach. In any event, each method is adapted to place the ablations at previously identified locations that require ablation.

Figure 68:
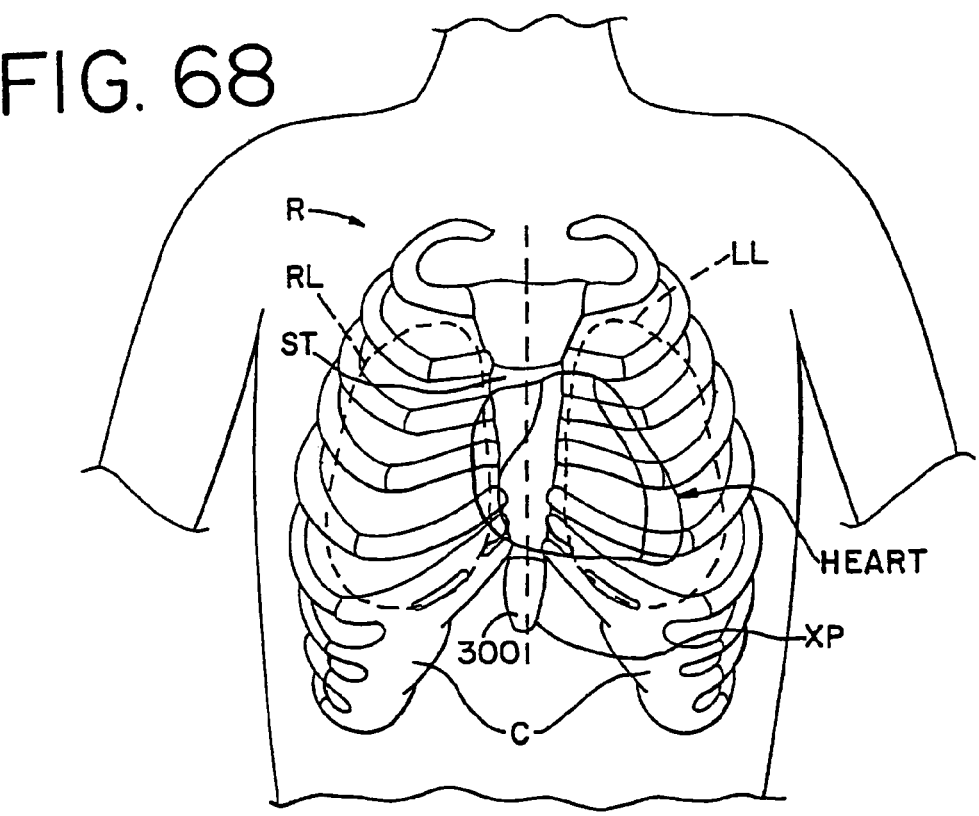
FIG. 68 shows an anterior plan view of the heart in the chest cavity and an access location for performing ablation where the chest cavity is opened.
Figure 69:
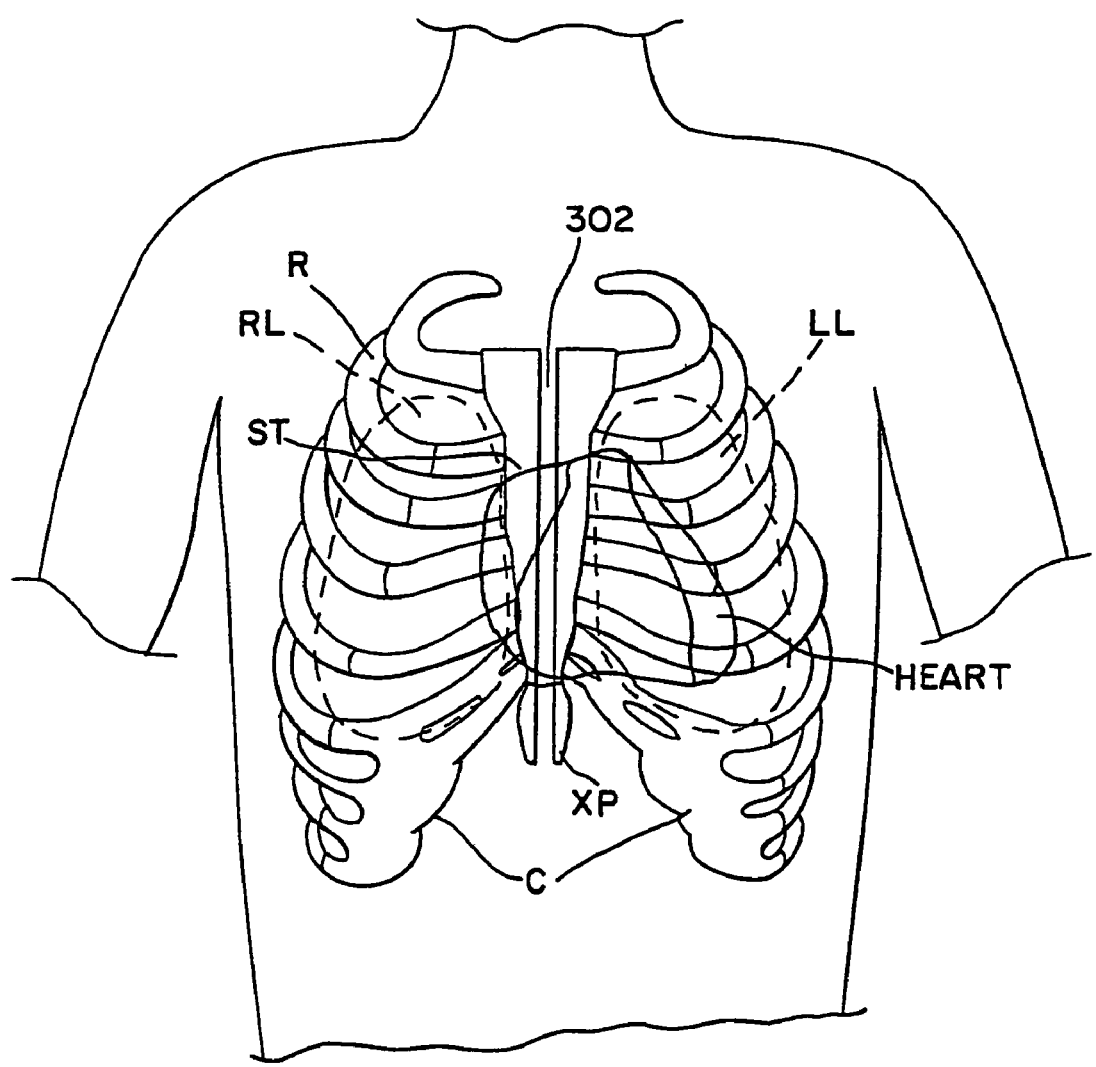
FIG. 69 shows an anterior plan view of the heart with an opening in the chest cavity.
Figure 71:
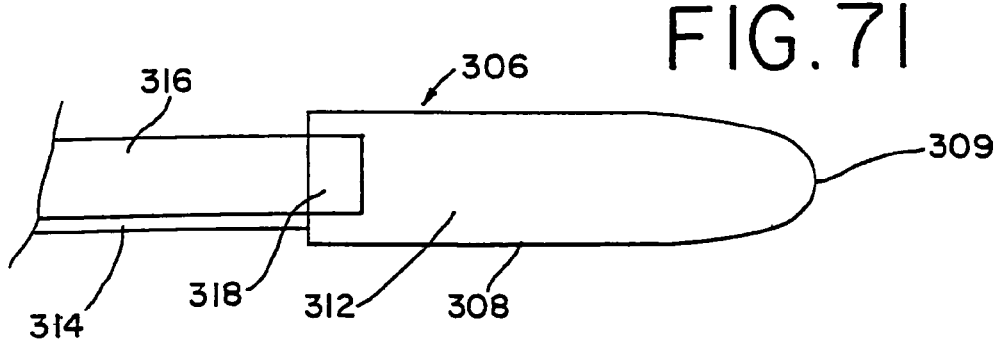
FIG. 71 shows an enlarged side view of the bullet dissector.
Figure 72:
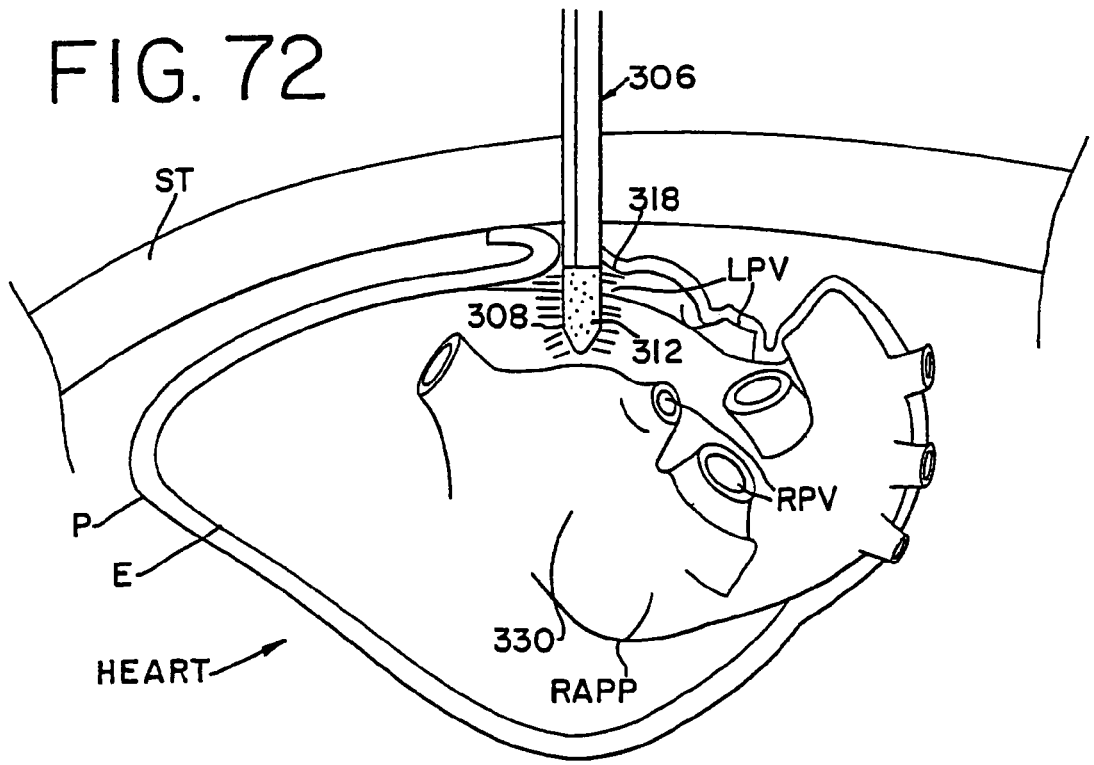
FIG. 72 shows an enlarged side view of the opened chest cavity including a bullet dissector.
Figure 73:
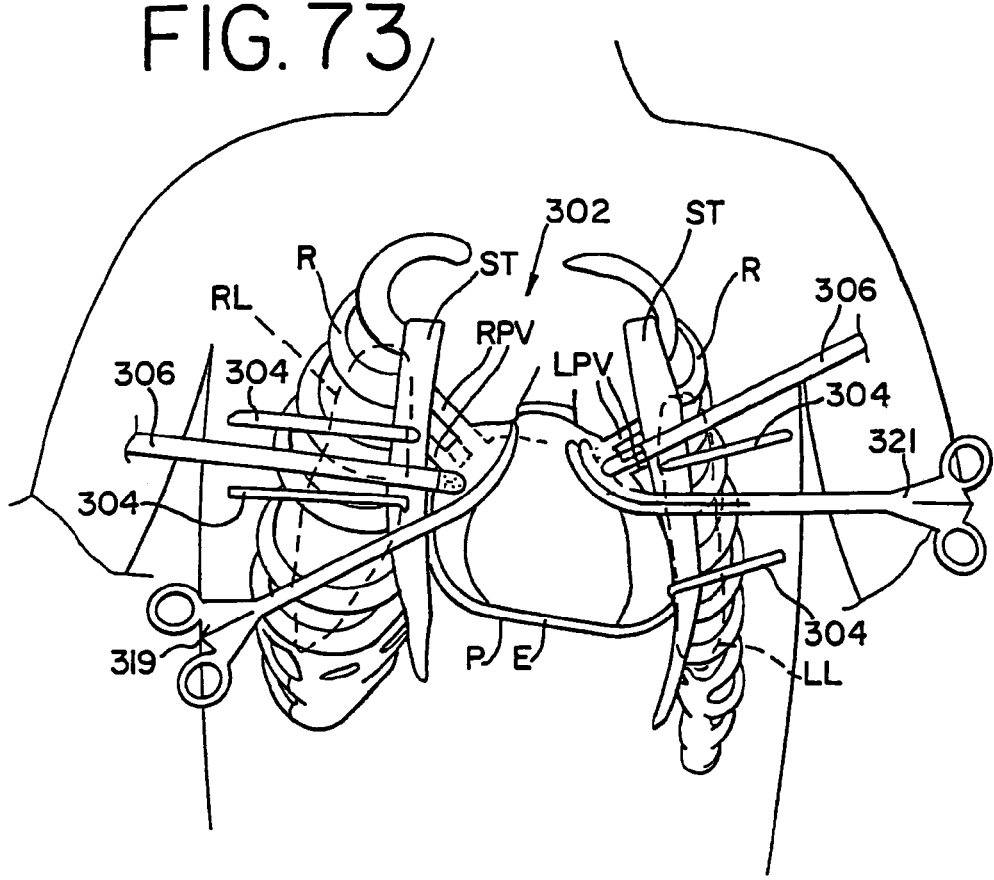
FIG. 73 shows an anterior plan view of the chest cavity showing ablation according to the open heart method.

The first method is illustrated in FIGS. 68–77. Access to the patient's heart is achieved by opening the patient's chest. FIGS. 68–77 show a patient's rib cage R, sternum ST, xyphoid XP, coastal cartilage C, right lung RL and left lung LL. This method requires a gross thoracotomy such as where the ribs or sternum are cut in half with an anterior incision or removal of a portion of the ribs or sternum such as in the form of a median sternotomy. Percutaneous penetration is made by an initial incision into the patient's chest above the sternum. In FIG. 68, percutaneous penetration is made in the longitudinal direction along the patient's sternum along line 300. Thereafter, the sternum is cut longitudinally and each side of the sternum pushed apart so as to gain access to the patient's thoracic or chest cavity 302, as shown in FIGS. 69 and 73. Spreading of the sternum and ribs is achieved using a well known spreading device or the like. If the lungs are not deflated then they will need to be moved aside using clamps 304 or the like to gain access to the heart. Once access to the heart is cleared, all ablation locations must be located and identified.

Figure 70:
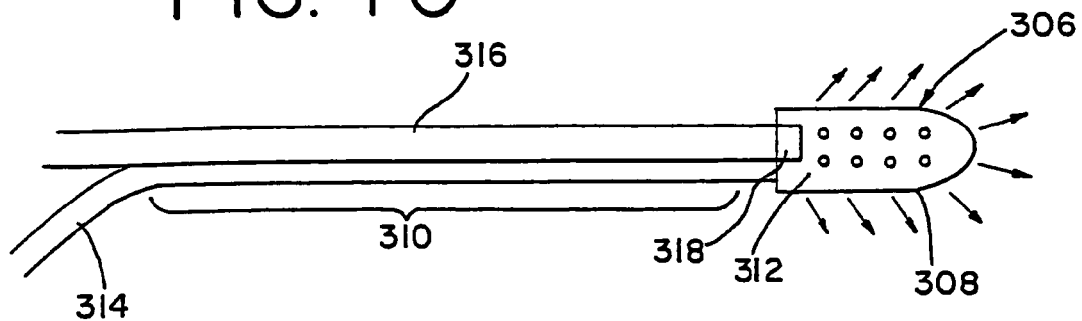
FIG. 70 shows a side view of a bullet dissector according to the present invention.

Locating and identifying the ablation locations may be performed by one of several different instruments such as a bullet dissector 306, which is best shown in FIGS. 70 and 71. The bullet dissector 306 identifies a location which requires ablation and creates a viewing and working space from which to ablate the location. The bullet dissector includes a bullet or head 308 and a body 310. The head 308 is made of a clear or transparent material and has a plurality of irrigation holes 312. The body 310 includes a tube 314 which supplies saline to the head 308. As saline is supplied through the tube 314 to the head 308, it flows out of the irrigation holes 312, as indicated by the arrows in FIG. 70. The body 310 of the bullet dissector may be attached to an endoscope 316 or other suitable device, which includes a light or fiberoptic cable 318 to illuminate the site being dissected. The size of the endoscope to which the bullet dissector is attached may vary although the preferred diameter range is between 2 mm to 10 mm. The diameter of the endoscope is approximately equal to or smaller than the diameter of the dissector head. The endoscope is preferably connected to the rear of the dissector head. A portion of the endoscope cable 318 may be inserted into the dissector head 308 while maintaining seal around the cable so that saline flow is unaffected. The endoscope may include a viewing lens or camera which is connected to a video monitor which displays the location which is viewed.

The continuous flow of saline from the bullet dissector 306 allows the saline to flush blood and other body debris from the transparent head 308 and endoscope viewing lens so as to provide a clear viewing space. As saline flows out of the head, the flow of saline pushes against the adjacent tissue and aids in dissection by, for example, separating the pericardium from the heart. The continuous flow of saline creates a working space between the dissector and the surrounding tissue and ensures that this space is positively pressurized.

In addition, the head 308 of the bullet dissector also may be designed to allow easy dissection around the pulmonary veins or other cardiac tissues. The head 308 is bullet shaped. It has a rounded distal tip 309 which gently separates or dissects tissue. The diameter of the head 307 may be equal to or larger than the body 310.

Once the thoracic cavity is accessible, the bullet dissector 306 is inserted into the patient's chest cavity adjacent the heart, as shown in FIG. 72. The bullet dissector 306 may locate the ablation locations over a pericardium P. Alternatively, the pericardium may be pierced so as to contact an epicardium E so as to allow the bullet dissector to directly contact the surface of the heart. The bullet dissector assists the identification and location of ablation locations. Saline exits the irrigation holes 312 of the bullet dissector 306 and insufflates the intrapericardial space around the ablation location. Insufflating the ablation location with saline creates a viewing and working space within the intrapericardial space 318 by which the ablation location may be accessed. Saline also clears blood away from the ablation location and creates a positive pressure in the working space. A positive pressure may be particularly helpful in eliminating the need for complicated hemostatic devices or valves, and/or avoiding or limiting the need to seal off the pericardial incision by a valve, balloon or other inflation device. Insufflating can be done with any compatible biological fluid: saline, contrast medium, CO2, or blood. However, saline or CO2 is preferred because these provide clarity with which to view the space and identify the area to ablate. Excess saline may exit the intrapericardial space and can be removed by a drainage tube which can be inserted into the chest cavity.

After the ablation locations are located and identified, the ablation or clamping device is then introduced into the patient's chest and positioned in contact with the location. The ablation device which is generally used for the open heart procedure is the grasper shown and described in FIGS. 28–32 although use of other graspers or devices is also contemplated. The ablation device also may have a shape which is particularly suited to the ablation location to be contacted. During insertion of the ablation device, the bullet dissector preferably remains inserted so as to maintain the positively pressurized working space and to assist in visualizing the ablation device. Thereafter, the location is ablated using an RF energy ablation technique as disclosed herein.

In FIG. 73 cardiac tissue is ablated from both the right and left sides. FIG. 73 shows ablation of the left atrium in the region of the right and left pulmonary veins, RPV and LPV, respectively. The right pulmonary veins RPV are ablated using a grasper 319 such as the one shown and described in FIGS. 28–32. The left pulmonary veins LPV are ablated using a similar grasper 321 which is rotated 180 degrees. Jaw members of each grasper 319, 321 may be curved and oriented such that the concave portion of the jaw members face the pulmonary veins and the convex portion of the jaw member face away. This orientation is preferred to provide effective clamping and ablation of the atrium near the pulmonary veins. Because the patient's chest is open, the graspers may be in the form of open scissors such as, for example, the grasper shown in FIGS. 28–32, or an ablation device with sliding jaws generally illustrated in FIGS. 1–27 or of the type shown in FIGS. 33–37. It is contemplated that different ablation devices may be used to effectively ablate different cardiac tissues.

Figure 74:
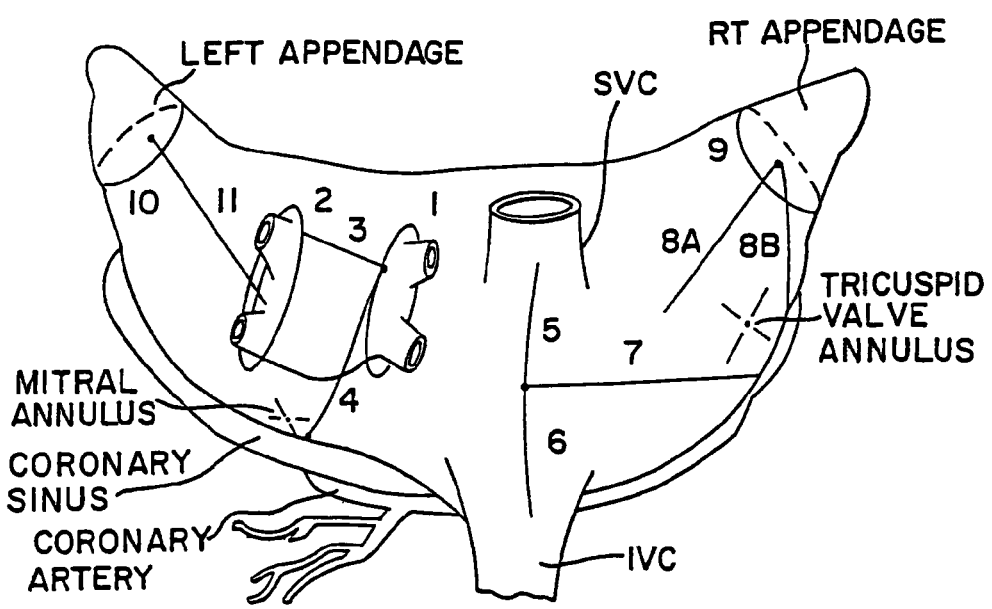
FIG. 74 illustrates ablations to the right and left atrium as seen from behind.
Figure 75:
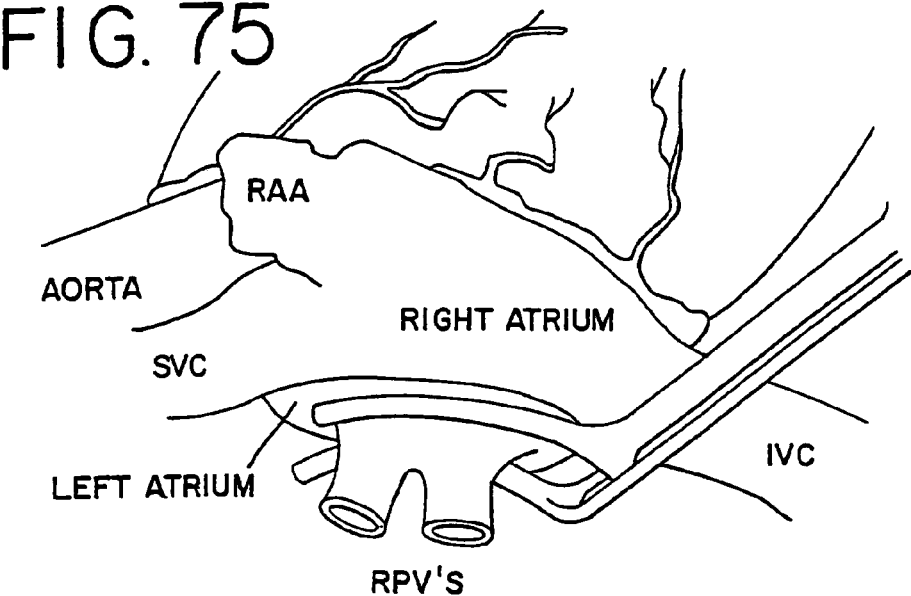
FIGS. 75–76 illustrates bilateral ablation of the left atrium near the right and left pulmonary veins.
Figure 76:
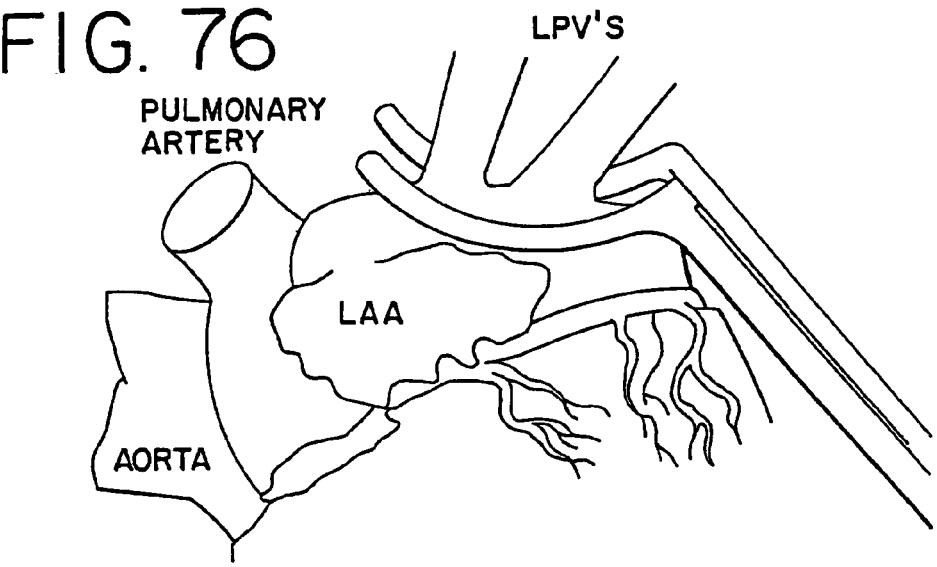

FIG. 74 shows eleven different locations that may be ablated in treating atrial fibrillation according to any of the methods described herein. By way of example, FIGS. 75–76 show ablation of an epicardial surface adjacent the left and right pulmonary veins, LPV and RPV, respectively. In FIGS. 74–77, the referenced portions of the heart include the right atrial appendage RAA, left atrial appendage LAA, left atrium, superior vena cava SVC, inferior vena cava IVC.

Figure 77:
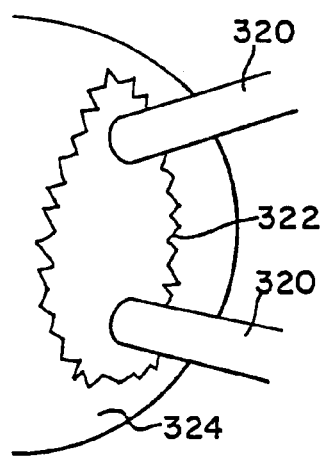
FIG. 77 illustrates a schematic diagram of the heart with ablations according to the methods of the present invention.

FIG. 77 shows bilateral ablation near a pair of pulmonary veins 320 by creating an ablation lesion 322 on the left atrium 324. Bilateral ablation creates a circumferential ablation lesion on the atrium which isolates the pair of pulmonary veins.

Figure 78:
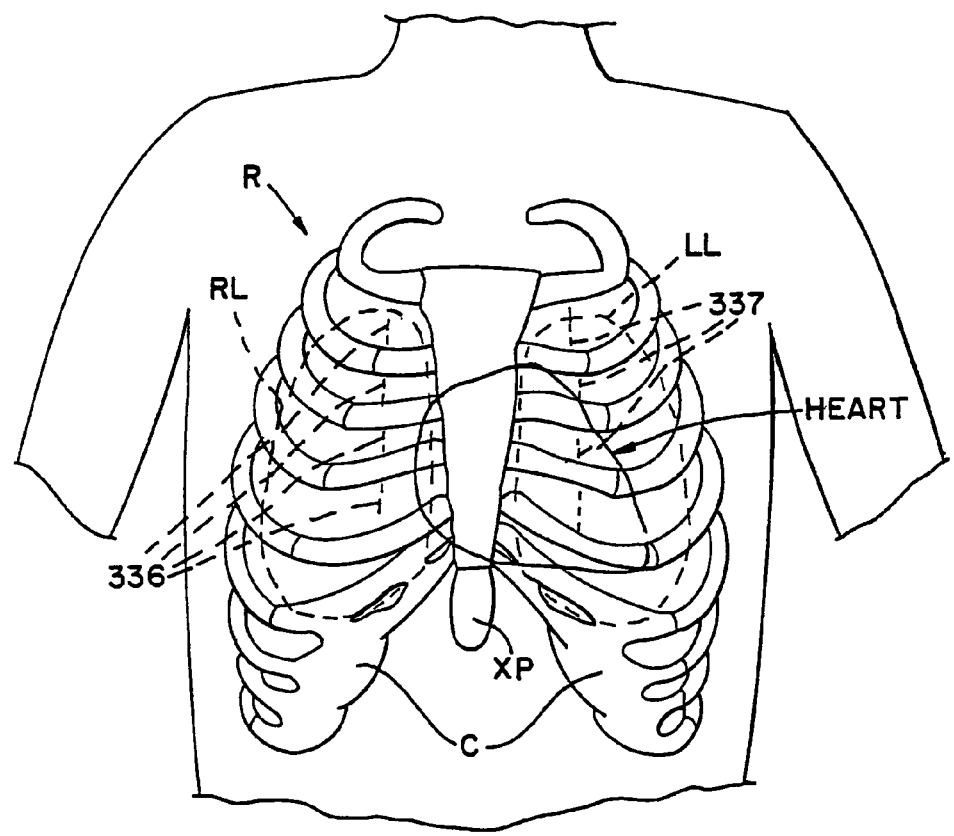
FIG. 78 is an anterior plan view of the heart and access locations for performing ablation according to the intercostal method.

FIGS. 78–86 illustrate the second method which achieves access to the heart using a percutaneous intercostal penetration with like parts referenced with like letters and numbers. This method is less invasive than a gross thoracotomy. In FIG. 78, one or more percutaneous intercostal penetrations may be made in one or more access locations 336, 338 between the ribs. The direction and location of the percutaneous intercostal penetrations will depend on where the cardiac tissue to be treated is located, so that ablation of the cardiac tissue is accessible by an appropriate ablation device. For example, entry through access locations 336 is helpful in achieving access to ablation locations located on the right side of the heart and, likewise, access locations 337 achieve access to the left side of the heart. For most, if not all, intercostal penetrations the lung may be temporarily deflated to allow easier passage of the instrument through the pleural space PS, although such deflation may not be absolutely necessary. One or more suitable access devices may be used to obtain access to the intercostal spaces between the ribs. These devices may be used to protect the incision location and minimize trauma thereto and may include, but are not limited, to trocar sleeves, ports, or other types of percutaneous access cannulae. By way of example, not limitation, FIGS. 79–86 shows a supporting ring 338 with tensioning members 340.

Figure 79:
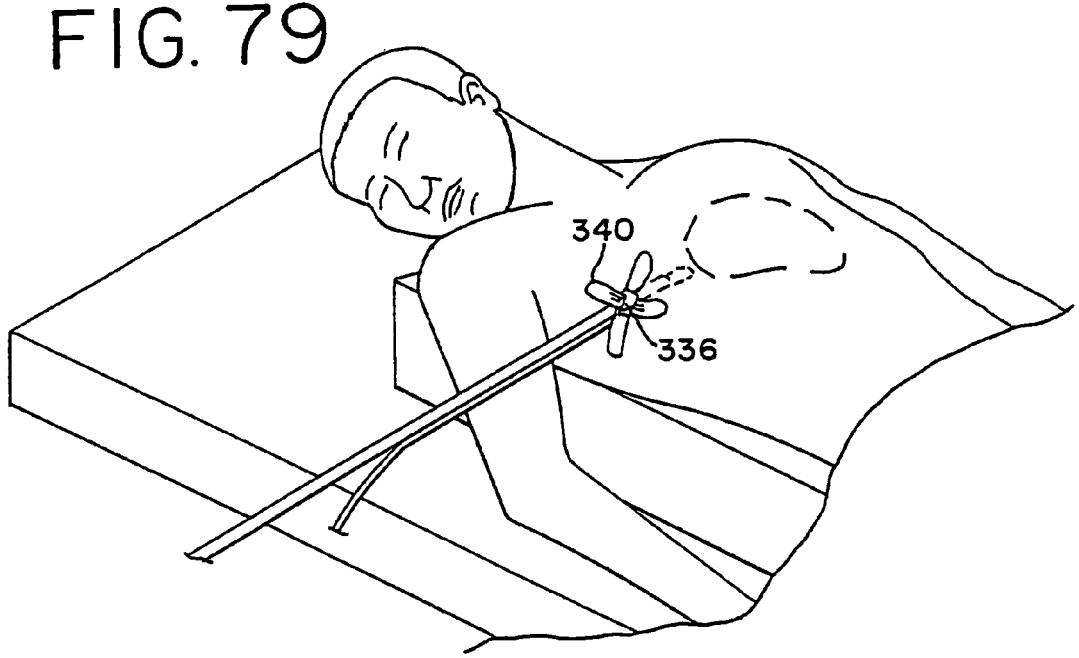
FIG. 79 is a top perspective view of the patient showing intercostal insertion of the bullet dissector into the chest cavity.
Figure 80:
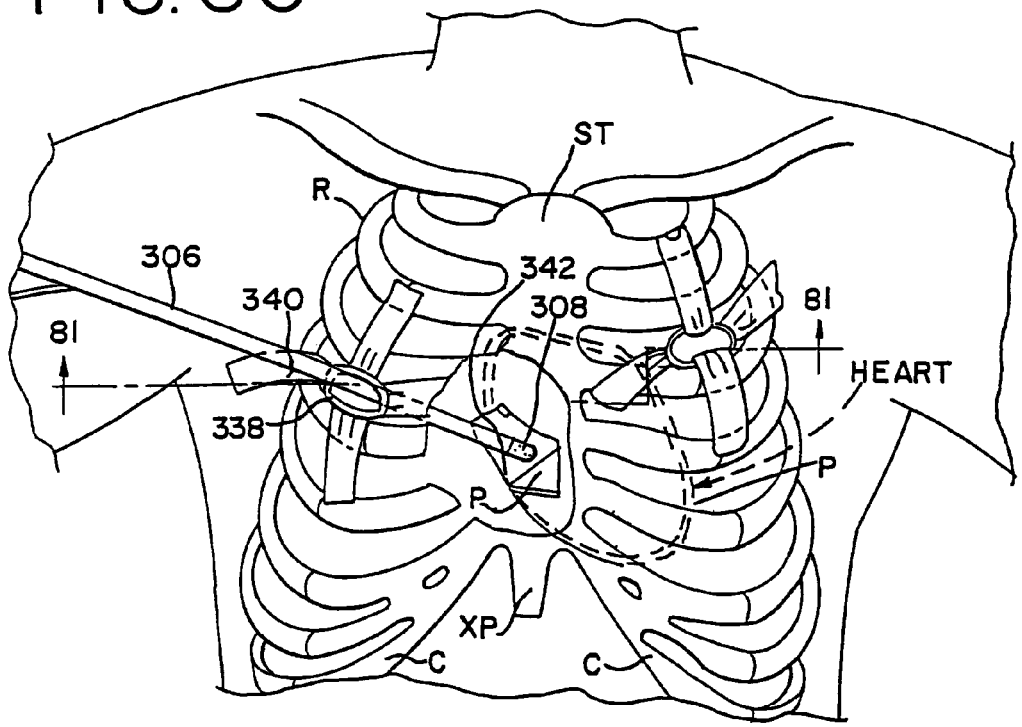
FIG. 80 is an anterior plan view of the heart showing intercostal insertion of the bullet dissector into the intrapericardial space.
Figure 81:
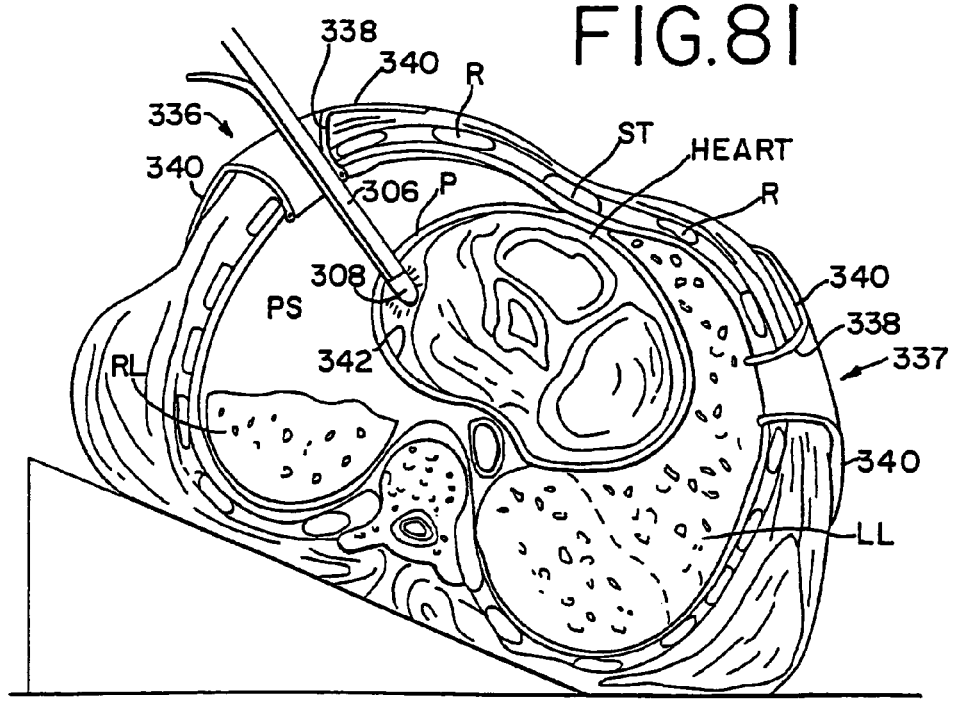
FIG. 81 is a sectional view along plane 81—81 of FIG. 80.
Figure 82:
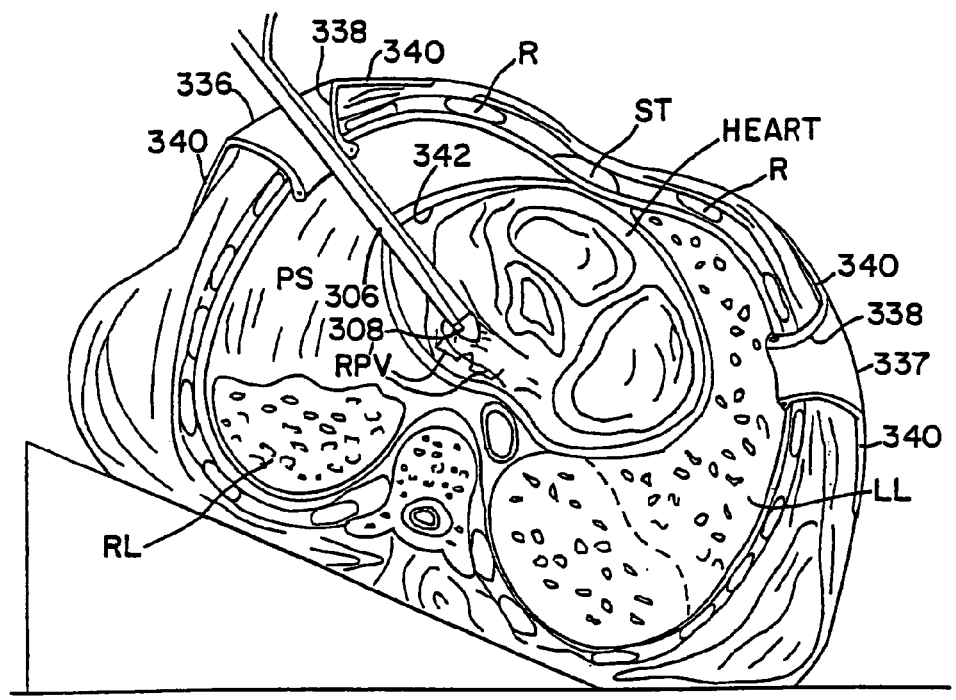
FIG. 82 is a sectional view, similar to FIG. 81, showing insufflation of the bullet dissector.
Figure 83:
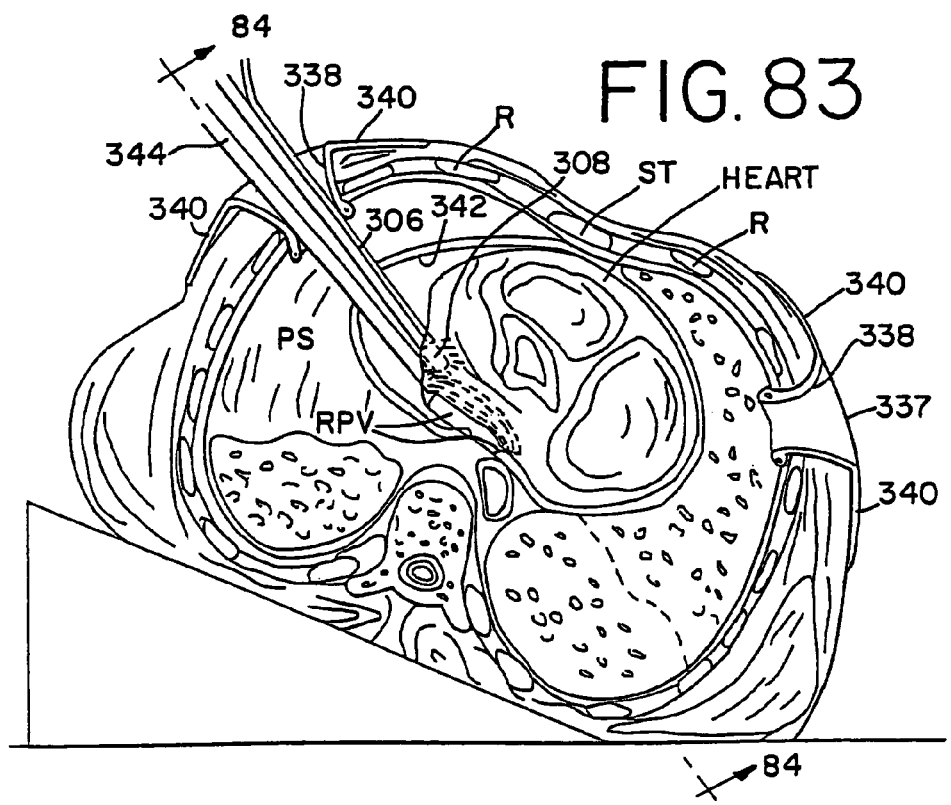
FIG. 83 is a sectional view, similar to FIG. 81, showing insertion of an ablation device.

Once the intercostal penetration is made, the bullet dissector is introduced through the incision, as shown in FIG. 79. Turning to FIG. 80, the pericardium P is preferably pierced or punctured so as to allow the head 308 of the bullet dissector 306 into an intrapericardial space 342. FIGS. 81–83 illustrate intercostal ablation where the right lung RL is deflated and the left lung LL remains inflated. As a result, the bullet dissector traverses the pleural space PS on its path to the heart. The bullet dissector insufflates the intrapericardial space 342 with saline and creates a clear working space which is positively pressurized in relation to the pressure outside the pericardium. The dissector is preferably attached to an endoscope or like device which allows for viewing of the ablation location and is inserted into the intrapericardial space 342 until an ablation location is located. Then the ablation device 344 is inserted into the incision and advanced to the ablation location.

FIG. 83 shows the ablation device 344 ablating cardiac tissue adjacent the right pulmonary veins RPV. By way of example but not limitation, the ablation device for the intercostal and sub-xyphoid methods may be the graspers shown and described herein in FIGS. 33–37 or FIGS. 63–65. Different ablation devices may be used for reaching different areas of cardiac tissue. The ablation devices may have different curvatures for reaching certain portions of the heart. For example, an ablation device for the left atrium adjacent the left pulmonary veins may have a different curvature than the ablation device for the right atrium adjacent the right pulmonary veins. FIGS. 83A and 83B show right and left curved graspers 350 and 352, respectively, which are similar to the grasper in FIGS. 33–37 except that the graspers in FIGS. 83A and 83B have right and left curved jaw members 354 and 356, respectively. Both the right and left curved graspers 350 are helpful in ablating cardiac tissue adjacent the right and left pulmonary veins depending on what direction of approaches are used. Likewise, the left curved grasper 352 assists in ablating cardiac tissue adjacent the left pulmonary veins. Other shapes of ablation devices will be apparent to those skilled in the art. It is noted that the intercostal and sub-xyphoid methods preferably will utilize ablation devices having a long handle such that when the instrument reaches the ablation location a gripping portion of the device remains outside the entry location into the patient for control by the doctor.

Using the intercostal method, transmural ablations may be performed on other cardiac tissue using RF energy, as previously described herein. Ablation is repeated until all ablation locations have been treated. Ablation devices may be inserted into different access locations 336 depending on which directional approach is preferred for the cardiac tissue which requires ablation. Different ablation devices may be inserted depending on which cardiac tissue requires treatment. Once all areas are treated on the right side in FIG. 83 with the appropriate ablation device, the right lung is re-inflated and the access location 336 is closed. The method is repeated for the left side if necessary through access location 337. FIG. 84 shows ablation of cardiac tissue adjacent the left pulmonary veins LPV.

Figure 85:
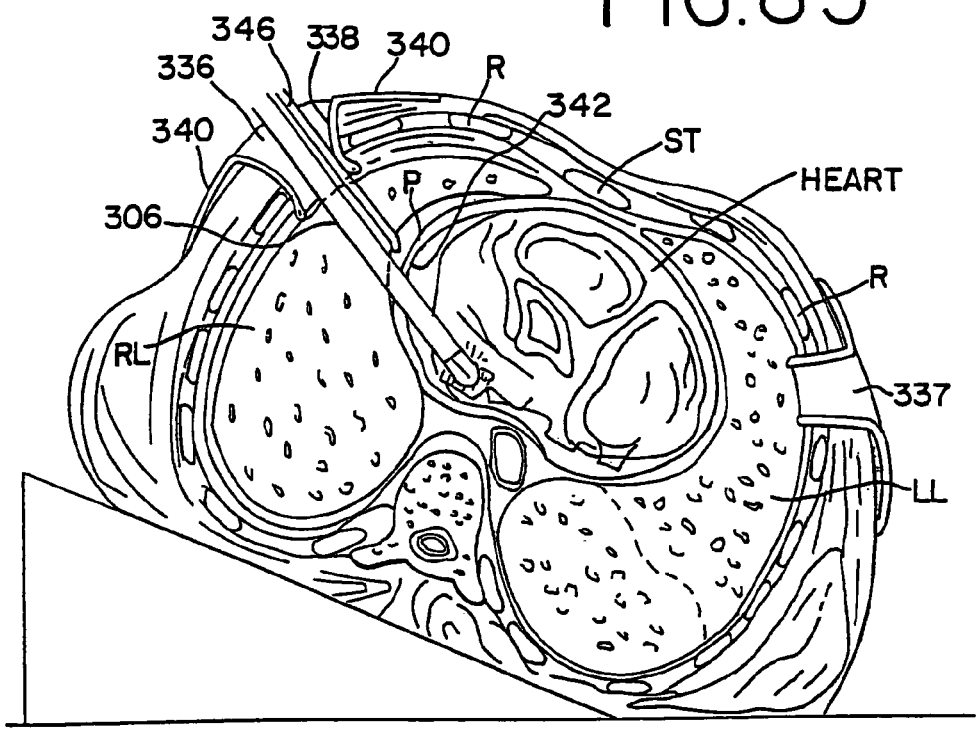
FIGS. 85–86 are sectional views, similar to FIG. 81, showing intercostal ablation being performed with the lungs inflated.
Figure 86:
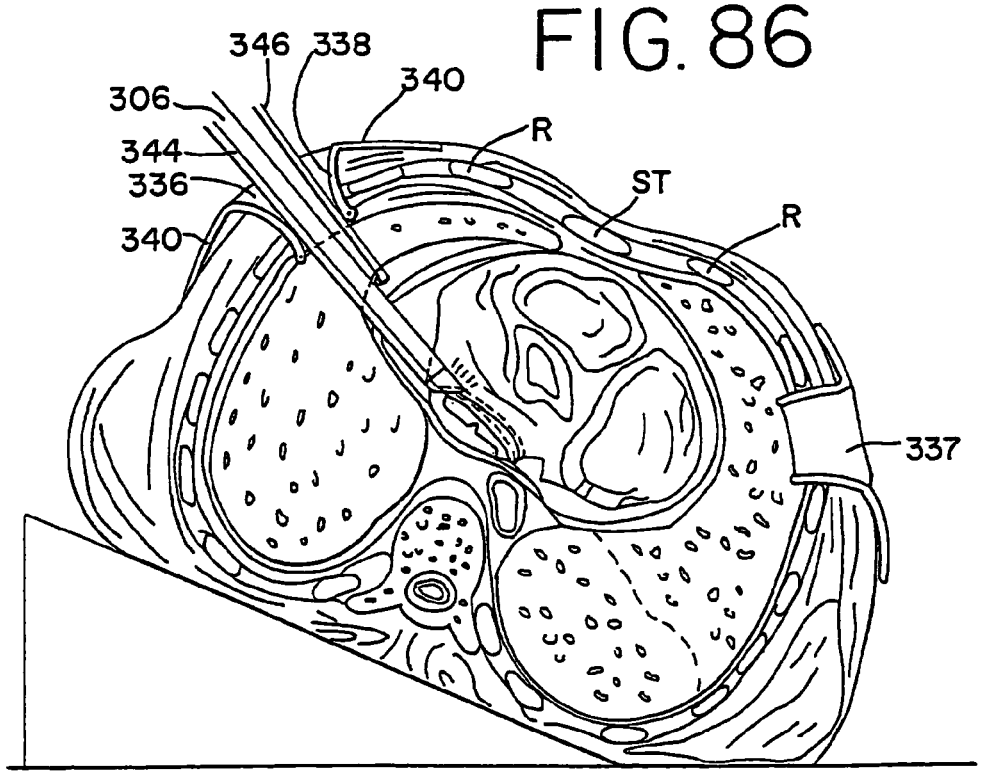

FIGS. 85 and 86 show intercostal ablation which occurs while both lungs are inflated. It may be necessary to use clamps 346 or the like to pull portions of the lung away from the heart and provide a pathway for advancing the bullet dissector 306 and the ablation device 344. While both lungs remain inflated, it is possible that cardiac tissue may be treated from both sides of the chest, at the same time, with one dissector 306 and one ablation device 344 within the access location 336 and another dissector and ablation device within the access location 337.

Figure 87:
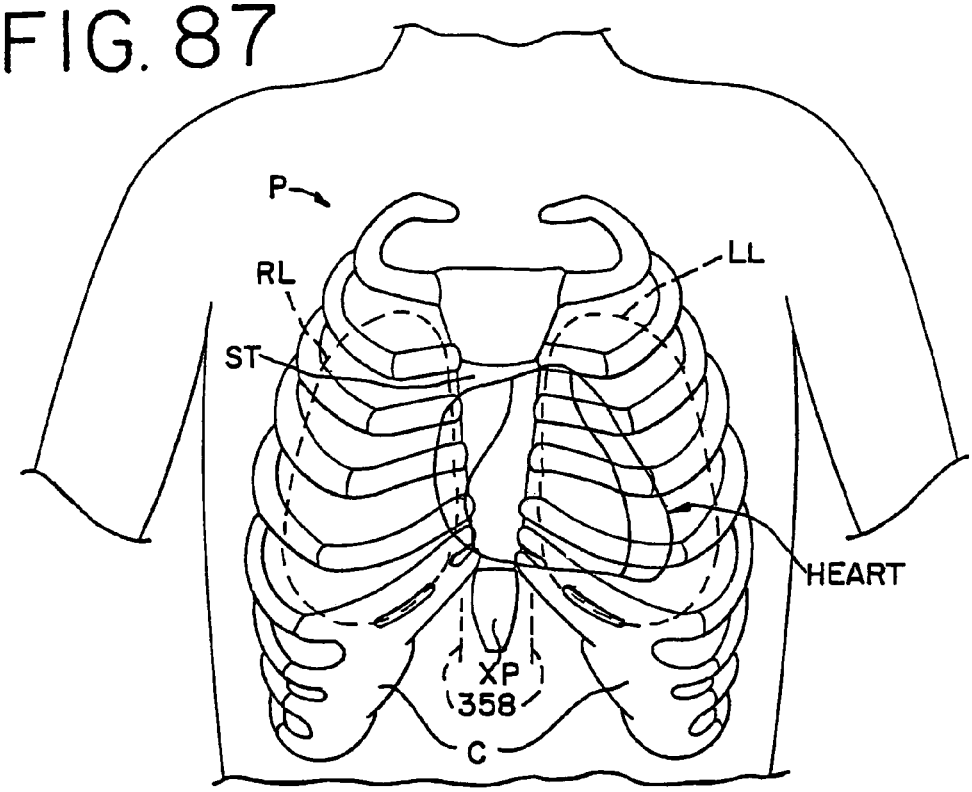
FIG. 87 is an anterior plan view of the heart and access locations for performing ablation according to the sub-xyphoid method.
Figure 88:
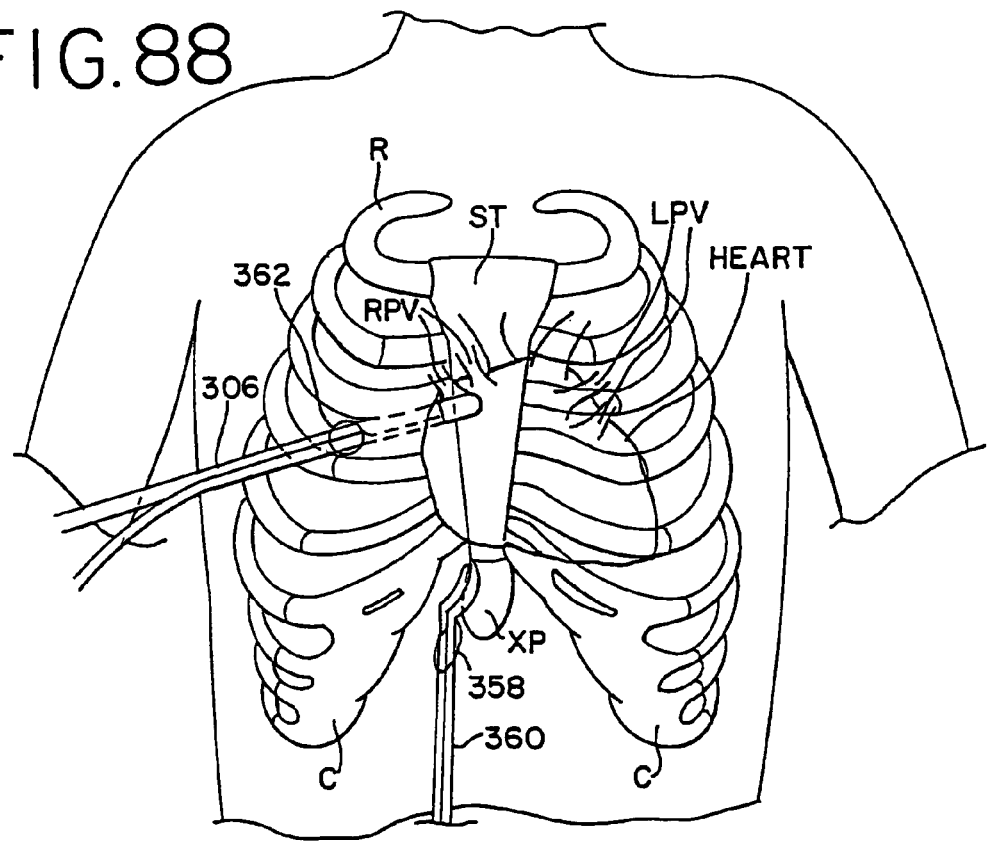
FIG. 88 is an anterior plan view of the heart showing insertion of the bullet dissector and ablation device according to the sub-xyphoid method.
Figure 89:
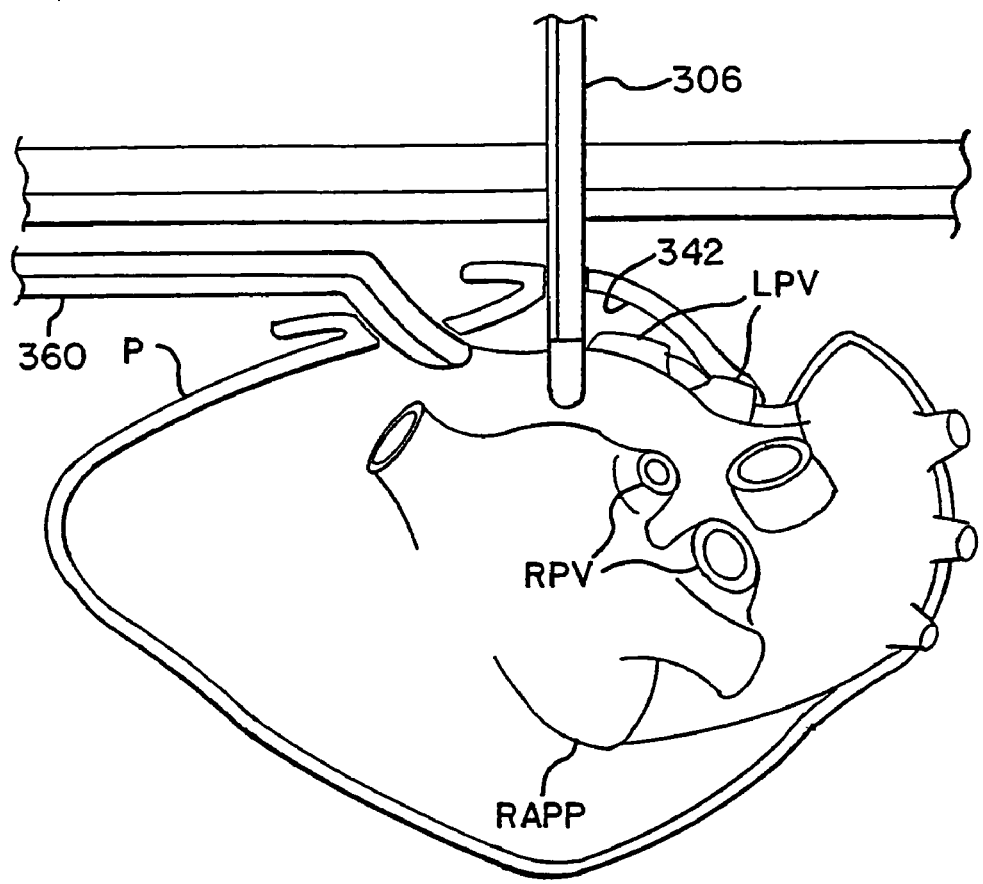
FIG. 89 is an enlarged side view of the heart showing an ablation device inserted according to the sub-xyphoid method.
Figure 90:
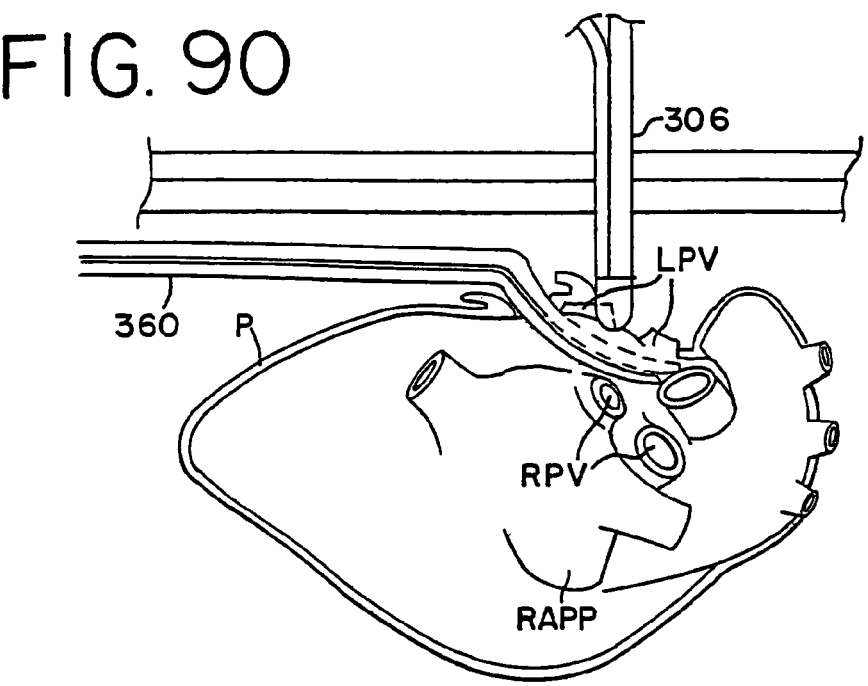
FIG. 90 is an enlarged side view of the heart showing ablation according to the sub-xyphoid method.

In the sub-xyphoid method, the initial incision is made beneath the rib cage R, preferably between the xyphoid XP and the adjacent costal cartilage C. In FIGS. 87–91, like parts are again shown with like letter and number. FIG. 87 shows access locations 358 for the incision. In FIGS. 88–91, the ablation device 360 is advanced through the percutaneous sub-xyphoid penetration to the aberrant cardiac tissue which requires ablation. In FIGS. 88–90, the bullet dissector 306 may then be inserted through a percutaneous intercostal penetration 362 to identify the ablation location and assist in guiding the ablation device. Insufflation from the dissector 306 creates the positively pressurized and clear working space. Thus, the cardiac tissue may be easy located and ablated with the ablation device 360, as shown in FIGS. 89 and 90.

Figure 91:
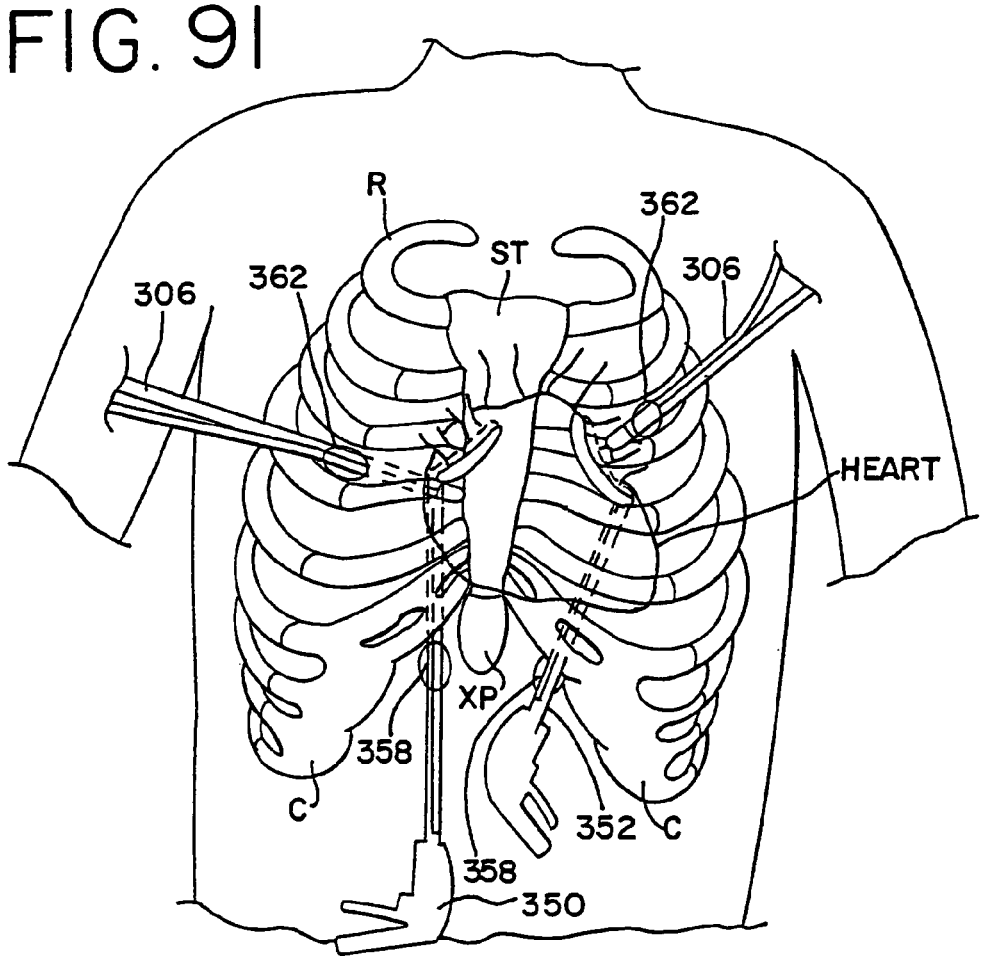
FIG. 91 is an anterior plan view of the heart showing ablation of the right and left pulmonary veins according to the sub-xyphoid method.

Using the sub-xyphoid approach, it also may be possible to perform ablation on both pairs of pulmonary veins at the same time either through the same incision or through separate incisions. FIG. 91 shows ablation of the left atrium near the right and left pulmonary veins. Right and left curved ablation devices 350 and 352 are similar to those described herein in FIGS. 83A and 83B. The ablation devices are inserted through access locations 358, although it is also possible that both devices could be inserted through one access location 358. Corresponding bullet dissectors 306 may be inserted through percutaneous intercostal penetrations 362 on the right and left sides, or the bullet dissectors may be inserted through a sub-xyphoid access location 358.

Figure 92:
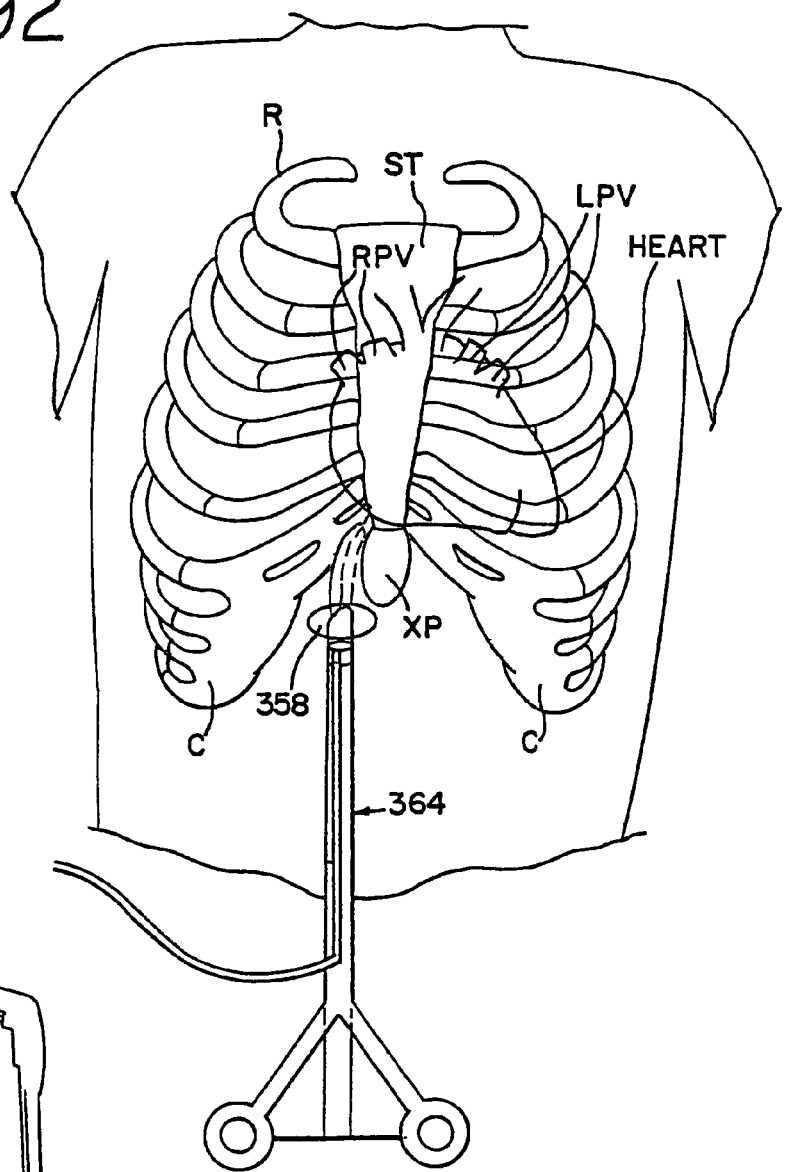
FIG. 92 is an anterior plan view of the heart showing an alternate instrument inserted according to the sub-xyphoid method.
Figure 95:
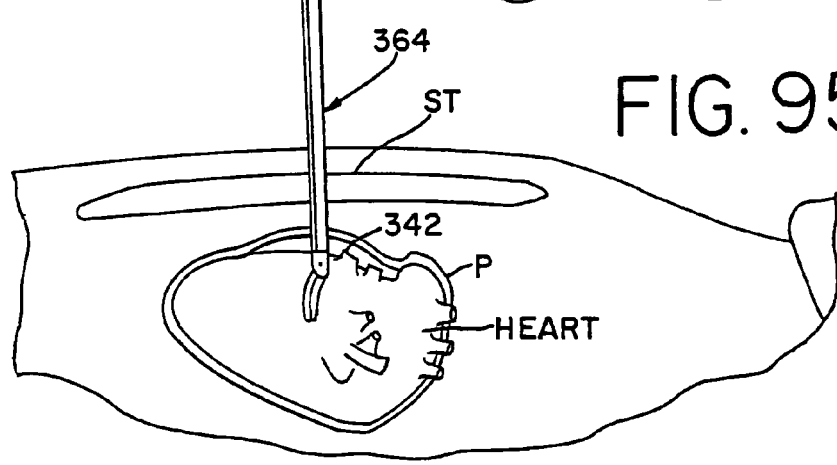
FIG. 95 is a side view of the heart and alternate instrument showing ablation according to the intercostal method.
Figure 93:
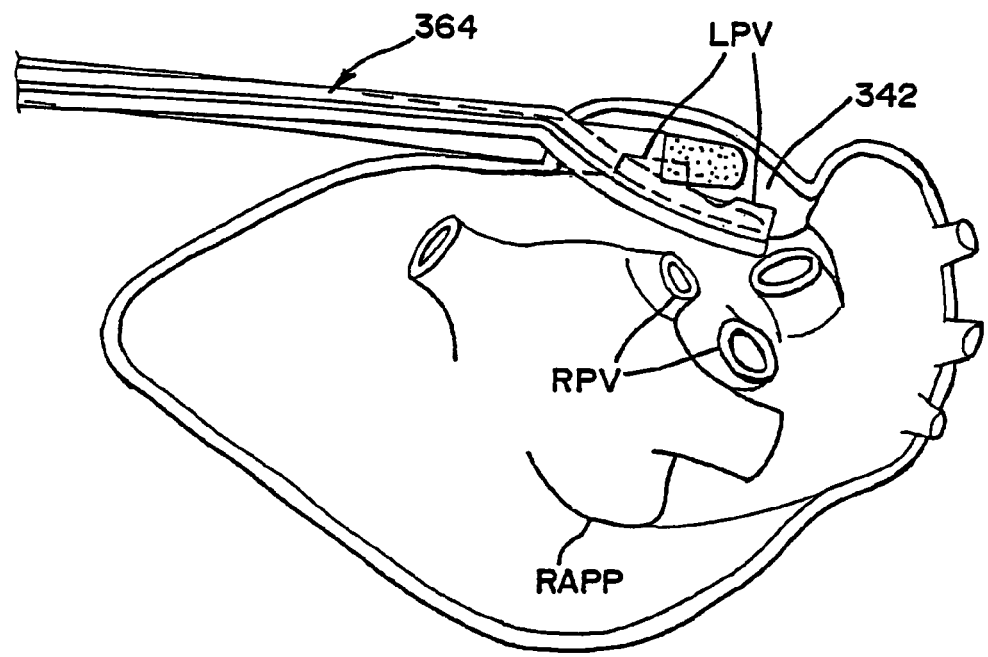
FIG. 93 is an enlarged side view of the heart showing ablation using the alternate instrument.
Figure 94:
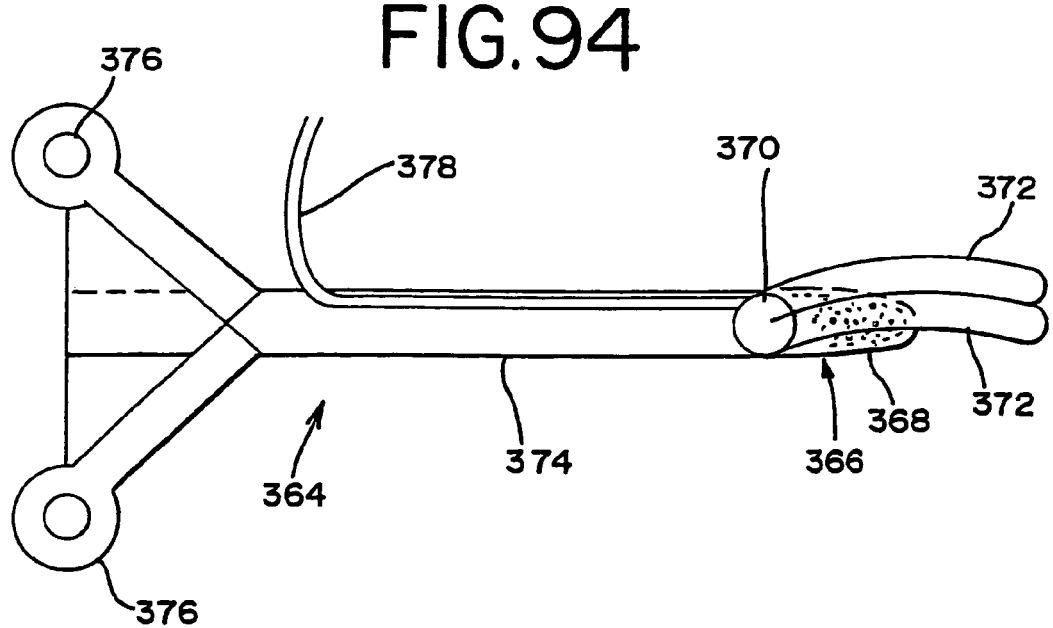
FIG. 94 is a top plan view of the alternate instrument.
Figure 96:
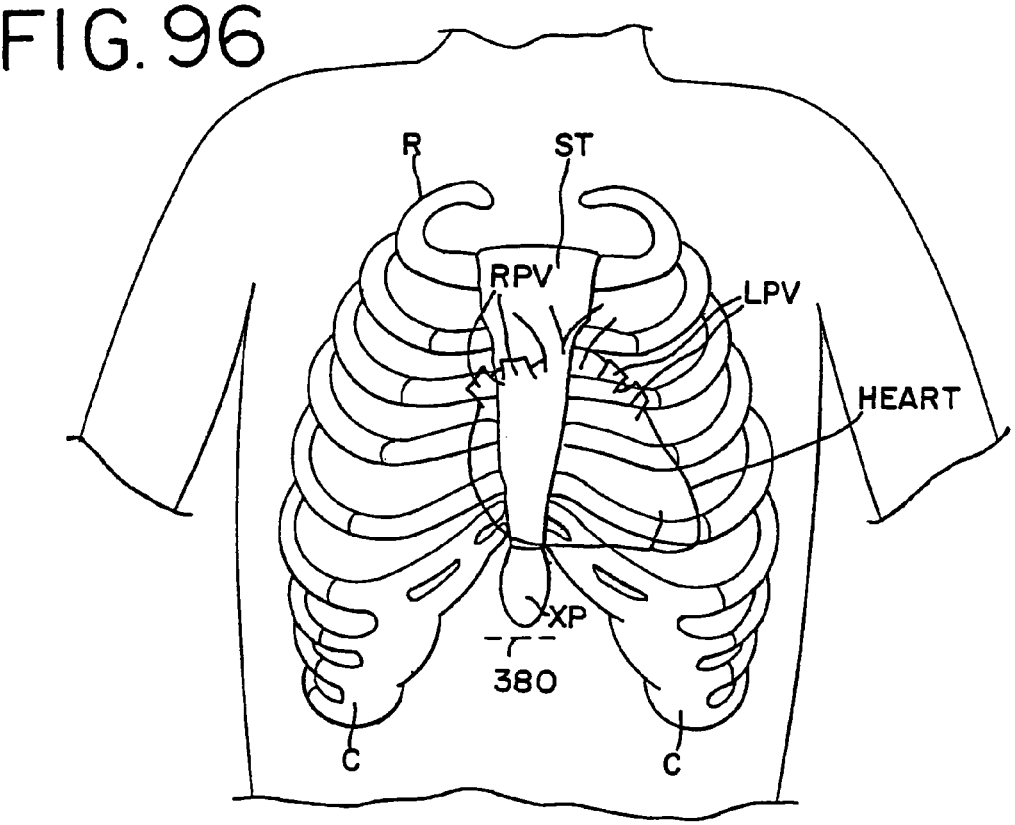
FIG. 96 shows an anterior plan view of the heart and access location for performing ablation according to the sub-xyphoid method using a single sub-xyphoid access location.
Figure 97:
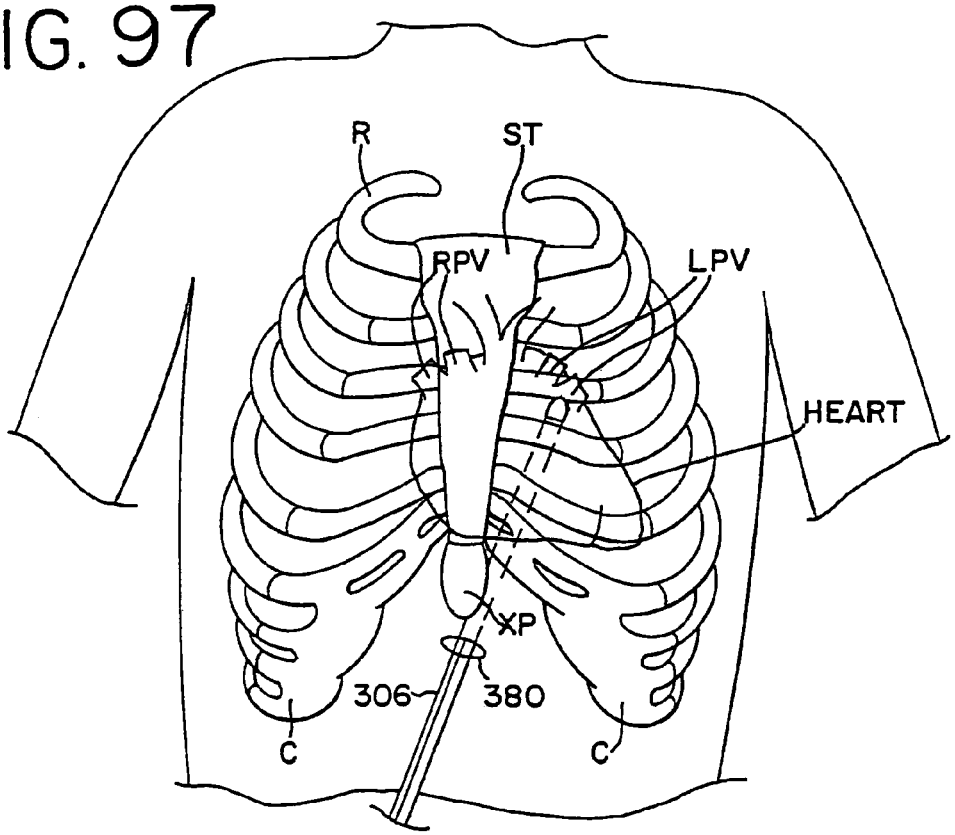
FIG. 97 shows an anterior plan view of the heart during insertion of the bullet dissector through the sub-xyphoid access location.

In FIGS. 92 and 93, the bullet dissector and ablation device are both inserted using a sub-xyphoid approach. The bullet dissector and ablation device may be separate as previously described or they may be combined into a single instrument for this, as well as the prior methods. FIGS. 92 and 93 show ablation by a combined dissector and ablation instrument 364. In FIG. 94, the combined instrument 364 includes a proximal end 366 which includes a bullet dissector head 368 and an endoscope 370. The proximal end 366 is carried by or mounted to an ablation device. Although the ablation device which is shown is similar to the grasper shown in FIGS. 63–65, other devices are possible. The ablation device includes grasping jaws 372, an elongated handle 374 and handle members 376. A saline irrigation tube 378 is carried by the handle 374 and supplies saline to the bullet dissector head 368. The combined dissector-ablation instrument 364 may be used for any of the above methods. Use of the instrument 364 in the intercostal method is illustrated by way of example in FIG. 95.

FIGS. 96–101 illustrate using the sub-xyphoid approach where the bullet dissector and ablation device are separate instruments through a single access location 380. An incision is first made in the sub-xyphoid region at the access location 380 near the tip of the xyphoid, as illustrated. This access location 380 is preferred because it allows access to both sides of the chest for treatment as needed. The size of the incision is about 1 cm. Then the bullet dissector 306 is inserted through the access location 380 and advanced to the pericardium P. The bullet dissector is preferably attached to an endoscope as previously described to aid in visualization. Once the bullet dissector proceeds to the appropriate point on the pericardium, a suitable cutting instrument such as a endoscope knife or scissors is introduced alongside the bullet dissector to create a small incision 382 in the pericardium just large enough for the head of the bullet dissector. The bullet dissector 306 is then inserted into the intrapericardial space 342 and advanced through the intrapericardial space, dissecting the pericardium from the heart as it advances, to the cardiac tissue to be treated.

Figure 98:
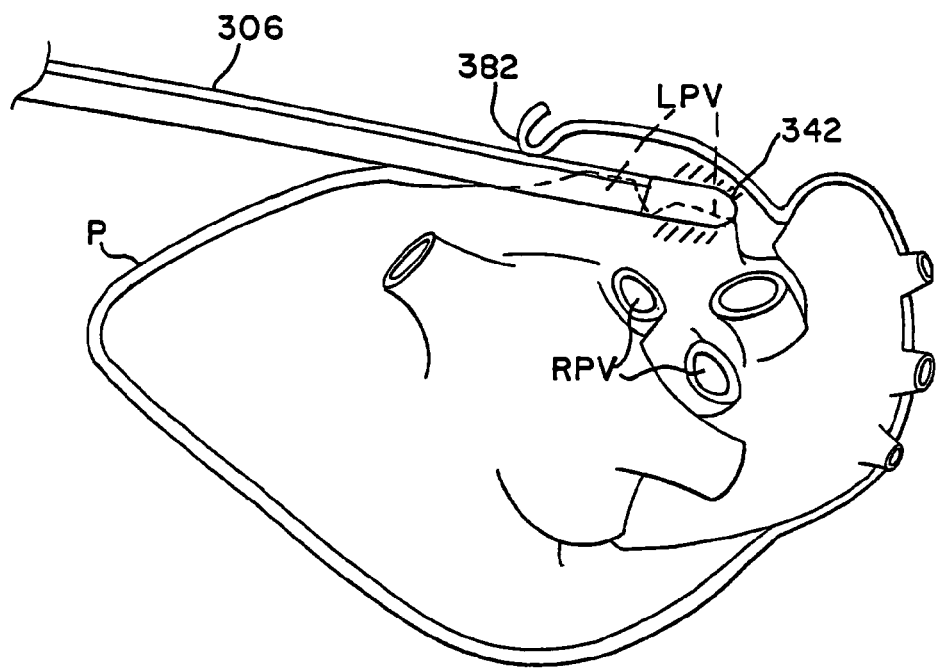
FIGS. 98–99 show an enlarged side view of the heart illustrating insertion of the bullet dissector into the intrapericardial space and dissection by the bullet dissector around the left pulmonary veins.
Figure 99:
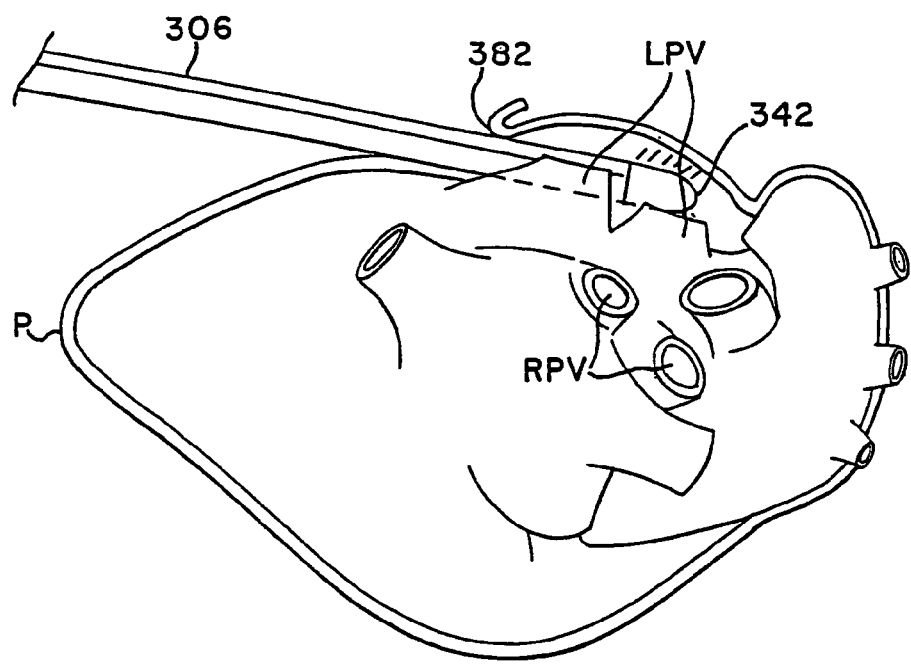
Figure 100:
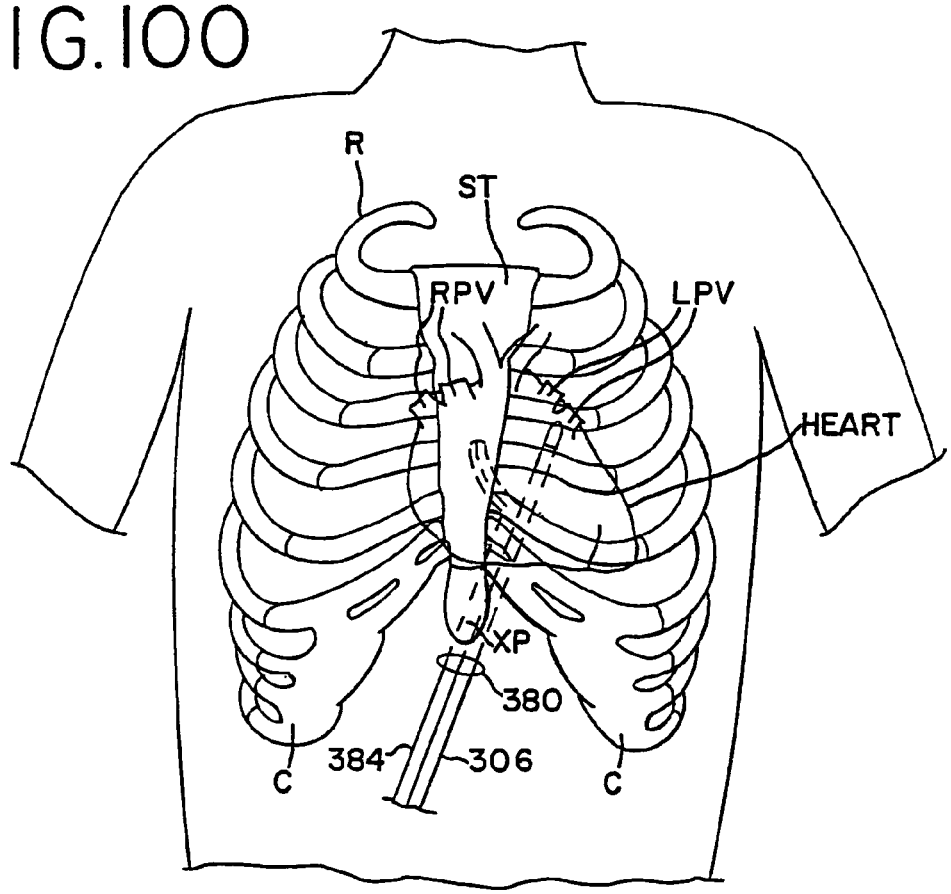
FIG. 100 shows an anterior plan view of the heart similar to FIG. 97 further including insertion of the ablation device.

For example, as shown in FIG. 98–99 the bullet dissector 306 is advanced within the intrapericardial space to the confluence of the left atrium and the pair of left pulmonary veins LPV. It is expected that minimal dissection of tissue will be performed by the bullet dissector around the left pulmonary veins whereas more tissue dissection will be required around the right pulmonary veins RPV. During dissection the bullet dissector will be advanced both above and below the atrium, the pulmonary veins and the confluence where the pulmonary veins meet the atrium to provide a working space which, as described above, is positively pressurized by insufflation. Creation of the working space allows for insertion of the jaws of the ablation device and aids in visualizing the cardiac tissue which requires treatment.

Once dissection is completed, an ablation device 384 may be inserted through the sub-xyphoid access location 380. The ablation device may be inserted into the intrapericardial space alongside the bullet dissector 306 either by enlarging the pericardial incision using a suitable cutting device or by causing the pericardial incision to stretch or widen to accommodate the ablation device. It is also possible to remove the bullet dissector 306 and then insert the ablation device, although use of the bullet dissector in combination with the ablation device is preferred. The ablation device is advanced to the cardiac tissue to be treated such as, for example, the confluence of the atrium and the pulmonary veins.

With the aid of the bullet dissector and endoscope, the tissue to be treated is identified. Within the working space created by the bullet dissector, one jaw of the ablation device is positioned below the pulmonary veins and the other jaw is positioned above the pulmonary veins. The ablation device is properly positioned around the tissue to be treated and then clamped. Verification may be performed to ensure that the clamped tissue between the jaws of the ablation device is the location which requires ablation. The bullet dissector may help visualize and confirm that the appropriate cardiac tissue is being treated. The curved jaw members of the ablation device should be oriented such that the concave portion faces the pulmonary veins and the convex portion faces the atrium.

Figure 101:
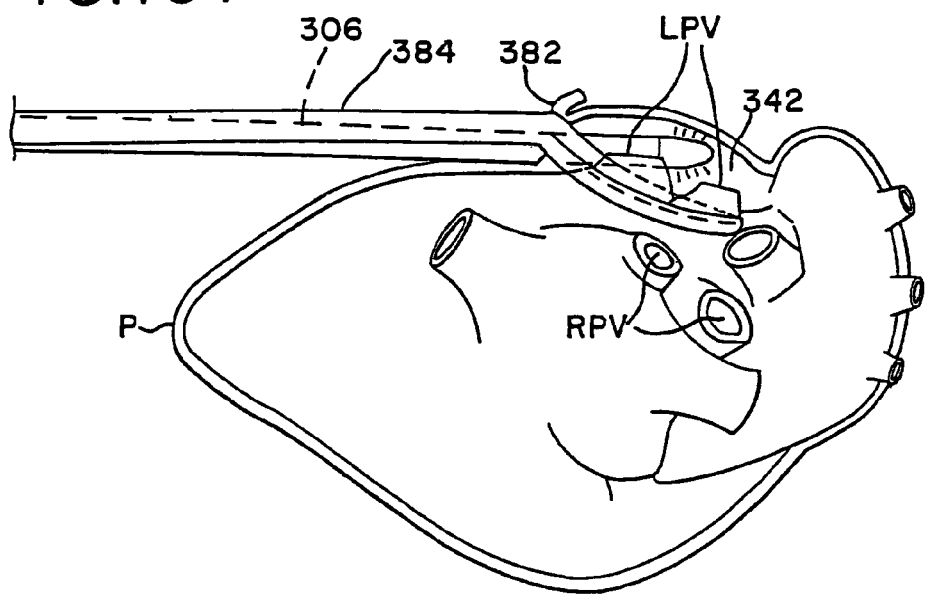
FIG. 101 shows an enlarged side view of the heart illustrating ablation where sub-xyphoid access of the bullet dissector and ablation device is achieved using a single sub-xyphoid access location.

Ablation of the cardiac tissue is performed by using RF energy to create an ablation lesion, as previously described. The sub-xyphoid approach may be used to create ablations as shown in FIGS. 74–77. For example, FIG. 101 shows the ablation device ablating the left atrium near the left pulmonary veins which creates a circumferential ablation lesion similar to the one shown in FIG. 77. Thereafter the jaws of the ablation device are unclamped and moved to another location which requires ablation.

The sub-xyphoid method can be repeated as necessary to create additional ablations. For example, a second circumferential ablation may be created around the right pulmonary veins. When using an ablation device similar to the grasper shown in FIGS. 63–65, ablation of a second pair of pulmonary veins may be performed by rotating the grasper 180 degrees so that the concave portion of the jaw members faces the pulmonary veins. In the case of the grasper in FIGS. 33–37, 83A and 83B, it may be necessary to use right and left curved ablation devices when using the sub-xyphoid approach so that the concave portion of the jaw members faces the appropriate pair of pulmonary veins. For example, the right curved grasper 350 may be used to treat the atrium near the right pulmonary veins and then withdrawn through the sub-xyphoid access location 380. Thereafter, the left curved grasper 352 may be inserted through the access location 380 and used to ablate the atrium near the left pulmonary veins.

During ablation drainage of excess fluid may be performed by inserting a drainage tube through the sub-xyphoid access location 380. Once all ablation locations are treated, the ablation device and bullet dissector are withdrawn and the sub-xyphoid access location 380 is closed using well-known techniques. It is not necessary to suture the pericardium incision.

Importantly, each method may be performed with a beating heart or with the heart stopped. Where the heart is stopped, it is understood that the patient must be connected to a cardio-bypass machine. The methods may be performed either with the lungs inflated or deflated. If the lung is deflated, then the patient must be connected to a respirator. It is realized that where both the heart is stopped and the lung deflated, then the patient will be connected to a cardiopulmonary bypass system. Where the lung is deflated, it may be preferred to deflate only one lung at a time before proceeding to deflate the other lung. For example, where cardiac tissue adjacent each pair of right and left pulmonary veins requires treatment, either the right lung or the left lung may be deflated, but not both. After all cardiac tissue requiring ablation is treated on the deflated side, the lung is re-inflated and the process is repeated for the other side of the heart.

Each method may be used to create transmural ablation as previously described herein for epicardial or endocardial surfaces. For epicardial ablations, an incision is usually made into the pericardium to access the epicardial surface. Although it is possible to perform ablations without penetrating the pericardium, penetration into the intrapericardial space, the space within the pericardial cavity between the pericardium and the epicardium, may allow for better positioning of the ablation device for ablation of the identified cardiac tissue. Where the ablation device is inserted into the intrapericardial space, it is advanced to the location which has been identified as requiring ablation. The ablation device directly contacts the epicardial surface of the heart relating to this location and the location is ablated. Methods of epicardial ablation for creating lesions around the pulmonary veins are disclosed in U.S. Pat. No. 6,161,543, which is incorporated herein by reference.

For endocardial ablation, an incision is made in the heart wall by a blade on the tip of the ablation device or by other suitable instrument. The incision in the heart wall may be treated with an appropriate suture such as a purse string suture 327 shown in FIG. 76. Then the dissector and endoscope can locate and identify the location to be ablated. Once the location is identified, one of the jaws of the ablation device or grasper is inserted into the heart to directly contact the endocardial surface which requires ablation. After ablation, the jaw of the ablation device, is withdrawn back through the incision. The process is repeated until all locations are treated.

Thus, it can be seen that a transmural ablation device and method have been provided that overcome the limitations of the prior art. First, current technology involves ablation devices deliver ablation energy to either the inside (endocardium) or outside (epicardium) of the heart. Using these techniques, the tissue ablation proceeds from one wall of the heart through the tissue to the opposite wall. To date, there has been no reliable way to consistently achieve lesions that penetrate the full thickness of the atrial wall (transmural lesions), and there has been no way to determine either continuity or transmurality of these lesions. If the lesion does not penetrate through enough of the atrial wall, conduction can still occur, and the lesion does not fully block the electrical signals that are causing the arrhythmia. Using an endocardial approach, if the lesion penetrates too far through the wall, critical structures such as coronary arteries, veins, or the esophagus can be damaged on the outside of the heart. Using an epicardial approach, if the lesion penetrates too far, blood can be coagulated, or critical structures such as valves, nodes, or connective tissue can be damaged on the inside of the heart.

There has also been no reliable and consistent way to safely achieve fully continuous, long (greater than 1 cm) lesions in the atrial wall without a high risk of thrombus, damage to critical structures, or extensive damage to the atrial tissue.

The present invention overcomes these shortcomings because the conductive area of each electrode is very narrow compared to the width of the clamped area. As a result, the thermal damage to the tissue is minimal. In contrast, current technology uses catheter electrodes which are typically 1 or 2 mm diameter requiring a lesion width of almost 8 mm to achieve a depth of 5 mm. Using the present invention, a lesion depth of 5 mm with a width of less than 2 mm can be achieved. This aspect of the invention allows for longer linear lesions with less power delivery because less tissue is being heated. There is, therefore, considerably less damage to healthy atrial tissue for a lesion of a given depth and length. Recent efforts in creating linear lesions using endocardial electrodes resulted in ablation of over 20% of the atrial endocardium, and a commensurate decrease in atrial contractility.

Another advantage of this device is that ablation can be done on a beating heart. Using a high modulus material such as tungsten or carbon fiber would allow a minimum diameter, and a maximum clamping pressure for a given clamping length. Once the device is clamped onto the atrial wall, the position of the electrodes can be verified by visually inspecting the position of the outer electrode before delivery of RF energy. If the clamping pressure is higher than the atrial pressure, then clamping over a coronary artery would cut off blood flow, and the resulting change in the EKG would act as a warning to the user prior to applying RF energy. The clamping will prevent any movement of the electrodes relative to the heart wall, and RF energy can be applied with confidence that the ablated tissue will be contained completely between the two electrodes.

Another important feature of this device is that the energy transfer is limited to the tissue clamped between the two electrodes. The insulated electrodes protect structures on the outside of the heart from being exposed to RF energy. Because of this limitation of current flow, damage to critical structures can be avoided.

Another advantage of this device is that it can easily be adapted to a minimally invasive thoracoscopic approach.

The device shown has been reduced to a 5 mm diameter device, and can probably be reduced to 3 mm or less. Using video thoracoscopy, the device could be introduced through a small intracostal incision, and used to create fully transmural linear lesions on a beating heart, possibly under local anesthesia on an anesthetized patient.

Accordingly, a device and method for performing transmural ablation has been provided that meets all the objects of the present invention. While the invention has been described in terms of certain preferred embodiments, there is no intent to limit the invention to the same. Instead it is to be defined by the scope of the appended claims.

What is claimed:

1. A device for clamping and ablating cardiac tissue comprising:
    first and second jaws, the jaws being relatively movable between a first open position and a second clamped position, the jaws having opposed clamping surfaces, each clamping surface having a width;
    a first elongated conductive ablation member carried by the first jaw;
    a second elongated conductive ablation member carried by the second jaw;
    the first and second conductive ablation members being adapted to be connected to a bipolar RF energy source;
    each conductive ablation member having a surface contoured to engage tissue clamped between the jaws without cutting and positioned to provide an ablation line through tissue which is substantially narrower than the width of the clamping surface; and
    each jaw comprising at least three distinct elements, an elongated support member supporting substantially the entire length of its associated conductive ablation member, the first or second elongated conductive ablation member, and an insulator disposed between the conductive member and the support member.

2. The device of claim 1 wherein the ablation members are between approximately 3 to 8 cm in length and approximately 0.12 to 0.6 mm in width.

3. The device of claim 1 in which the insulator is supported by the support member and the conductive member is supported by the insulator.

4. The device of claim 2 in which the conductive member is a wire.

5. The device of claim 1 in which the conductive member is a wire.

6. The device of claim 4 in which the wire is supported by the insulator.

7. The device of claim 5 in which the wire is supported by the insulator.

8. The device of claim 2 in which the insulator is supported by the support member and the conductive member is supported by the insulator.

9. The device of claim 1 in which the clamping surfaces of the conductive ablation members are convex.

10. The device of claim 1 in which each conductive ablation member defines an interior bore.

11. The device of claim 1 in which each conductive ablation member defines a generally annular cross-sectional shape.

* * * * *